(12) United States Patent
Jardieu et al.

(10) Patent No.: US 7,351,816 B2
(45) Date of Patent: *Apr. 1, 2008

(54) NUCLEIC ACID ENCODING ANTI-IGE ANTIBODIES

(75) Inventors: Paula M. Jardieu, Berkeley, CA (US); Leonard G. Presta, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 169 days.

This patent is subject to a terminal disclaimer.

(21) Appl. No.: 10/968,237

(22) Filed: Oct. 19, 2004

(65) Prior Publication Data

US 2005/0059806 A1    Mar. 17, 2005

Related U.S. Application Data

(60) Continuation of application No. 09/925,179, filed on Aug. 8, 2001, now Pat. No. 6,914,129, which is a continuation of application No. 08/466,163, filed on Jun. 6, 1995, now Pat. No. 6,329,509, which is a division of application No. 08/405,617, filed on Mar. 15, 1995, now abandoned, which is a continuation of application No. 08/185,899, filed as application No. PCT/US92/06860 on Aug. 14, 1992, now abandoned, which is a continuation-in-part of application No. 07/879,495, filed on May 7, 1992, now abandoned, and a continuation-in-part of application No. 07/744,768, filed on Aug. 14, 1991, now abandoned.

(51) Int. Cl.
*C07H 21/04* (2006.01)

(52) U.S. Cl. ................ 536/23.53; 530/387.1; 530/387.3; 435/70.1; 435/320.1; 435/326; 435/328

(58) Field of Classification Search .............. 536/23.53; 530/387.3, 387.1; 435/70.1, 320.1, 326, 435/328
See application file for complete search history.

(56) References Cited

U.S. PATENT DOCUMENTS

| 4,629,783 | A | 12/1986 | Cosand |
| 4,714,759 | A | 12/1987 | Whitaker, Jr. |
| 4,861,579 | A | 8/1989 | Meyer et al. |
| 4,940,782 | A | 7/1990 | Rup et al. |
| 5,428,133 | A | 6/1995 | Chang |
| 5,585,089 | A | 12/1996 | Queen et al. |
| 5,821,337 | A | 10/1998 | Carter et al. |
| 6,329,509 | B1 * | 12/2001 | Jardieu et al. |
| 6,685,939 | B2 * | 2/2004 | Jardieu et al. |
| 6,699,472 | B2 * | 3/2004 | Jardieu et al. |
| 6,914,129 | B2 * | 7/2005 | Jardieu et al. |

FOREIGN PATENT DOCUMENTS

| EP | 255249 | 2/1988 |
| EP | 263655 | 4/1988 |
| JP | 58-156285 | 9/1983 |
| WO | WO 89/04834 | 6/1989 |
| WO | WO 89/06138 | 7/1989 |
| WO | WO 90/07861 | 7/1990 |
| WO | WO 91/09967 | 7/1991 |
| WO | WO 91/09968 | 7/1991 |

OTHER PUBLICATIONS

Elgert et al., Immunology: Understanging the Immune System, 1996, p. 59.*
Simmons et al., Journal of Immunogical Methods, 263:133-147, May 2002.*
Jones, DT., Pharmacogenomics Jornal, 1:126-134, 2001.*
Tosatto et al., Surrent Pharmaceutical Design, 12:2067-2086, 2006.*
Mariuzza et al. (Annu. Rev. Biophys. Biophys. Chem. 1987; 16: 139-159).*
Gussow et al. (Methods in Enzymology. 1991; 203: 99-121).*
Hamilton (Clin. Chem. 40(11):2186-2192, 1994).*
U.S. Appl. No. 08/146,206, filed Nov. 17, 1993, Carter et al.
Baniyash et al., "Anit-IgE monoclonal antibodies directed at the $Fc_\epsilon$ receptor binding site" *Molecular Immunology* 25(8):705-711 (1988).
Baniyash et al., "Inhibition of IgE Binding to Mast Cells and Basophils by Monoclonal Antibodies to Murine IgE" *European Journal of Immunology* 14:799-807 (1984).
Baniyash, "Immunochemical Characterization of the Interaction Between Immunoglobulin E and Its Receptor" *Weizmann Institute of Science* (Thesis) (May 1986).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue" Journal of Cell Biology 111:2129-2138 (1990).
Burt et al., "Analysis of the interaction between rat immunoglobulin E and rat mast cells using anti-peptide antibodies" *Molecular Immunology* 24(4):379-389 (1987).
Burt et al., "Inhibition of binding of rat IgE to rat mast cells by synthetic IgE peptides" European Journal of Immunology 17:437-440 (1987).
Casale et al., "Recombinant Human Monoclonal Anti-IgE Therapy in Allergic Rhinitis" *Journal Allergy Clinical Immunology* (Abstract) 97(1):Part 3 (1996).
Conrad et al., "The Interation of Human and Rodent IgE with the Human Basophil IgE Receptor" *J. of Immunology* 130(1): 327-333 (1983).
Conrad, D.H., "$Fc_\epsilon$RII/CD23: The low affinity receptor for IgE" *Ann. Rev. Immunol.* 8:623-639 (1990).

(Continued)

Primary Examiner—Stephen L. Rawlings
Assistant Examiner—Brad Duffy
(74) Attorney, Agent, or Firm—Craig G. Svoboda

(57) ABSTRACT

The present invention describes IgE antagonists (including variant anti-IgE antibodies) and their use in diagnosis, therapy or prophylaxis of allergic and other IgE-mediated disorders, including asthma, food allergies, hypersensitivity and anaphylactic reactions.

53 Claims, 7 Drawing Sheets

OTHER PUBLICATIONS

Deisenhofer, J, "Crystallographic Refinement and Atomic Models of a Human Fc Fragment and Its Complex with Fragment B of Protein A from *Staphylococcus aureus* at 2.9- and 2.8-A Resolution" *Biochemistry* 20(9):2361-2370 (1981).

Duncan et al., "Localization of the Binding Site for the Human High-Affinity Fc Receptor on IgG." *Nature* 332:563-564 (Apr. 7, 1988).

Emery et al., "Humanised monoclonal antibodies for therapeutic applications" *Exp. Opin. Invest. Drugs* 3(3):241-251 (1994).

Geha et al., "IgE sites relevant for binding to type 1 Fc epsilon (FCER) receptors on mast cells" *J. Allergy & Clin. Immunol.* (Abstract No. 20) 79(1):129 (1987).

Gillies et al., "Antigen Binding and Biological Activities of Engineered Mutant Chimeric Antibodies with Human Tumor Specificities" *Hum. Antibod. Hybridomas* 1(1):47-54 (1990).

Glennie et al., "Preparation and Performance of Bispecific F(ab'$\gamma$)$_2$ Antibody Containing Thioether-Linked Fab'$\gamma$ Fragments" *J. Immunol.* 139(7):2367-2375 (Oct. 1, 1987).

Hakimi et al., "The $\alpha$ subunit of the human Ige receptor (FcERI) is sufficient for high affinity IgE binding" *Journal of Biological Chemistry* 265(36):22079-22081 (1990).

Helm et al., "Blocking of passive sensitization of human mast cells and basophil granulocytes with IgE antibodies by a recombinant human $\epsilon$-chain fragment of 76 amino acids" *Proc. Natl. Acad. Sci.* 86:9465-9469 (Dec. 1989).

Helm et al., "Identification of the High Affinity Receptor Binding Region in Human Immunoglobulin E" *Journal of Biological Chemistry* 271(13):7494-7500 (Mar. 29, 1996).

Helm et al., "The mast cell binding site on human immunoglobulin E" *Nature* 331:180-183 (Jan. 14, 1988).

Hoffman, D. R., "Enzyme-linked immunosorbent assays (ELISA) for immunoglobulin E and blocking antibodies" *Methods in Enzymology*, Chapter 45, 73:656-666 (1981).

Hook et al., "Monoclonal Antibodies Defining Epitopes on Human IgE" *Molecular Immunology* 28(6):631-639 (1991).

Ishizaka et al., "Mechanisms of passive sensitization III. Number of IgE Molecules and Their Receptor Sites on Human Basophil Granulocytes" *J. Immunol.* 111(2):500-511 (Aug. 1973).

Ishizaka, K., "Immunoglobulin E (IgE)" *Methods in Enzymology* 116(Part II):76-94 (1985).

Jefferis et al., "Molecular Definition of Interaction Sites on Human IgG for Fc Receptors (huFc$\gamma$R)" *Molecular Immunology* 27(12):1237-1240 (1990).

Jefferis, R., "Structure-function relationships in human immunoglobulins" *Netherlands J. Medicine* 39:188-198 (1991).

Jones et al., "Replacing the Complementarity-Determining Regions in a Human Antibody with Those From a Mouse." *Nature.* 321:522-525 (May 29, 1986).

Kabat *Sequences of Proteins of Immunological Interest* (Fourth Ed.), 4th edition pps. 41-42, 167-168 (1987).

Kahan, "Immunosuppressive therapy" *Current Opinion in Immunology* 4(5):553-560 (Oct. 1992).

Kulczycki et al., "The Interaction of IgE with Rat Basophilic Leukemia Cells, Evidence for Specific Binding of IgE" *Journal of Experimental Medicine* 139:600-616 (1974).

Kumar et al., "Amino acid variations at a single residue in an autoimmune peptide, etc." *P.N.A.S USA* 87:1337-1341 (Feb. 1990).

Kurokawa et al., "Expression of human immunoglobulin E $\epsilon$ chain cDNA in *E. coli*" *Nucleic Acids Research* 11(10):3077-3085 (1983).

Lazar et al., "Transforming Growth Factor $\alpha$: Mutation of Aspartic Acid 47 and Leucine 48 Results in Different Biological Activities" *Molecular & Cellular Biology* 8(3):1247-1252 (Mar. 1988).

Liu et al., "Expression of a biologically active fragment of human IgE $\epsilon$ chain in *Escherichia coli*" *Proc. Natl. Acad. Sci.* 81:5369-5373 (Sep. 1984).

Metzger and Kinet, "How Antibodies Work: Focus on Fc Receptors" *FASEB J* 2(1):3-11 (Jan. 1988).

Neurath, A. R., "Use of [125] I-labeled anti-2, 4-dinitrophenyl (DNP) antibodies as a general tracer in solid-phase radioimmunoassays" *Methods in Enzymology* 73:127-138 (1981).

Nio et al., "Inhibition of histamine release by synthetic human IgE peptide fragments: structure-activity studies" *Peptide Chemistry* pp. 203-208 (1989).

Nissim et al., "Fine specifically of the IgE Interaction with the Low and High Affinity Fc Receptor" *J. Immunol.* 150:1365-1374 (1993).

Nissim et al., "Mapping of the high affinity Fc$\epsilon$ receptor binding site to the third constant region domain of IgE" *EMBO Journal* 10(1):101-107 (Jan. 1991).

Nissim et al., "The Use of Mouse/Human IgE Chimeras to Map the FceR Binding Site of IgE" *Methods* 8:124-132 (1995).

Nitta et al., "Preliminary trial of specific targeting therapy against malignant glioma" *Lancet* 335(8686):368-371 (Feb. 17, 1990).

Padlan et al., "A model of the Fc of immunoglobulin E" *Molecular Immunology* 23(10):1063-1075 (1986).

Paul, W.E. ed. *Fundamental Immunology*, Raven Press, NY, 3rd edition pp. 822-826 (1993).

Queen et al., "A humanized antibody that binds to the interleukin 2 receptor" *Proc. Natl. Acad. Sci. USA* 86(24):10029-10033 (Dec. 1989).

Rao et al., "Characterization of a Monoclonal Antibody Directed Against the Murine B Lymphocyte Receptor for IgE" *Journal of Immunology* 138(6):1845-1851 (Mar. 15, 1987).

Riechmann et al., "Reshaping Human Antibodies for Therapy" *Nature* 332:323-327 (Mar. 24, 1988).

Riske et al., "High Affinity Human IgE Receptor (Fc$\epsilon$RI). Analysis of functional Domains of the $\alpha$-Subunit with Monoclonal Antibodies" *Journal of Biological Chemistry* 266(17):11245-11251 (Jun. 15, 1991).

Robertson et al., "IgE structure-function relationships defined by sequence directed antibodies induced by synthetic peptides" *Molecular Immunology* 25(2):103-113 (1988).

Robertson et al., "The Isolation of Polypeptides With FSH Suppressing Activity From Bovine Follicular Fluid Which Are Structurally Different to Inhibin" *Biochem. and Biophysical Res. Comm.* 149(2):744-749 (Dec. 16, 1987).

Riott et al., "Antigen Receptor Molecules" *Immunology*, Mosby Limited, 3rd edition pp. 4.8 (1996).

Rudikoff et al., "Single amino acid substitution altering antigen-binding specificity" *Proc. Natl. Acad. Sci. USA* 79:1979-1983 (1982).

Schwarzbaum et al., "Mapping of murine IgE epitopes involved in IgE-Fc$\epsilon$ receptor interactions" *European Journal of Immunology* 19:1015-1023 (1989).

"Sequences of Immunological Interest", U.S. Dept. of Health and Human Service vol. 1 (1991).

Shields et al., "Inhibition of Allergic Reactions with Antibodies to IgE" *International Archives of Allergy and Immunology* 107(1-3):308-312 (May 1995).

Spiegelberg et al., "Effect of Myeloma IgE Injections on Passive and Activei Cutaneous Anaphylaxis in Rats" *Journal of Immunology* 136(1):131-135 (Jan. 1, 1986).

Stanworth et al., "Synthetic peptides comprising sequences of the human immunoglobulin E heavy chain capable of releasing histamine" *Biochemical Journal* 180(3):665-668 (1979).

Stanworth et al., "The use of synthetic peptides in the delineation of immunoglobulin antigenic epitopes and Fc effector functions" *Symposium on Synthetic Peptides as Antigens* (Ciba Foundation symposium 119), New York:Wiley vol. 119:226-244 (1986).

Sung Co et al., "Humanized antibodies for therapy" *Nature* 351:501-502 (1991).

Sutton et al., "The Human IgE Network" *Nature* 366:421-428 (Dec. 2, 1993).

Tao and Morrison, "Studies of Aglycosylated Chimeric Mouse-Human IgG: Role of Carbohydrate in the Structure and Effector Functions Mediated by the Human IgG Constant Region." *J. of Immunology* 143(8):2595-2601 (Oct. 15, 1989).

Tung, A. S., "Production, purification, and characterization of antigen-specific murine monoclonal antibodies of IgE class" *Methods in Enzymology*, Chapter 6, 92:47-66 (1983).

Vercelli et al., "The B-cell binding site on human immunoglobulin E" *Nature* 338:649-651 (Apr. 20, 1989).

Weetall et al., "Mapping the site of interaction between murine IgE and its high affinity receptor with chimeric Ig" *J. Immunol.* 145(11):3849-3854 (Dec. 1, 1990).

Weiss et al., "Interactions of cancer cells with the microvasculature during metastasis" *FASEB J.* 2(1):12-21 (Jan. 1988).

Williams, G., "Novel antibody reagents: production and potential" *TIBTECH* 6:36-42 (1988).

Wong et al., "Bi-specific monoclonal antibodies: selective binding and complement fixation to cells that express two different surface antigens" *J. Immunol.* 139(4):1369-1374 (1987).

* cited by examiner

```
                β-strand A        loop AB            β-strand B
360  XDSNPRGVSAYLSRPSPFDXLFIRKSPTIT
                                  ‾‾‾‾‾‾‾‾‾‾‾‾‾   ‾‾‾‾‾‾‾‾
(SEQ ID NO:1)                         1,7              8 loop BC      β-strand C          loop CD
390  CLVVDLAPSKGTVNLTWSRXAASXXGKPVNH
          ‾‾‾‾‾‾‾‾‾‾‾‾‾         ‾‾‾‾‾‾‾‾‾‾‾‾
               2                    9                3

β-strand D    loop DE       β-strand E           loop EF
420  STRKEEKQRXNXXGTLTVTSTLPVGTRDWI
     ‾‾‾‾‾‾‾‾‾‾‾          ‾‾‾‾‾‾‾‾‾‾‾‾‾‾‾‾   ‾‾‾‾‾‾‾‾‾‾
          6                     10                 4

β-strand F        loop FG    β-strand G
450  EGETYQCRVTHPHLPRALXMRSTTKTSGP
     ‾‾‾‾‾‾‾‾‾‾‾‾‾        ‾‾‾‾‾‾‾  ‾‾‾‾‾‾‾‾‾‾
         11                 5           12
```

FIG. 1

MaE11 Light Chain (SEQ ID NO:2)
DIVLTQSPASLAVSLGQRATISCKASQSVDYDGDSYMNWYQQKPGQPPILLIYAASYLG
SEIPARFSGSGSGTDFTLNIHPVEEEDAATFYCQQSHEDPYTFGAGTKLEIK MaE11 Heavy Chain (SEQ ID NO:3)
DVQLQESGPGLVKPSQSLSLACSVTGYSITSGYSWNWIRQFPGNKLEWMGSITYDGSS
NYNPSLKNRISVTRDTSQNQFFLKLNSATAEDTATYYCARGSHYFGHWHFAVWGAGTTVT
VSSAKTTPPSVYPLAR Mae13 Light Chain (SEQ ID NO:4)
DIVMTQSQKFMSTSVGDRVSVTCKASQNVSSNVAWYQQKPGQSPKALIYSASYRYSGV
PDRFTGSGSGTDFTLTISNVQSEDLAEYFCQQYYTYPLYTFGGGTKLEIKRADAAPTVSI
FPPSTR Mae13 Heavy Chain (SEQ ID NO:5)
DVQLQESGPGLVKPSQSLSLTCTVTGYTITSDNAWNWIRQFPGNKLEWMGYINHSGTT
SYNPSLKSRISITRDTSKNQFFLQLNSVTTEDTATYYCAWVVAYAMDYWGQGTSVTVSSA
KTTPPSVYPLAR Mae15 Light Chain (SEQ ID NO:6)
DIQLTQSPASLAVSLGQRATISCKASQSVDYDGDSYMNWYQQKPGQPPKLLIYAASNLES
GIPARFSGSGSGTDFTLNIHPVEEEDAATYYCQQSNEDPFTFGAGT Mae15 Heavy Chain (SEQ ID NO:7)
DVQHQESEPDLVKPSQSLSLTCTVTGYSITSGYNRHWIRQFPGNKLEWMGYIHYSGST
NYNPSLKRRISITRDTSKNQFFLQLNSVTTEDTATYYCARGSIYYYGSRYRYFDVWGAGT
TVTVSSAKRHPHLSIHWPG

FIG. 2

Humanized MaE11 Version 1 (intact IgG)

Heavy Chain   (SEQ ID NO:8)
EVQLVESGGGLVQPGGSLRLSCAVSGYSITSGYSWNWIRQAPGKGLEWVASITYDGSTNY
ADSVKGRFTISRDDSKNTFYLQMNSLRAEDTAVYYCARGSHYFGHWHFAVWGQGTLVTVS
SASTKGKPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPEL
LGGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDK
SRWQQGNVFSCSVMHEALHNHYTQKSLSLSPGK Light Chain   (SEQ ID NO:9)
DIQLTQSPSSLSASVGDRVTITCRASQSVDYDGDSYMNWYQQKPGKAPKLLIYAASYLES
GVPSRFSGSGSGTDFTLTISSLQPEDFATYYCQQSHEDPYTFGQGTKVEIKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC

FIG. 3

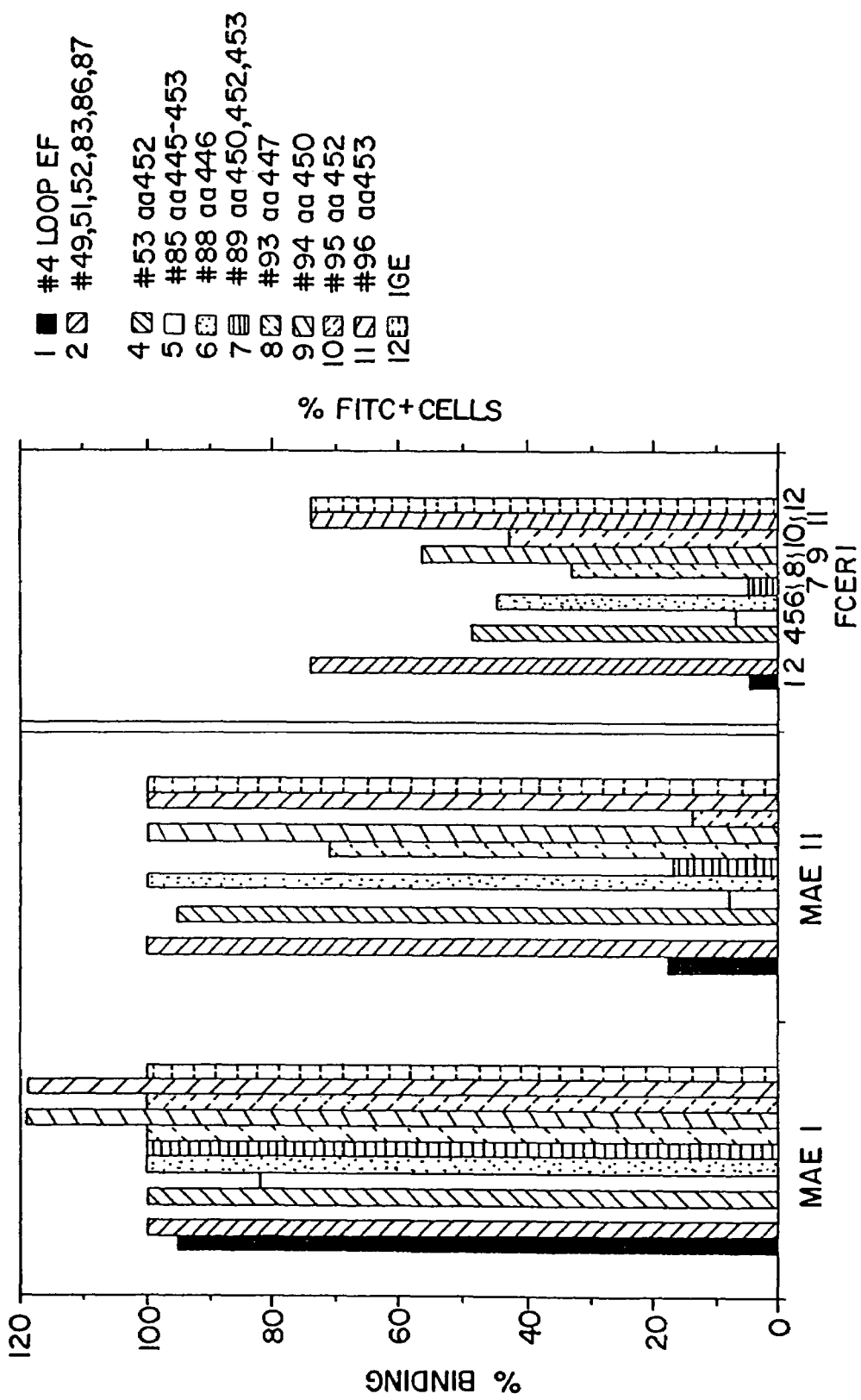

SEQUENCE LISTING

```
<160> NUMBER OF SEQ ID NOS: 68

<210> SEQ ID NO 1
<211> LENGTH: 109
<212> TYPE: PRT
<213> ORGANISM: Homo sapiens

<400> SEQUENCE: 1

Asp Ser Asn Pro Arg Gly Val Ser Ala Tyr Leu Ser Arg Pro Ser
  1               5                  10                  15

Pro Phe Asp Leu Phe Ile Arg Lys Ser Pro Thr Ile Thr Cys Leu
                 20                  25                  30

Val Val Asp Leu Ala Pro Ser Lys Gly Thr Val Asn Leu Thr Trp
                 35                  40                  45

Ser Arg Ala Ser Gly Lys Pro Val Asn His Ser Thr Arg Lys Glu
                 50                  55                  60

Glu Lys Gln Arg Asn Gly Thr Leu Thr Val Thr Ser Thr Leu Pro
                 65                  70                  75

Val Gly Thr Arg Asp Trp Ile Glu Gly Glu Thr Gln Cys Arg Val
                 80                  85                  90

Thr His Pro His Leu Pro Arg Ala Leu Met Arg Ser Thr Thr Lys
                 95                 100                 105

Thr Ser Gly Pro

<210> SEQ ID NO 2
<211> LENGTH: 111
<212> TYPE: PRT
<213> ORGANISM: Mus musculus

<400> SEQUENCE: 2

Asp Ile Val Leu Thr Gln Ser Pro Ala Ser Leu Ala Val Ser Leu
  1               5                  10                  15

Gly Gln Arg Ala Thr Ile Ser Cys Lys Ala Ser Gln Ser Val Asp
                 20                  25                  30
```

Tyr Asp Gly Asp Ser Tyr Met Asn Trp Tyr Gln Gln Lys Pro Gly
                35                  40                  45

Gln Pro Pro Ile Leu Leu Ile Tyr Ala Ala Ser Tyr Leu Gly Ser
            50                  55                  60

Glu Ile Pro Ala Arg Phe Ser Gly Ser Gly Ser Gly Thr Asp Phe
            65                  70                  75

Thr Leu Asn Ile His Pro Val Glu Glu Asp Ala Ala Thr Phe
            80                  85                  90

Tyr Cys Gln Gln Ser His Glu Asp Pro Tyr Thr Phe Gly Ala Gly
            95                  100                 105

Thr Lys Leu Glu Ile Lys
            110

<210> SEQ ID NO 3
<211> LENGTH: 134
<212> TYPE: PRT
<213> ORGANISM: Mus musculus

<400> SEQUENCE: 3

Asp Val Gln Leu Gln Glu Ser Gly Pro Gly Leu Val Lys Pro Ser
 1               5                  10                  15

Gln Ser Leu Ser Leu Ala Cys Ser Val Thr Gly Tyr Ser Ile Thr
                20                  25                  30

Ser Gly Tyr Ser Trp Asn Trp Ile Arg Gln Phe Pro Gly Asn Lys
            35                  40                  45

Leu Glu Trp Met Gly Ser Ile Thr Tyr Asp Gly Ser Ser Asn Tyr
            50                  55                  60

Asn Pro Ser Leu Lys Asn Arg Ile Ser Val Thr Arg Asp Thr Ser
            65                  70                  75

Gln Asn Gln Phe Phe Leu Lys Leu Asn Ser Ala Thr Ala Glu Asp
            80                  85                  90

Thr Ala Thr Tyr Tyr Cys Ala Arg Gly Ser His Tyr Phe Gly His
            95                  100                 105

Trp His Phe Ala Val Trp Gly Ala Gly Thr Thr Val Thr Val Ser
            110                 115                 120

Ser Ala Lys Thr Thr Pro Pro Ser Val Tyr Pro Leu Ala Arg
            125                 130

<210> SEQ ID NO 4
<211> LENGTH: 124
<212> TYPE: PRT
<213> ORGANISM: Mus musculus

<400> SEQUENCE: 4

Asp Ile Val Met Thr Gln Ser Gln Lys Phe Met Ser Thr Ser Val
 1               5                  10                  15

Gly Asp Arg Val Ser Val Thr Cys Lys Ala Ser Gln Asn Val Ser
                20                  25                  30

Ser Asn Val Ala Trp Tyr Gln Gln Lys Pro Gly Gln Ser Pro Lys
            35                  40                  45

Ala Leu Ile Tyr Ser Ala Ser Tyr Arg Tyr Ser Gly Val Pro Asp
            50                  55                  60

Arg Phe Thr Gly Ser Gly Ser Gly Thr Asp Phe Thr Leu Thr Ile
            65                  70                  75

Ser Asn Val Gln Ser Glu Asp Leu Ala Glu Tyr Phe Cys Gln Gln
            80                  85                  90

```
Tyr Tyr Thr Tyr Pro Leu Tyr Thr Phe Gly Gly Gly Thr Lys Leu
                 95                 100                 105

Glu Ile Lys Arg Ala Asp Ala Ala Pro Thr Val Ser Ile Phe Pro
                110                 115                 120

Pro Ser Thr Arg

<210> SEQ ID NO 5
<211> LENGTH: 130
<212> TYPE: PRT
<213> ORGANISM: Mus musculus

<400> SEQUENCE: 5

Asp Val Gln Leu Gln Glu Ser Gly Pro Gly Leu Val Lys Pro Ser
 1               5                  10                  15

Gln Ser Leu Ser Leu Thr Cys Thr Val Thr Gly Tyr Thr Ile Thr
                20                  25                  30

Ser Asp Asn Ala Trp Asn Trp Ile Arg Gln Phe Pro Gly Asn Lys
                35                  40                  45

Leu Glu Trp Met Gly Tyr Ile Asn His Ser Gly Thr Thr Ser Tyr
                50                  55                  60

Asn Pro Ser Leu Lys Ser Arg Ile Ser Ile Thr Arg Asp Thr Ser
                65                  70                  75

Lys Asn Gln Phe Phe Leu Gln Leu Asn Ser Val Thr Thr Glu Asp
                80                  85                  90

Thr Ala Thr Tyr Tyr Cys Ala Trp Val Val Ala Tyr Ala Met Asp
                95                  100                 105

Tyr Trp Gly Gln Gly Thr Ser Val Thr Val Ser Ser Ala Lys Thr
                110                 115                 120

Thr Pro Pro Ser Val Tyr Pro Leu Ala Arg
                125                 130

<210> SEQ ID NO 6
<211> LENGTH: 106
<212> TYPE: PRT
<213> ORGANISM: Mus musculus

<400> SEQUENCE: 6

Asp Ile Gln Leu Thr Gln Ser Pro Ala Ser Leu Ala Val Ser Leu
 1               5                  10                  15

Gly Gln Arg Ala Thr Ile Ser Cys Lys Ala Ser Gln Ser Val Asp
                20                  25                  30

Tyr Asp Gly Asp Ser Tyr Met Asn Trp Tyr Gln Gln Lys Pro Gly
                35                  40                  45

Gln Pro Pro Lys Leu Leu Ile Tyr Ala Ala Ser Asn Leu Glu Ser
                50                  55                  60

Gly Ile Pro Ala Arg Phe Ser Gly Ser Gly Ser Gly Thr Asp Phe
                65                  70                  75

Thr Leu Asn Ile His Pro Val Glu Glu Glu Asp Ala Ala Thr Tyr
                80                  85                  90

Tyr Cys Gln Gln Ser Asn Glu Asp Pro Phe Thr Phe Gly Ala Gly
                95                  100                 105

Thr

<210> SEQ ID NO 7
<211> LENGTH: 137
<212> TYPE: PRT
```

-continued

<213> ORGANISM: Mus musculus

<400> SEQUENCE: 7

```
Asp Val Gln His Gln Glu Ser Glu Pro Asp Leu Val Lys Pro Ser
  1               5                  10                  15

Gln Ser Leu Ser Leu Thr Cys Thr Val Thr Gly Tyr Ser Ile Thr
                 20                  25                  30

Ser Gly Tyr Asn Arg His Trp Ile Arg Gln Phe Pro Gly Asn Lys
                 35                  40                  45

Leu Glu Trp Met Gly Tyr Ile His Tyr Ser Gly Ser Thr Asn Tyr
                 50                  55                  60

Asn Pro Ser Leu Lys Arg Arg Ile Ser Ile Thr Arg Asp Thr Ser
                 65                  70                  75

Lys Asn Gln Phe Phe Leu Gln Leu Asn Ser Val Thr Thr Glu Asp
                 80                  85                  90

Thr Ala Thr Tyr Tyr Cys Ala Arg Gly Ser Ile Tyr Tyr Tyr Gly
                 95                 100                 105

Ser Arg Tyr Arg Tyr Phe Asp Val Trp Gly Ala Gly Thr Thr Val
                110                 115                 120

Thr Val Ser Ser Ala Lys Arg His Pro His Leu Ser Ile His Trp
                125                 130                 135

Pro Gly
```

<210> SEQ ID NO 8
<211> LENGTH: 453
<212> TYPE: PRT
<213> ORGANISM: Artificial Sequence
<220> FEATURE:
<223> OTHER INFORMATION: humanized mae11, version 1 heavy chain

<400> SEQUENCE: 8

```
Glu Val Gln Leu Val Glu Ser Gly Gly Gly Leu Val Gln Pro Gly
  1               5                  10                  15

Gly Ser Leu Arg Leu Ser Cys Ala Val Ser Gly Tyr Ser Ile Thr
                 20                  25                  30

Ser Gly Tyr Ser Trp Asn Trp Ile Arg Gln Ala Pro Gly Lys Gly
                 35                  40                  45

Leu Glu Trp Val Ala Ser Ile Thr Tyr Asp Gly Ser Thr Asn Tyr
                 50                  55                  60

Ala Asp Ser Val Lys Gly Arg Phe Thr Ile Ser Arg Asp Asp Ser
                 65                  70                  75

Lys Asn Thr Phe Tyr Leu Gln Met Asn Ser Leu Arg Ala Glu Asp
                 80                  85                  90

Thr Ala Val Tyr Tyr Cys Ala Arg Gly Ser His Tyr Phe Gly His
                 95                 100                 105

Trp His Phe Ala Val Trp Gly Gln Gly Thr Leu Val Thr Val Ser
                110                 115                 120

Ser Ala Ser Thr Lys Gly Lys Gly Pro Ser Val Phe Pro Leu Ala
                125                 130                 135

Pro Ser Ser Lys Ser Thr Ser Gly Gly Thr Ala Ala Leu Gly Cys
                140                 145                 150

Leu Val Lys Asp Tyr Phe Pro Glu Pro Val Thr Val Ser Trp Asn
                155                 160                 165

Ser Gly Ala Leu Thr Ser Gly Val His Thr Phe Pro Ala Val Leu
                170                 175                 180
```

Gln Ser Ser Gly Leu Tyr Ser Leu Ser Val Val Thr Val Pro
                185                 190                 195

Ser Ser Ser Leu Gly Thr Gln Thr Tyr Ile Cys Asn Val Asn His
                200                 205                 210

Lys Pro Ser Asn Thr Lys Val Asp Lys Val Glu Pro Lys Ser
            215                 220                 225

Cys Asp Lys Thr His Thr Cys Pro Pro Cys Pro Ala Pro Glu Leu
                230                 235                 240

Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val
                275                 280                 285

Asp Gly Val Glu Val His Asn Ala Lys Thr Lys Pro Arg Glu Glu
                290                 295                 300

Gln Tyr Asn Ser Thr Tyr Arg Val Val Ser Val Leu Thr Val Leu
                305                 310                 315

His Gln Asp Trp Leu Asn Gly Lys Glu Tyr Lys Cys Lys Val Ser
                320                 325                 330

Asn Lys Ala Leu Pro Ala Pro Ile Glu Lys Thr Ile Ser Lys Ala
                335                 340                 345

Lys Gly Gln Pro Arg Glu Pro Gln Val Tyr Thr Leu Pro Pro Ser
                350                 355                 360

Arg Glu Glu Met Thr Lys Asn Gln Val Ser Leu Thr Cys Leu Val
                365                 370                 375

Lys Gly Phe Tyr Pro Ser Asp Ile Ala Val Glu Trp Glu Ser Asn
                380                 385                 390

Gly Gln Pro Glu Asn Asn Tyr Lys Thr Thr Pro Pro Val Leu Asp
                395                 400                 405

Ser Asp Gly Ser Phe Phe Leu Tyr Ser Lys Leu Thr Val Asp Lys
                410                 415                 420

Ser Arg Trp Gln Gln Gly Asn Val Phe Ser Cys Ser Val Met His
                425                 430                 435

Glu Ala Leu His Asn His Tyr Thr Gln Lys Ser Leu Ser Leu Ser
                440                 445                 450

Pro Gly Lys

<210> SEQ ID NO 9
<211> LENGTH: 218
<212> TYPE: PRT
<213> ORGANISM: Artificial Sequence
<220> FEATURE:
<223> OTHER INFORMATION: humanized maell, version 1, light chain

<400> SEQUENCE: 9

Asp Ile Gln Leu Thr Gln Ser Pro Ser Ser Leu Ser Ala Ser Val
 1               5                  10                  15

Gly Asp Arg Val Thr Ile Thr Cys Arg Ala Ser Gln Ser Val Asp
                20                  25                  30

Tyr Asp Gly Asp Ser Tyr Met Asn Trp Tyr Gln Gln Lys Pro Gly
                35                  40                  45

Lys Ala Pro Lys Leu Leu Ile Tyr Ala Ala Ser Tyr Leu Glu Ser
                50                  55                  60

Gly Val Pro Ser Arg Phe Ser Gly Ser Gly Ser Gly Thr Asp Phe

-continued

```
                 65                  70                  75
Thr Leu Thr Ile Ser Ser Leu Gln Pro Glu Asp Phe Ala Thr Tyr
             80                  85                  90
Tyr Cys Gln Gln Ser His Glu Asp Pro Tyr Thr Phe Gly Gln Gly
         95                 100                 105
Thr Lys Val Glu Ile Lys Arg Thr Val Ala Ala Pro Ser Val Phe
     110                 115                 120
Ile Phe Pro Pro Ser Asp Glu Gln Leu Lys Ser Gly Thr Ala Ser
 125                 130                 135
Val Val Cys Leu Leu Asn Asn Phe Tyr Pro Arg Glu Ala Lys Val
             140                 145                 150
Gln Trp Lys Val Asp Asn Ala Leu Gln Ser Gly Asn Ser Gln Glu
         155                 160                 165
Ser Val Thr Glu Gln Asp Ser Lys Asp Ser Thr Tyr Ser Leu Ser
     170                 175                 180
Ser Thr Leu Thr Leu Ser Lys Ala Asp Tyr Glu Lys His Lys Val
 185                 190                 195
Tyr Ala Cys Glu Val Thr His Gln Gly Leu Ser Ser Pro Val Thr
             200                 205                 210
Lys Ser Phe Asn Arg Gly Glu Cys
         215
```

```
<210> SEQ ID NO 10
<211> LENGTH: 8
<212> TYPE: PRT
<213> ORGANISM: Homo sapiens

<400> SEQUENCE: 10

Phe Asp Leu Phe Ile Arg Lys Ser
 1               5

<210> SEQ ID NO 11
<211> LENGTH: 9
<212> TYPE: PRT
<213> ORGANISM: Homo sapiens

<400> SEQUENCE: 11

Lys Asp Thr Leu Met Ile Ser Arg Thr
 1               5

<210> SEQ ID NO 12
<211> LENGTH: 6
<212> TYPE: PRT
<213> ORGANISM: Homo sapiens

<400> SEQUENCE: 12

Ala Pro Ser Lys Gly Thr
 1               5

<210> SEQ ID NO 13
<211> LENGTH: 6
<212> TYPE: PRT
<213> ORGANISM: Homo sapiens

<400> SEQUENCE: 13

Ser His Glu Asp Pro Gln
 1               5

<210> SEQ ID NO 14
<211> LENGTH: 11
```

```
<212> TYPE: PRT
<213> ORGANISM: Homo sapiens

<400> SEQUENCE: 14

Ser Arg Ala Ser Gly Lys Pro Val Asn His Ser
1               5                   10

<210> SEQ ID NO 15
<211> LENGTH: 11
<212> TYPE: PRT
<213> ORGANISM: Homo sapiens

<400> SEQUENCE: 15

Tyr Val Asp Gly Val Gln Val His Asn Ala Lys
1               5                   10

<210> SEQ ID NO 16
<211> LENGTH: 10
<212> TYPE: PRT
<213> ORGANISM: Homo sapiens

<400> SEQUENCE: 16

Gly Thr Arg Asp Trp Ile Glu Gly Glu Thr
1               5                   10

<210> SEQ ID NO 17
<211> LENGTH: 10
<212> TYPE: PRT
<213> ORGANISM: Homo sapiens

<400> SEQUENCE: 17

Leu His Gln Asp Trp Leu Asp Gly Lys Glu
1               5                   10

<210> SEQ ID NO 18
<211> LENGTH: 4
<212> TYPE: PRT
<213> ORGANISM: Homo sapiens

<400> SEQUENCE: 18

Arg Ala Leu Met
1

<210> SEQ ID NO 19
<211> LENGTH: 4
<212> TYPE: PRT
<213> ORGANISM: Homo sapiens

<400> SEQUENCE: 19

Ala Pro Ile Glu
1

<210> SEQ ID NO 20
<211> LENGTH: 6
<212> TYPE: PRT
<213> ORGANISM: Homo sapiens

<400> SEQUENCE: 20

Lys Glu Glu Lys Gln Arg
1               5

<210> SEQ ID NO 21
<211> LENGTH: 6
<212> TYPE: PRT
<213> ORGANISM: Homo sapiens
```

```
<400> SEQUENCE: 21

Pro Arg Glu Gln Gln Tyr
 1               5

<210> SEQ ID NO 22
<211> LENGTH: 5
<212> TYPE: PRT
<213> ORGANISM: Homo sapiens

<400> SEQUENCE: 22

Gln Cys Arg Val Thr
 1               5

<210> SEQ ID NO 23
<211> LENGTH: 5
<212> TYPE: PRT
<213> ORGANISM: Artificial Sequence
<220> FEATURE:
<223> OTHER INFORMATION: Modified IgG1-derived sequence

<400> SEQUENCE: 23

Ala Cys Ala Val Ala
 1               5

<210> SEQ ID NO 24
<211> LENGTH: 8
<212> TYPE: PRT
<213> ORGANISM: Homo sapiens

<400> SEQUENCE: 24

Gln Lys His Trp Leu Ser Asp Arg
 1               5

<210> SEQ ID NO 25
<211> LENGTH: 8
<212> TYPE: PRT
<213> ORGANISM: Artificial Sequence
<220> FEATURE:
<223> OTHER INFORMATION: Modified IgG1-derived sequence

<400> SEQUENCE: 25

Ala Ala Ala Trp Leu Ala Ala Ala
 1               5

<210> SEQ ID NO 26
<211> LENGTH: 4
<212> TYPE: PRT
<213> ORGANISM: Mus musculus

<400> SEQUENCE: 26

Tyr Asp Gly Asp
 1

<210> SEQ ID NO 27
<211> LENGTH: 8
<212> TYPE: PRT
<213> ORGANISM: Homo sapiens

<400> SEQUENCE: 27

Phe Asp Leu Phe Ile Arg Lys Ser
 1               5

<210> SEQ ID NO 28
<211> LENGTH: 9
```

```
<212> TYPE: PRT
<213> ORGANISM: Homo sapiens

<400> SEQUENCE: 28

Lys Asp Thr Leu Met Ile Ser Arg Thr
 1               5

<210> SEQ ID NO 29
<211> LENGTH: 4
<212> TYPE: PRT
<213> ORGANISM: Homo sapiens

<400> SEQUENCE: 29

Phe Asp Leu Phe
 1

<210> SEQ ID NO 30
<211> LENGTH: 4
<212> TYPE: PRT
<213> ORGANISM: Artificial Sequence
<220> FEATURE:
<223> OTHER INFORMATION: Mutant IgE Fc(epsilon)3 sequence fragment

<400> SEQUENCE: 30

Gln Asp Leu His
 1

<210> SEQ ID NO 31
<211> LENGTH: 6
<212> TYPE: PRT
<213> ORGANISM: Homo sapiens

<400> SEQUENCE: 31

Ala Pro Ser Lys Gly Thr
 1               5

<210> SEQ ID NO 32
<211> LENGTH: 6
<212> TYPE: PRT
<213> ORGANISM: Homo sapiens

<400> SEQUENCE: 32

Ser His Glu Asp Pro Gln
 1               5

<210> SEQ ID NO 33
<211> LENGTH: 11
<212> TYPE: PRT
<213> ORGANISM: Homo sapiens

<400> SEQUENCE: 33

Ser Arg Ala Ser Gly Lys Pro Val Asn His Ser
 1               5                   10

<210> SEQ ID NO 34
<211> LENGTH: 11
<212> TYPE: PRT
<213> ORGANISM: Homo sapiens

<400> SEQUENCE: 34

Tyr Val Asp Gly Val Gln Val His Asn Ala Lys
 1               5                   10

<210> SEQ ID NO 35
<211> LENGTH: 6
```

```
<212> TYPE: PRT
<213> ORGANISM: Homo sapiens

<400> SEQUENCE: 35

Ser Arg Ala Ser Gly Lys
 1               5

<210> SEQ ID NO 36
<211> LENGTH: 6
<212> TYPE: PRT
<213> ORGANISM: Artificial Sequence
<220> FEATURE:
<223> OTHER INFORMATION: Mutant IgE Fc(epsilon)3 sequence fragment

<400> SEQUENCE: 36

Ala Ala Ala Ala Gly Ala
 1               5

<210> SEQ ID NO 37
<211> LENGTH: 6
<212> TYPE: PRT
<213> ORGANISM: Homo sapiens

<400> SEQUENCE: 37

Lys Glu Glu Lys Gln Arg
 1               5

<210> SEQ ID NO 38
<211> LENGTH: 6
<212> TYPE: PRT
<213> ORGANISM: Homo sapiens

<400> SEQUENCE: 38

Pro Arg Glu Gln Gln Tyr
 1               5

<210> SEQ ID NO 39
<211> LENGTH: 6
<212> TYPE: PRT
<213> ORGANISM: Homo sapeins

<400> SEQUENCE: 39

Lys Glu Glu Lys Gln Arg
 1               5

<210> SEQ ID NO 40
<211> LENGTH: 6
<212> TYPE: PRT
<213> ORGANISM: Artificial Sequence
<220> FEATURE:
<223> OTHER INFORMATION: Mutant sequence substituted in place
      of IgE Fc(epsilon)3 fragment

<400> SEQUENCE: 40

Ala Glu Ala Lys Ala Arg
 1               5

<210> SEQ ID NO 41
<211> LENGTH: 6
<212> TYPE: PRT
<213> ORGANISM: Homo sapiens

<400> SEQUENCE: 41

Lys Glu Glu Lys Gln Arg
 1               5
```

```
<210> SEQ ID NO 42
<211> LENGTH: 6
<212> TYPE: PRT
<213> ORGANISM: Artificial Sequence
<220> FEATURE:
<223> OTHER INFORMATION: Mutant sequence substituted in place of
      IgE Fc(epsilon)3 fragment

<400> SEQUENCE: 42

Lys Ala Glu Ala Gln Ala
 1               5

<210> SEQ ID NO 43
<211> LENGTH: 6
<212> TYPE: PRT
<213> ORGANISM: Homo sapiens

<400> SEQUENCE: 43

Lys Glu Glu Lys Gln Arg
 1               5

<210> SEQ ID NO 44
<211> LENGTH: 6
<212> TYPE: PRT
<213> ORGANISM: Artificial Sequence
<220> FEATURE:
<223> OTHER INFORMATION: Mutant sequence substituted in place of IgE
      Fc(epsilon)3 fragment

<400> SEQUENCE: 44

Ala Ala Glu Ala Gln Ala
 1               5

<210> SEQ ID NO 45
<211> LENGTH: 10
<212> TYPE: PRT
<213> ORGANISM: Homo sapiens

<400> SEQUENCE: 45

Gly Thr Arg Asp Trp Ile Glu Gly Glu Thr
 1               5                  10

<210> SEQ ID NO 46
<211> LENGTH: 10
<212> TYPE: PRT
<213> ORGANISM: Artificial Sequence
<220> FEATURE:
<223> OTHER INFORMATION: Mutant sequence substituted in place of IgE
      Fc(epsilon)3 fragment

<400> SEQUENCE: 46

Leu His Gln Asp Trp Leu Asp Gly Lys Glu
 1               5                  10

<210> SEQ ID NO 47
<211> LENGTH: 4
<212> TYPE: PRT
<213> ORGANISM: Homo sapiens

<400> SEQUENCE: 47

Glu Gly Glu Thr
 1

<210> SEQ ID NO 48
<211> LENGTH: 4
<212> TYPE: PRT
```

```
<213> ORGANISM: Artificial Sequence
<220> FEATURE:
<223> OTHER INFORMATION: Mutant sequence substituted in place of IgE
      Fc(epsilon)3 fragment

<400> SEQUENCE: 48

Ala Gly Ala Ala
  1

<210> SEQ ID NO 49
<211> LENGTH: 9
<212> TYPE: PRT
<213> ORGANISM: Homo sapiens

<400> SEQUENCE: 49

Thr Arg Asp Trp Ile Glu Gly Glu Thr
  1               5

<210> SEQ ID NO 50
<211> LENGTH: 9
<212> TYPE: PRT
<213> ORGANISM: Artificial Sequence
<220> FEATURE:
<223> OTHER INFORMATION: Mutant sequence substituted in place of IgE
      Fc(epsilon)3 fragment

<400> SEQUENCE: 50

His Gln Asp Trp Leu Asp Gly Lys Glu
  1               5

<210> SEQ ID NO 51
<211> LENGTH: 4
<212> TYPE: PRT
<213> ORGANISM: Homo sapiens

<400> SEQUENCE: 51

Glu Gly Glu Thr
  1

<210> SEQ ID NO 52
<211> LENGTH: 4
<212> TYPE: PRT
<213> ORGANISM: Artificial Sequence
<220> FEATURE:
<223> OTHER INFORMATION: Mutant sequence substituted in place of IgE
      Fc(epsilon)3 fragment

<400> SEQUENCE: 52

Asp Gly Lys Glu
  1

<210> SEQ ID NO 53
<211> LENGTH: 5
<212> TYPE: PRT
<213> ORGANISM: Homo sapiens

<400> SEQUENCE: 53

Gln Cys Arg Val Thr
  1               5

<210> SEQ ID NO 54
<211> LENGTH: 5
<212> TYPE: PRT
<213> ORGANISM: Artificial Sequence
<220> FEATURE:
<223> OTHER INFORMATION: Mutant sequence substituted in place of IgE
      Fc(epsilon)3 fragment
```

```
<400> SEQUENCE: 54

Ala Cys Ala Val Ala
  1               5

<210> SEQ ID NO 55
<211> LENGTH: 4
<212> TYPE: PRT
<213> ORGANISM: Homo sapiens

<400> SEQUENCE: 55

Arg Ala Leu Met
  1

<210> SEQ ID NO 56
<211> LENGTH: 4
<212> TYPE: PRT
<213> ORGANISM: Artificial Sequence
<220> FEATURE:
<223> OTHER INFORMATION: Mutant sequence substituted in place of IgE
      Fc(epsilon)3 fragment

<400> SEQUENCE: 56

Ala Pro Ile Glu
  1

<210> SEQ ID NO 57
<211> LENGTH: 8
<212> TYPE: PRT
<213> ORGANISM: Homo sapiens

<400> SEQUENCE: 57

Gln Lys His Trp Leu Ser Asp Arg
  1               5

<210> SEQ ID NO 58
<211> LENGTH: 8
<212> TYPE: PRT
<213> ORGANISM: Artificial Sequence
<220> FEATURE:
<223> OTHER INFORMATION: Mutant sequence substituted in place of IgE
      Fc(epsilon)e fragment

<400> SEQUENCE: 58

Ala Ala Ala Trp Leu Ala Ala Ala
  1               5

<210> SEQ ID NO 59
<211> LENGTH: 4
<212> TYPE: PRT
<213> ORGANISM: Homo sapiens

<400> SEQUENCE: 59

Pro Arg Ala Ala
  1

<210> SEQ ID NO 60
<211> LENGTH: 4
<212> TYPE: PRT
<213> ORGANISM: Artificial Sequence
<220> FEATURE:
<223> OTHER INFORMATION: Mutant sequence substituted in place of IgE
      Fc(epsilon)3 fragment

<400> SEQUENCE: 60

Gln Pro Arg Glu
```

-continued

<210> SEQ ID NO 61
<211> LENGTH: 6
<212> TYPE: PRT
<213> ORGANISM: Homo sapiens

<400> SEQUENCE: 61

Ala Ser Pro Ser Gln Thr
 1               5

<210> SEQ ID NO 62
<211> LENGTH: 5
<212> TYPE: PRT
<213> ORGANISM: Artificial Sequence
<220> FEATURE:
<223> OTHER INFORMATION: Mutant sequence substituted in place of IgE
      Fc(epsilon)3 fragment

<400> SEQUENCE: 62

Leu His Asn His Tyr
 1               5

<210> SEQ ID NO 63
<211> LENGTH: 5
<212> TYPE: PRT
<213> ORGANISM: Homo sapiens

<400> SEQUENCE: 63

Ser Pro Ser Gln Thr
 1               5

<210> SEQ ID NO 64
<211> LENGTH: 5
<212> TYPE: PRT
<213> ORGANISM: Homo sapiens

<400> SEQUENCE: 64

Ala Pro Ala Ala Ala
 1               5

<210> SEQ ID NO 65
<211> LENGTH: 451
<212> TYPE: PRT
<213> ORGANISM: Artificial Sequence
<220> FEATURE:
<223> OTHER INFORMATION: Full-length heavy chain sequence corresponding
      to F(ab)8b of Table 9

<400> SEQUENCE: 65

Glu Val Gln Leu Val Glu Ser Gly Gly Gly Leu Val Gln Pro Gly
 1               5                  10                  15

Gly Ser Leu Arg Leu Ser Cys Ala Val Ser Gly Tyr Ser Ile Thr
                20                  25                  30

Ser Gly Tyr Ser Trp Asn Trp Ile Arg Gln Ala Pro Gly Lys Gly
                35                  40                  45

Leu Glu Trp Val Ala Ser Ile Thr Tyr Asp Gly Ser Thr Asn Tyr
                50                  55                  60

Asn Pro Ser Val Lys Gly Arg Ile Thr Ile Ser Arg Asp Asp Ser
                65                  70                  75

Lys Asn Thr Phe Tyr Leu Gln Met Asn Ser Leu Arg Ala Glu Asp
                80                  85                  90

Thr Ala Val Tyr Tyr Cys Ala Arg Gly Ser His Tyr Phe Gly His

-continued

```
                 95                 100                 105
Trp His Phe Ala Val Trp Gly Gln Gly Thr Leu Val Thr Val Ser
            110                 115                 120

Ser Ala Ser Thr Lys Gly Pro Ser Val Phe Pro Leu Ala Pro Ser
            125                 130                 135

Ser Lys Ser Thr Ser Gly Gly Thr Ala Ala Leu Gly Cys Leu Val
            140                 145                 150

Lys Asp Tyr Phe Pro Glu Pro Val Thr Val Ser Trp Asn Ser Gly
            155                 160                 165

Ala Leu Thr Ser Gly Val His Thr Phe Pro Ala Val Leu Gln Ser
            170                 175                 180

Ser Gly Leu Tyr Ser Leu Ser Ser Val Val Thr Val Pro Ser Ser
            185                 190                 195

Ser Leu Gly Thr Gln Thr Tyr Ile Cys Asn Val Asn His Lys Pro
            200                 205                 210

Ser Asn Thr Lys Val Asp Lys Lys Val Glu Pro Lys Ser Cys Asp
            215                 220                 225

Lys Thr His Thr Cys Pro Pro Cys Pro Ala Pro Glu Leu Leu Gly
            230                 235                 240

Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln
            305                 310                 315

Asp Trp Leu Asn Gly Lys Glu Tyr Lys Cys Lys Val Ser Asn Lys
            320                 325                 330

Ala Leu Pro Ala Pro Ile Glu Lys Thr Ile Ser Lys Ala Lys Gly
            335                 340                 345

Gln Pro Arg Glu Pro Gln Val Tyr Thr Leu Pro Pro Ser Arg Glu
            350                 355                 360

Glu Met Thr Lys Asn Gln Val Ser Leu Thr Cys Leu Val Lys Gly
            365                 370                 375

Phe Tyr Pro Ser Asp Ile Ala Val Glu Trp Glu Ser Asn Gly Gln
            380                 385                 390

Pro Glu Asn Asn Tyr Lys Thr Thr Pro Pro Val Leu Asp Ser Asp
            395                 400                 405

Gly Ser Phe Phe Leu Tyr Ser Lys Leu Thr Val Asp Lys Ser Arg
            410                 415                 420

Trp Gln Gln Gly Asn Val Phe Ser Cys Ser Val Met His Glu Ala
            425                 430                 435

Leu His Asn His Tyr Thr Gln Lys Ser Leu Ser Leu Ser Pro Gly
            440                 445                 450

Lys

<210> SEQ ID NO 66
<211> LENGTH: 451
<212> TYPE: PRT
<213> ORGANISM: Artificial Sequence
<220> FEATURE:
```

<223> OTHER INFORMATION: Full-length heavy chain sequence corresponding to F(ab)8a of Table 9

<400> SEQUENCE: 66

```
Glu Val Gln Leu Val Glu Ser Gly Gly Gly Leu Val Gln Pro Gly
 1               5                  10                  15

Gly Ser Leu Arg Leu Ser Cys Ala Val Ser Gly Tyr Ser Ile Thr
             20                  25                  30

Ser Gly Tyr Ser Trp Asn Trp Ile Arg Gln Ala Pro Gly Lys Gly
         35                  40                  45

Leu Glu Trp Val Ala Ser Ile Thr Tyr Asp Gly Ser Thr Asn Tyr
     50                  55                  60

Asn Pro Ser Leu Lys Gly Arg Ile Thr Ile Ser Arg Asp Asp Ser
 65                  70                  75

Lys Asn Thr Phe Tyr Leu Gln Met Asn Ser Leu Arg Ala Glu Asp
             80                  85                  90

Thr Ala Val Tyr Tyr Cys Ala Arg Gly Ser His Tyr Phe Gly His
         95                 100                 105

Trp His Phe Ala Val Trp Gly Gln Gly Thr Leu Val Thr Val Ser
    110                 115                 120

Ser Ala Ser Thr Lys Gly Pro Ser Val Phe Pro Leu Ala Pro Ser
125                 130                 135

Ser Lys Ser Thr Ser Gly Gly Thr Ala Ala Leu Gly Cys Leu Val
            140                 145                 150

Lys Asp Tyr Phe Pro Glu Pro Val Thr Val Ser Trp Asn Ser Gly
        155                 160                 165

Ala Leu Thr Ser Gly Val His Thr Phe Pro Ala Val Leu Gln Ser
    170                 175                 180

Ser Gly Leu Tyr Ser Leu Ser Ser Val Val Thr Val Pro Ser Ser
185                 190                 195

Ser Leu Gly Thr Gln Thr Tyr Ile Cys Asn Val Asn His Lys Pro
            200                 205                 210

Ser Asn Thr Lys Val Asp Lys Lys Val Glu Pro Lys Ser Cys Asp
        215                 220                 225

Lys Thr His Thr Cys Pro Pro Cys Pro Ala Pro Glu Leu Leu Gly
    230                 235                 240

Gly Pro Ser Val Phe Leu Phe Pro Pro Lys Pro Lys Asp Thr Leu
245                 250                 255

Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln
305                 310                 315

Asp Trp Leu Asn Gly Lys Glu Tyr Lys Cys Lys Val Ser Asn Lys
            320                 325                 330

Ala Leu Pro Ala Pro Ile Glu Lys Thr Ile Ser Lys Ala Lys Gly
        335                 340                 345

Gln Pro Arg Glu Pro Gln Val Tyr Thr Leu Pro Pro Ser Arg Glu
    350                 355                 360

Glu Met Thr Lys Asn Gln Val Ser Leu Thr Cys Leu Val Lys Gly
365                 370                 375
```

```
Phe Tyr Pro Ser Asp Ile Ala Val Glu Trp Glu Ser Asn Gly Gln
                380                 385                 390

Pro Glu Asn Asn Tyr Lys Thr Thr Pro Pro Val Leu Asp Ser Asp
            395                 400                 405

Gly Ser Phe Phe Leu Tyr Ser Lys Leu Thr Val Asp Lys Ser Arg
        410                 415                 420

Trp Gln Gln Gly Asn Val Phe Ser Cys Ser Val Met His Glu Ala
    425                 430                 435

Leu His Asn His Tyr Thr Gln Lys Ser Leu Ser Leu Ser Pro Gly
                440                 445                 450

Lys

<210> SEQ ID NO 67
<211> LENGTH: 218
<212> TYPE: PRT
<213> ORGANISM: Artificial Sequence
<220> FEATURE:
<223> OTHER INFORMATION: Full-length light chain sequence corresponding
      to F(ab)9 of Table 9

<400> SEQUENCE: 67

Asp Ile Gln Leu Thr Gln Ser Pro Ser Ser Leu Ser Val Ser Val
 1               5                  10                  15

Gly Asp Arg Ala Thr Ile Thr Cys Arg Ala Ser Gln Ser Val Asp
                20                  25                  30

Tyr Asp Gly Asp Ser Tyr Met Asn Trp Tyr Gln Gln Lys Pro Gly
            35                  40                  45

Lys Ala Pro Lys Leu Leu Ile Tyr Ala Ala Ser Tyr Leu Glu Ser
        50                  55                  60

Gly Ile Pro Ser Arg Phe Ser Gly Ser Gly Ser Gly Thr Asp Phe
    65                  70                  75

Thr Leu Thr Ile Ser Ser Val Gln Pro Glu Asp Phe Ala Thr Tyr
                80                  85                  90

Tyr Cys Gln Gln Ser His Glu Asp Pro Tyr Thr Phe Gly Gln Gly
            95                  100                 105

Thr Lys Leu Glu Ile Lys Arg Thr Val Ala Ala Pro Ser Val Phe
        110                 115                 120

Ile Phe Pro Pro Ser Asp Glu Gln Leu Lys Ser Gly Thr Ala Ser
    125                 130                 135

Val Val Cys Leu Leu Asn Asn Phe Tyr Pro Arg Glu Ala Lys Val
                140                 145                 150

Gln Trp Lys Val Asp Asn Ala Leu Gln Ser Gly Asn Ser Gln Glu
            155                 160                 165

Ser Val Thr Glu Gln Asp Ser Lys Asp Ser Thr Tyr Ser Leu Ser
        170                 175                 180

Ser Thr Leu Thr Leu Ser Lys Ala Asp Tyr Glu Lys His Lys Val
    185                 190                 195

Tyr Ala Cys Glu Val Thr His Gln Gly Leu Ser Ser Pro Val Thr
                200                 205                 210

Lys Ser Phe Asn Arg Gly Glu Cys
            215

<210> SEQ ID NO 68
<211> LENGTH: 451
<212> TYPE: PRT
<213> ORGANISM: Artificial Sequence
```

```
<220> FEATURE:
<223> OTHER INFORMATION: Full-length heavy chain sequence corresponding
      to F(ab)9 of Table 9

<400> SEQUENCE: 68

Glu Val Gln Leu Val Glu Ser Gly Gly Gly Leu Val Gln Pro Gly
  1               5                  10                  15

Gly Ser Leu Arg Leu Ser Cys Ala Val Ser Gly Tyr Ser Ile Thr
                 20                  25                  30

Ser Gly Tyr Ser Trp Asn Trp Ile Arg Gln Ala Pro Gly Lys Gly
                 35                  40                  45

Leu Glu Trp Met Gly Ser Ile Thr Tyr Asp Gly Ser Thr Asn Tyr
                 50                  55                  60

Asn Asp Ser Leu Lys Gly Arg Ile Thr Val Ser Arg Asp Asp Ser
                 65                  70                  75

Lys Asn Thr Phe Tyr Leu Gln Leu Asn Ser Ala Arg Ala Glu Asp
                 80                  85                  90

Thr Ala Val Tyr Tyr Cys Ala Arg Gly Ser His Tyr Phe Gly His
                 95                 100                 105

Trp His Phe Ala Val Trp Gly Gln Gly Thr Leu Val Thr Val Ser
                110                 115                 120

Ser Ala Ser Thr Lys Gly Pro Ser Val Phe Pro Leu Ala Pro Ser
                125                 130                 135

Ser Lys Ser Thr Ser Gly Gly Thr Ala Ala Leu Gly Cys Leu Val
                140                 145                 150

Lys Asp Tyr Phe Pro Glu Pro Val Thr Val Ser Trp Asn Ser Gly
                155                 160                 165

Ala Leu Thr Ser Gly Val His Thr Phe Pro Ala Val Leu Gln Ser
                170                 175                 180

Ser Gly Leu Tyr Ser Leu Ser Ser Val Val Thr Val Pro Ser Ser
                185                 190                 195

Ser Leu Gly Thr Gln Thr Tyr Ile Cys Asn Val Asn His Lys Pro
                200                 205                 210

Ser Asn Thr Lys Val Asp Lys Lys Val Glu Pro Lys Ser Cys Asp
                215                 220                 225

Lys Thr His Thr Cys Pro Pro Cys Pro Ala Pro Glu Leu Leu Gly
                230                 235                 240

Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr
                290                 295                 300

Asn Ser Thr Tyr Arg Val Val Ser Val Leu Thr Val Leu His Gln
                305                 310                 315

Asp Trp Leu Asn Gly Lys Glu Tyr Lys Cys Lys Val Ser Asn Lys
                320                 325                 330

Ala Leu Pro Ala Pro Ile Glu Lys Thr Ile Ser Lys Ala Lys Gly
                335                 340                 345

Gln Pro Arg Glu Pro Gln Val Tyr Thr Leu Pro Pro Ser Arg Glu
                350                 355                 360

Glu Met Thr Lys Asn Gln Val Ser Leu Thr Cys Leu Val Lys Gly
```

-continued

```
                365                 370                 375
Phe Tyr Pro Ser Asp Ile Ala Val Glu Trp Glu Ser Asn Gly Gln
                380                 385                 390
Pro Glu Asn Asn Tyr Lys Thr Thr Pro Pro Val Leu Asp Ser Asp
                395                 400                 405
Gly Ser Phe Phe Leu Tyr Ser Lys Leu Thr Val Asp Lys Ser Arg
                410                 415                 420
Trp Gln Gln Gly Asn Val Phe Ser Cys Ser Val Met His Glu Ala
                425                 430                 435
Leu His Asn His Tyr Thr Gln Lys Ser Leu Ser Leu Ser Pro Gly
                440                 445                 450
Lys
```

NUCLEIC ACID ENCODING ANTI-IGE ANTIBODIES

RELATION BACK AND PRIORITY INFORMATION

This is a continuation of U.S. Ser. No. 09/925,179, filed Aug. 8, 2001, now U.S. Pat. No. 6,914,129, which is a continuation of U.S. Ser. No. 08/466,163, filed Jun. 6, 1995, now U.S. Pat. No. 6,329,509 B1, which is a division of U.S. Ser. No. 08/405,617, filed Mar. 15, 1995, now abandoned, which is a continuation of U.S. Ser. No. 08/185,899, filed Jan. 26, 1994, now abandoned, which is a 35 U.S.C. § 371 of PCT/US92/06860, filed Aug. 14, 1992, which is a continuation-in-part of both U.S. Ser. No. 07/879,495, filed May 7, 1992, now abandoned and U.S. Ser. No. 07/744,768, filed Aug. 14, 1991, now abandoned; all of which are incorporated by reference and to which application priority is claimed under 35 U.S.C. § 120.

BACKGROUND OF THE INVENTION

This invention relates to amino acid sequence variant anti-IgE antibodies and to polypeptides containing IgE sequences, especially IgE antagonists and to polypeptides capable of differential binding to FcεRI and FcεRII.

IgE is a member of the immunoglobulin family that mediates allergic responses such as asthma, food allergies, type 1 hypersensitivity and the familiar sinus inflammation suffered on a widespread basis. IgE is secreted by, and expressed on the surface of, B-cells. IgE synthesized by B-cells is anchored in the B-cell membrane by a transmembrane domain linked to the mature IgE sequence by a short membrane binding region. IgE also is bound to B-cells (and monocytes, eosinophils and platelets) through its Fc region to a low affinity IgE receptor (FcεRII, hereafter "FCEL"). Upon exposure of a mammal to an allergen, B-cells are clonally amplified which synthesize IgE that binds the allergen. This IgE in turn is released into the circulation by the B-cells where it is bound by B-cells (through the FCEL) and by mast cells and basophils through the so-called high affinity receptor (FcεRI, hereinafter "FCEH") found on the surface of the mast cells and basophils. Such mast cells and basophils are thereby sensitized for allergen. The next exposure to the allergen cross-links the FcεRI on these cells and thus activates their release of histamine and other factors which are responsible for clinical hypersensitivity and anaphylaxis.

The art has reported antibodies capable of binding to FCEL-bound IgE but not IgE located on FCEH (see for example WO 89/00138 and U.S. Pat. No. 4,940,782). These antibodies are disclosed to be clinically advantageous because they bind to IgE found on B-cells or circulating free in the body, but do not bind to FCEH and thus will not activate mast cells or basophils. In addition, various amino acid sequence variants of immunoglobulins are known, e.g., "chimeric" and "humanized" antibodies (see, for example, U.S. Pat. No. 4,816,567; WO 91/09968; EP 452,508; and WO 91/16927). Humanized antibodies are immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues which are found neither in the recipient antibody nor in the imported CDR or framework sequences. These modifications are made to further refine and optimize antibody performance as will be more further described infra. Also known per se are monovalent and bispecific antibodies.

It is generally understood that FCEH, like FCEL, binds to recognition site(s) in the IgE constant (Fc) domain. The IgE recognition site(s) for the two receptors are poorly defined, despite considerable effort in the past directed to the problem.

Over the past decade several studies have been undertaken to determine which portion of the IgE molecule is involved in binding to FcεRI and FcεRII. Essentially three approaches have been tried. First, peptides corresponding to specific portions of IgE sequence have been used as either competitive inhibitors of IgE-receptor binding (Burt et al., *Eur. J. Immun,* 17:437-440 [1987]; Helm et al., *Nature,* 331:180-183 [1988]; Helm et al., *Proc. Natl. Acad. Sci.,* 86:9465-9469 [1989]; Vercelli et al., *Nature,* 338:649-651 [1989]; Nio et al., *Peptide Chemistry,* 203-208 [1990]) or to elicit anti-IgE antibodies which would block IgE-receptor interaction (Burt et al., *Molec. Immun.* 24:379-389 [1987]; Robertson et al., *Molec. Immun.,* 25:103-113 [1988]; Baniyash et al., *Molec. Immun.* 25:705-711 [1988]). The most effective competitive peptide was a sequence that was 1000-fold less active than IgE (Burt et al., *Eur. J. Immun.,* 17:437-440 [1987]).

Helm et al., *Proc. Natl. Acad. Sci.,* 86:9465-9469 (1989) found that a peptide corresponding to IgE residues 329-409 blocked in vivo sensitization of human basophil granulocytes with human IgE antibodies. Further studies indicated that residues 395-409 were not essential for binding of the 329-409 peptide to FcεRI (Helm et al., *Proc. Natl. Acad Sci.,* 86:9465-9469 [1989]). Note that the IgE sequence variants described below had the sequence of Padlan et al., *Mol. Immun.,* 23:1063 (1986), but that the immunoglobulin residue numbers used herein are those of Kabat et al., *Sequences of Proteins of Immunological Interest* (National Institutes of Health, Bethesda, Md. 1987).

Vercelli et al., *Nature,* 338:649-651 (1989) used recombinant IgE peptides as well as anti-Fcε monoclonal antibodies to investigate the B-cell (FcεRII) binding site of human IgE. They concluded that the FcεRII binding site is in Fcε3 near K399-V402.

Burt et al., *Eur. J. Immun.,* 17:437-440 (1987) investigated seven peptides for competition against rat IgE in binding to rat mast cells. Their most active peptide, p129, was 1000-fold less active than IgE. p129 corresponds to human sequence 439-453 which includes loop EF. Another of their peptides, p130, corresponding to residues 396-419 in the Fcε3 domain, had no activity.

Robertson et al., *Molec. Immun.,* 25:103-113 (1988) assessed IgE binding by sequence-directed antibodies induced by several synthetic peptides. They concluded that the sequence defined by their ε-peptide-4 (corresponding to residues 446-460), was not significantly involved in receptor binding while the sequence defined by their ε-peptide-3 (corresponding to residues 387-401), was likely to be proximal to the IgE-receptor recognition site.

Nio et al., *Peptide Chemistry,* 203-208 (1990) evaluated numerous peptides with respect to their ability to inhibit histamine release by human basophils in vitro. Only one peptide (peptide 2, Table 1), exhibited specific inhibition;

this peptide encompassed residues 376-388. However, a larger peptide which incorporated this sequence (peptide 3, Table 1), had no inhibitory activity.

Second, mutations in IgE have been partially explored. Schwarzbaum et al., *Eur. J. Immun.*, 19:1015-1023 [1989] (supra) found that a point mutant P404H (P442H by the numbering system used herein) had 2-fold reduced affinity for FcεRI on rat basophilic leukemia (RBL) cells, but the interpretation of this finding is controversial (Weetall et al., *J. Immunol.*, 145:3849-3854 [1990]).

Third, chimeric molecules have been constructed. Human IgE does not bind to the murine receptor (Kulczycki Jr., et al., *J. Exp. Med.*, 139:600-616 [1974]) while rodent IgE binds to the human receptor with a reduced affinity (Conrad, et al., *J. Immun.*, 130:327-333 [1983]); human IgG1 does not bind to IgE receptors (Weetall et al., *J. Immun.*, 145:3849-3854 [1990]). Based on these observations, several groups have constructed human-murine chimeras or human IgE-IgG chimeras. Weetall et al., *J. Immun.*, 145:3849-3854 (1990) made a series of human IgG1-murine IgE chimeras and concluded that the Fcε2 and Fcε3 domains are involved in binding murine FcεRI while the Fcε4 domain is unlikely to be involved in binding to murine FcεRI (but may possibly be involved in binding to FcεRII). However, these conclusions are uncertain since they rest primarily on lack of binding by chimeras and three of five chimeras lacked some interchain disulfide bonds.

Nissim et al., *EMBO J.*, 10:101-107 (1991) constructed a series of human-murine IgE chimeras and measured binding to RBL cells and concluded that the portion of IgE which binds with high affinity to the specialized Fcε receptor on RBL cells could be assigned to Fcε3.

The results reported by these authors (e.g., Helm et al. and Burt et al.) are inconsistent. Further, in the case of anti-IgE antibodies it is difficult to eliminate the possibility of non-specific blocking due to steric hindrance (Schwarzbaum et al., *Eur. J. Immun.*, 19:1015-1023 [1989]). It is apparent that considerable confusion exists in the art as to the domains of IgE Fc which are involved in the binding of IgE to FCEH or in the maintenance of IgE conformation responsible for IgE binding to FCEH.

It is an object of this invention to identify polypeptides capable of differential binding to FCEL and FCEH.

It is an object herein to determine an IgE domain which is implicated in FCEH receptor binding, but which is not involved in FCEL receptor binding, and vice-versa.

It is another object herein to identify antagonists which are capable of inhibiting allergic responses, including antagonists that neutralize the FCEH or FCEL receptor-binding domains of Fcε, immunoglobulin analogues that bind FCEL but do not bind FCEH, or that bind FCEH but not FCEL and humanized anti-huIgE antibodies that bind to FCEL-bound IgE but not to FCEH-bound IgE or which bind to IgE but do not induce histamine release or degranulation of mast cells.

It is another object to provide novel polypeptides for use in the assay of Fcε receptors and for use as immunogens or for selecting anti-IgE antibodies.

SUMMARY OF THE INVENTION

We have identified domains and specific residues of IgE which play an important role in binding IgE to its FCEL and FCEH receptors, and based on this information we have designed polypeptides which remain capable of substantially binding to only one of these two receptors while being substantially incapable of binding to the other of the receptors. These polypeptides are referred to as differential binding polypeptides. In particular, differential binding polypeptides that bind FCEL comprise IgE sequences in which one or more residues in loop EF or the β-strand D domain are varied, while FCEH-binding polypeptides comprise IgE sequences in which loop AB and/or β-strand B sequences are varied. Conversely, included herein are certain polypeptides comprising functional IgE loop EF and β-strand D domains but loop AB and/or β strand B domains having reduced functionality compared to wild-type, which bind differentially to FCEH, and polypeptides comprising functional loop AB and β-strand B domains but β-strand D and/or loop EF domains having reduced functionality compared to wild-type, which bind differentially to FCEL.

The differential binding polypeptides of this invention are sufficiently homologous with the amino acid sequence of an IgE heavy chain that they retain the capability to bind FCEL or FCEH, but are varied such that they exhibit reduced ability to bind to one of the two receptors as compared to native IgE. In various embodiments, the polypeptides of this invention additionally comprise cytotoxic polypeptides, detectable labels, conformation-restraining groups and/or amino acid sequences which are heterologous to IgE, e.g., sequences from receptors or immunoglobulins as further described below. In other embodiments, the differential binding polypeptides comprise IgE sequences in addition to the above-mentioned receptor binding domains, e.g., at least one variable domain capable of binding a predetermined antigen. In another embodiment, the differential binding polypeptide is an IgE variant which is monovalent for a predetermined antigen. In a still further embodiment, the differential binding polypeptide comprises an inactive IgE variable domain, i.e., one which is incapable of binding to any antigen, or which is devoid of a variable domain or functional CDR.

The differential binding polypeptides of this invention are useful in diagnostic procedures for IgE receptors or in the therapy of IgE-mediated disorders such as allergies. They also are useful in preparing antibodies capable of binding regions of IgE that participate in receptor binding.

In an embodiment of this invention, variant anti-IgE antibodies are provided for use in diagnosis or for the therapy or prophylaxis of allergic and other IgE-mediated disorders. In particular embodiments of this invention anti-IgE variant antibodies are provided in which one or more human (recipient) light chain residues 4, 13, 19, 24, 29, 30, 33, 55, 57, 58, 78, 93, 94, or 104, or heavy chain residues 24, 37, 48, 49, 54, 57, 60, 61, 63, 65, 67, 69, 78, 82, 97 or 100 have been modified, preferably by substitution with the residue found in the corresponding position in the donor (generally murine) antibody. In preferred embodiments, the selected residues are light chain 13, 19, 58, 78, or 104, or heavy chain residues 48, 49, 60, 61, 63, 67, 69, 82 or 82c, and most preferably are heavy chain residues 60, 61 or light chain residue 78.

In other embodiments we provide antibodies which are capable of binding FCEL-bound IgE but which are substantially incapable of binding FCEH-bound IgE or inducing histamine release from mast cells or basophils, comprising a human Kabat CDR domain into which has been substituted a positionally analogous residue from a Kabat CDR domain of the murine anti-huIgE antibodies MAE11, MAE13, MAE15 or MAE17. Also provided herein are bispecific antibodies and IgE-monovalent antibodies; and humanized antibodies exhibiting an affinity for IgE which ranges from about 0.1 to 100 times that of MAE11.

BRIEF DESCRIPTION OF THE FIGURE

FIG. 1 depicts the sequence of human IgE Fcε2 and Fcε3 (SEQ ID NO: 1). This particular sequence is from Padlan et al., *Molec. Immun.*, 23:1063-1075 (1986). Residues are numbered according to Kabat (supra). "X" residues are included to align the Padlan IgE sequence with the Kabat numbering scheme. Sequences which were altered in preparing various IgE mutants are underlined; bold numbers below the lines denote the mutant number. β-strand residues are overlined; loop residues are defined by all residues intervening between two β-strands.

FIG. 2 depicts light and heavy chain sequences for MAE11 (SEQ ID NOS: 2 and 3), MAE13 (SEQ ID NOS: 4 and 5) and MAE15 (SEQ ID NOS: 6 and 7).

FIG. 3 depicts heavy and light chain sequences for HuMae11V1 (SEQ ID NOS: 8 and 9).

FIGS. 5a-5c compare the binding of the MAE11, MAE15 and MAE17 antibodies to various huIgE variants. MAE1 is provided as a control which binds to both B cells and mast cell-bound IgE. The mutants scheduled in the boxes in each figure are identified in Table 11.

DETAILED DESCRIPTION OF THE INVENTION

Figure 4A:
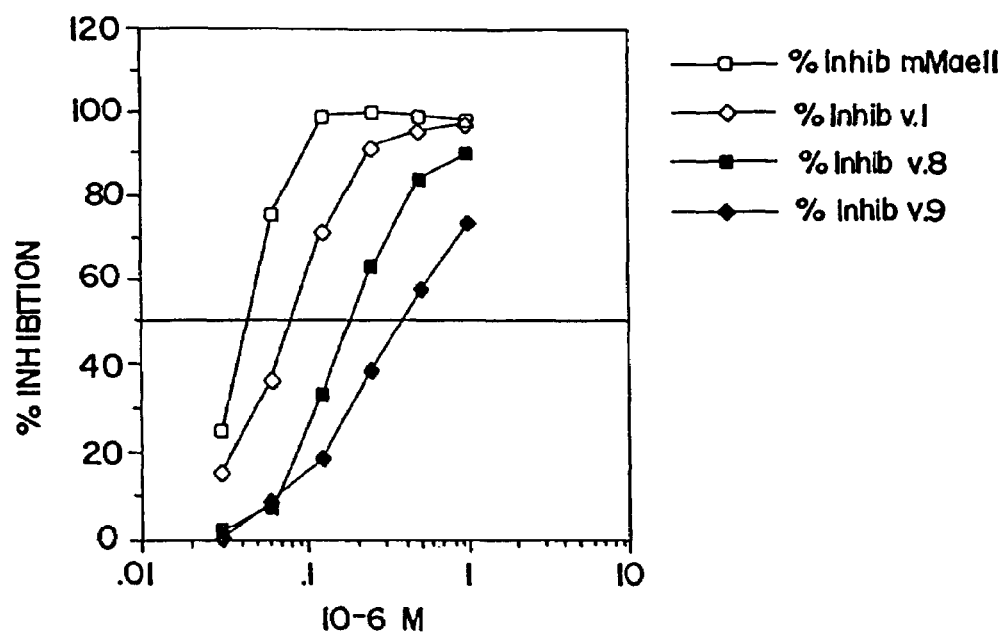
FIGS. 4a and 4b depicts the percent inhibition of IgE binding to FCEL and FCEH receptors, respectively, by murine monoclonal antibody Mae11 as well as 3 humanized variants (v1, v8 and v9).

The IgE analogue polypeptides of this invention contain an amino acid sequence which is homologous to that of a naturally occurring IgE and have the ability to bind specifically or differentially to FCEL or FCEH but, in varying degree, not to both. The degree of homology of such polypeptides to wild-type IgE is not critical since only enough IgE sequence needs to be retained to enable the IgE to bind differentially or specifically to one of the two receptors. In general, the polypeptides of this invention will be IgE Fc analogues and will be about from 80% to 99% homologous with a polypeptide sequence of a naturally occurring IgE heavy chain Fc region. Homology is determined by conventional methods in which all substitutions are considered to be nonhomologous (whether conservative or nonconservative) and in which the sequences are aligned to achieve maximal homology.

It will be understood that the IgE Fc residue numbers referred to herein are those of Kabat. In applying the residue teachings of this invention to other IgE Fc domains it will be necessary to compare the entire candidate sequence with the FIG. 1 sequence in order to align the residues and correlate the residue numbers. In addition, the identity of certain individual residues at any given Kabat site number may vary from IgE to IgE due to interspecies or allelic divergence. When for example it is stated that substitutions are introduced at residue R383 (human IgE) it will be understood that this means introducing a substitution at the same site in IgE even though this same site (in loop AB) may be located at a different residue number or may be represented in the parental or starting IgE by a residue which is different than that described by Kabat. However, for the sake of clarity and simplicity the residue numbers and identities of the Kabat human IgE heavy chain sequences will be used herein. Note that some Kabat residues were deleted in the Padlan sequence, in which case the Kabat numbering system is preserved by insertion of a spacer residue designated "X" (See FIG. 1).

Similarly, the Kabat system is used to designate immunoglobulin residues used in the preparation of variant, e.g. humanized, anti-IgE immunoglobulins such as IgG, IgE, IgA or IgD. In preferred embodiments the recipient human immunoglobulin site is numbered in accord with Kabat subgroups III ($V_H$) consensus and K subgroup I ($V_L$) consensus sequences. In order to determine which donor residues correspond to these Kabat consensus residues the sequences are maximally aligned, introducing gaps as necessary, using the variable domain cysteine residues as principal guideposts. Note that CDRs vary considerably from antibody to antibody (and by definition will not exhibit homology with the Kabat consensus sequences). Maximal alignment of framework residues (particularly the cysteines) frequently will require the insertion of "spacer" residues in the numbering system, to be used for the $F_v$ region of the donor antibody. For example, the residue "29a" referred to infra. This represents an extra residue found in the murine donor antibody $V_{H1}$ CDR for which a counterpart does not exist in the consensus sequence but whose insertion is needed to obtain maximal alignment of consensus and donor sequences. In practice, then, when a humanized antibody (ver. 1) is prepared from this donor it will contain $V_{H1}$ with residue 29a. The differential binding polypeptides of this invention typically contain about from 5 to 250 residues which are homologous to an IgE heavy chain Fc region, but ordinarily will contain about from 10 to 100 such residues. Usually, the IgE Fc3 and Fc4 regions will be present, with the Fc3 domain providing residues directly involved in receptor binding with Fc4 being present to ensure conformational integrity.

Generally, the IgE is human IgE, although animal IgE such as rat, murine, equine, bovine, feline or porcine IgE is included. As noted above, there will be variation in the residue identities and numbers for these IgEs compared to the FIG. 1 sequence.

FCEH and FCEL are respectively defined to be the high affinity IgE receptor (FCεRI, Ishizaka et al., *Immunochemistry*, 7:687-702 [1973]) found on mast cells or basophils, and the low affinity receptor (FCεRII, or CD23) found on cells involved in inflammation such as monocytes, eosinophils and platelets, as well as B-cells (Capron et al., *Immun. Today*, 7:15-18 [1986]). FCEH and FCEL include alleles and predetermined amino acid sequence variants thereof which bind IgE. While FCEH contains several polypeptide chains, the binding of candidate polypeptides to its alpha chain is all that needs to be assayed since the alpha chain is the portion of FCEH which binds IgE.

Differential binding means that the polypeptide will bind to one of FCEL or FCEH to the extent of at least about 75% of the degree with which the homologous native IgE binds to that receptor, but will not bind to the other receptor at more than about 20% of the degree that the homologous IgE binds to the other receptor. Binding is determined by the assays of Example 3. Included within this invention are polypeptides that are capable of binding to one of the two receptors to a greater degree than native IgE.

FCEL-Specific Polypeptides

These polypeptides preferentially bind to the low affinity receptor. They typically contain Fcε3 sequences in which residues within the β-strand D domain or loop EF have been substituted or deleted, and/or an additional residue inserted adjacent to one of such residues. For the purposes herein, the beta strand D domain extends from N418-X431 (FIG. 1, wherein X indicates a residue omitted from U266 IgE but found in the Kabat sequence) and loop EF extends from G444 to T453. A preferred FCEL-specific embodiment is mutant 6 (Table 6), in which the substitution of 4 residues within the human IgE heavy chain sequence K423-R428 substantially abolished FCEH binding. Other FCEL-specific embodiments comprising EF loop variants are mutants 85, 89 and the combination of 49, 51, 52, 83, 86 and 87. These sites (the D and EF domains) are believed to be the principal sites involved in binding IgE to FCEL. However, those skilled in the art will be able to routinely screen for optimal FCEL-specific polypeptides using the methods shown in the examples once it is understood that the beta-strand D and loop EF domains are the prinicipal mutagenesis targets.

The preferred FCEL-specific polypeptide is one in which a residue has been substituted or deleted from within the β-strand D domain or loop EF, or both. For example, four residues were substituted in generating mutation 6, and any one or more of these substitutions may be responsible for the loss in FCEH binding while retaining FCEL binding. As for loop EF, which is involved in both FCEL and FCEH binding, it is desirable to screen both activities in order to select the FCEL-specific IgE variants. For example, mutant 85 (in which 9 IgE residues are substituted by analogously positioned IgG residues) is not detectably capable of binding to FCEH, but does bind to FCEL (see Table 11). On the other hand, conversion of site 444 from Gly to Leu abolishes binding to either receptor, while sites 447 and 452 are involved in binding to both receptors since changes at these locations prevent binding to FCEL but do not abolish FCEH binding.

Beta-Strand D Variants for FCEL Specificity

In general, D domain substitutions will be nonconservative, i.e., substituted residues generally will differ substantially from those found within the homologous native IgE in terms of charge, hydrophobicity or bulk. Typically, a maximum of 4 of 14 β-strand D domain residues are varied (and are usually residues 423, 424, 426 and/or 428), although typically any 1 to 5 of these residues are suitable for variation. In general, no more than 4 residues need to be varied and optimally only one will be varied.

K423 and/or K426 are substituted with any of a residue selected from the group of Arg, His, Cys, Met, Phe, Tyr, Trp, Pro, Gly, Ala, Val, Ile, Leu, Ser, Thr, Asp, Glu, Gln and Asn, preferably Gly, Pro, Glu, Gln and Asp and most preferably Pro or Gln.

E424 and/or E425 are substituted with any of a residue selected from Asp, Asn, Gln, His, Lys, Arg, Cys, Met, Phe, Tyr, Trp, Pro, Gly, Ala, Val, Leu, Ile, Ser and Thr, preferably Arg, Lys, Pro, Gly and His and most preferably Arg.

R428 and/or R422 are substituted with Cys, Met, Phe, Tyr, Trp, Pro, Gly, Ala, Val, Leu, Ile, Ser, Thr, Asp, Glu, Asn, Gln, His, and Lys, preferably Cys, Met, Phe, Tyr, Trp, Pro, Gly, Ala, Val, Leu, Ile, Ser, Thr, Asp, Glu, Asn and Gln, and most preferably Tyr.

T421 is substituted with Cys, Met, Phe, Tyr, Trp, Pro, Gly, Ala, Val, Len, Ile, Ser, Asp, Glu, Asn, Gln, His and Lys, preferably Met, Phe, Tyr, Trp, Pro, Gly, Ala, Val, Leu, Ile, Asp, Glu, Asn, Gln, His and Lys, and most preferably Phe, Trp, Pro, Gly, Ala, Val, Len and Ile.

S420 is substituted with Met, Phe, Tyr, Trp, Pry, Gly, Ala, Val, Leu and Ile, and preferably Pro or Gly.

X429 is substituted with any other naturally occurring amino acid residue.

It is likely that optimal differential and FCEL binding activity will be achieved by a combination of mutations. Preferably, FCEH or FCEL binding, as the case may be, will be less than 10% of native homologous IgE, and optionally will range from undetectable to 3% of native homologous IgE, while binding to the other receptor ranges from at least about 75% of native homologous IgE to 90%, and preferably 95% to greater than 100%, e.g. 125%. The mutations should be as conservative as possible, i.e., involve as modest changes in hydrophobicity, charge or bulk as possible, yet still result in a polypeptide exhibiting these differential binding characteristics.

Any one or more of the β-strand D domain residues also may be deleted. Deletion of residues may possess the advantage of not introducing potentially immunogenic sites into the IgE analogue.

Examples of candidate β-strand D domain substitutional or deletional variants are set forth in the following Table 1. To determine the sequence of each variant, identify the residue for each variant number under each site. For example, the sequence of compound 19 comprises C388 E389 E390, etc.

TABLE 1

| | HuIgE Site | | | | | |
|---|---|---|---|---|---|---|
| AA[1] | 423 K | 424 E | 425 E | 426 K | 427 Q | 428 R |
| C | 19 | 20 | | 37 | | 55 |
| M | 18 | 21 | | 38 | | 56 |
| F | 8, 80 | 22 | | 39 | | 57, 88 |
| Y | 7 | 23 | | 40 | | 4, 75, 83-84, 89, 97 |
| W | 6 | 24 | | 41 | | 58, 85 |
| P | 1, 74, 78-79, 89, 103 | 25, 97 | | 42 | | 59 |
| G | 5, 76-77 | 26 | | 43 | | 60 |
| A | 12, 98-99 | 27, 98, 100 | | 44, 98, 101 | | 61, 98, 102 |
| V | 13, 97 | 28 | | 45 | | 62 |
| L | 14, 81 | 29 | | 46 | | 63 |
| I | 15, 82 | 30 | | 47 | | 64 |
| S | 16 | 31 | | 48 | | 65, 103 |
| T | 17 | 32 | | 49 | | 66, 104, 105 |
| D | 9 | | 79 | 50 | | 67, 86 |

TABLE 1-continued

| | HuIgE Site | | | | | |
|---|---|---|---|---|---|---|
| AA[1] | 423 K | 424 E | 425 E | 426 K | 427 Q | 428 R |
| E | 9, 94 | 1, 3-19, 37-54, 55-72, 75, 88, 89, 90-93, 99, 101, 102, 105 | 1-72, 74, 76-78, 80-88, 93-94, 99, 100-105 | 51 | | 68, 87 |
| N | 10 | 33 | | 52, 79, 84 | 79 | 69 |
| Q | 11 | 34 | | 3, 54, 75, 80, 82-83, 85-89, 103-104 | 1-72, 75, 77, 78, 80-95, 97-103, 105 | 70 |
| H | 83, 104 | 35, 78, 84 | | 53 | | 71 |
| K | 2-4, 20-72, 75, 85-88, 91-93, 100-102, 105 | 36, 77, 79, 94 | | 1-2, 5-36, 55-72, 74, 76, 77-90, 91, 93-95, 97, 99, 100, 102, 105 | 104 | 72, 79 |
| R | 84 | 2, 74, 76, 80, 81 83, 85-87, 103-104 | 89 | | | 1-3, 5-54, 74, 76-78, 80-82, 90-92, 94, 99, 100-101 |
| Δ[2] | 90, 95, 96 | 91, 95, 96 | 91, 96 | 92, 96 | 96 | 93, 95, 96 |

[1]amino acid residues substituted into the variant
[2]signifies a deletion

Insertion of one or more extraneous residues adjacent to a residue within the β-strand D domain also falls within the scope of this invention. Typically, only one residue will be inserted, although from 2 to 4 or more residues can be inserted adjacent to any one site within the domain. Smaller numbers of inserted residues will be preferred in order to avoid the introduction of immunogenic sites. This, however, is merely a matter of choice. In general, insertions will be made at a single site, although insertions can be made adjacent to any two or more β-strand D domain residues.

Insertions typically are made between the following residues: 422 and 423, 423 and 424, 424 and 425, 425 and 426, 426 and 427, 427 and 428 and/or 428 and 429. The inserted residue or residues generally will exhibit charge, bulk or hydrophobicity character which is distinct from that of the flanking residues. For example, candidate insertions can be selected from the following Table 2.

TABLE 2

| Insertion | β-strand D domain site[1] |
|---|---|
| Q | 1, 2, 3, 4, 5, 7 or 8 |
| D | 1, 2, 3, 4, 5, 6 or 7 |
| E | 1, 2, 3, 4, 5, 6 or 7 |
| F | 1, 2, 3, 4, 5, 6 or 7 |
| W | 1, 2, 3, 4, 5, 6 or 7 |
| P | 1 or 2 |
| K | 2 or 3 |
| R | 2 or 3 |
| EK | 2 or 7 |
| ER | 2 or 7 |
| DK | 2 or 7 |
| DR | 2 or 7 |
| G | 1 or 2 |
| A | 8 |
| Y | 6 or 7 |
| N | 1, 2, 3, 4, 5, 7 or 8 |
| H | 1, 2, 3, 4, 5, 7 or 8 |
| I | 1, 2, 3, 4, 5, 7 or 8 |

[1]422R - site 1 - 423K - site 2 - 424E - site 3 - 3425E - site 4 - 426K - site 5 - 427Q - site 6 - 428R - site 7 - 429X y - site 8. Absence of a site indicates no insertion at that site.

The FCEL-specific polypeptides need only contain so much of the IgE Fcε AB-B and loop EF domain sequences as are required to substantially achieve FCEL binding. This is readily determinable by preparing polypeptides comprising the AB-B and loop EF domains and incrementally increasing numbers of flanking or normally interposed residues, e.g., β-strand A (N-terminal) or loop BC, β-strand C, loop CD, β-strand D, loop DE, β-strand E, β-strand F, loop EF, loop FG, β-strand G, and Fcε4 (C-terminal). In general, the entire IgE sequence from Fcε3-Fcε4 is used, although fragments of FcE3 containing the AB-B domain may be satisfactory, particularly if they contain the AB-B domain, loop EF and intervening sequence, otherwise than as varied according to the teachings herein to achieve specificity for FCEL.

The FCEL-specific polypeptides are provided as linear or conformationally restrained polypeptides. Conformational restraint is accomplished by cross-linking the polypeptide, preferably at the N- and C-termini so as to produce a cyclic structure. In preferred embodiments the cyclic forms have the following structure:

Formula I $$\text{O} \quad (a_3-a_{11})(a_{12})(a_{13})(a_{14})(a_{15})\text{Pro}(a_{17})(a_{18})(a_{19}) - \overset{H}{N} \diagdown \text{COR}_1$$

$$R_3 \diagdown \underset{R_2}{\overset{}{N}} \diagdown \underset{R_4}{\overset{O}{C}} \diagdown \underset{R_6 \, R_5}{X} \diagdown R_8 \diagdown R_7$$

wherein (a3-a11) is a bond or the sequence -R373-F381; a12 and a18 are hydrophobic amino acid residues; a13 and a14 are basic amino acid residues; and a15, a17 and a19 are hydrophilic amino acid residues;

$R_1$ is selected from
  (a) hydroxy,
  (b) $C_1$-$C_8$ alkoxy,
  (c) $C_3$-$C_{12}$ alkenoxy,
  (d) $C_6$-$C_{12}$ arlyoxy, (e) acylamino-$C_1$-$C_8$-alkoxy
(f) pivaloyloxyethoxy,
(g) $C_6$-$Cl_{12}$ aryl-$C_1$-$C_8$-alkoxy where the aryl group is unsubstituted or substituted with one or more of the groups nitro, halo, $C_1$-$C_4$-alkoxy, and amino;
(h) hydroxy substituted $C_2$-$C_8$ substituted alkoxy; and
(i) dihydroxy substituted $C_3$-$C_8$ alkoxy;
$R_2$, $R_3$, $R_5$, $R_7$, $R_8$ are the same or different and are selected from
(a) hydrogen,
(b) $C_6$-$C_{12}$ aryl where the aryl group is unsubstituted or substituted by one or more of the groups nitro, hydroxy, halo, $C_1$-$C_8$ alkyl, halo-$C_1$-$C_8$ alkyl, $C_1$-$C_8$ alkoxy, amino, phenyl, acetamido, benzamido, di-$C_1$-$C_8$ alkylamino, $C_6$-$C_{12}$ aroyl, $C_1$-$C_8$ alkanoyl, and hydroxy substituted $C_1$-$C_8$ alkyl,
(c) $C_1$-$C_{12}$ alkyl or alkenyl; $C_3$-$C_{10}$ cycloalkyl or $C_3$-$C_{12}$ substituted with any of halo, $C_1$-$C_8$ alkoxy, $C_6$-$C_{12}$ aryloxy, hydroxy, amino, acetamido, $C_1$-$C_8$ alkylamino, carboxy or carboxamide;
$R_2$ and $R_3$, $R_5$ and $R_6$, or $R_7$ and $R_8$ may optionally and independently be joined together to form a carbocyclic or heterocyclic ring of from four to seven atoms where the heteroatoms are selected from O, S, or $NR_{10}$ where $R_{10}$ is selected from:
hydrogen, $C_1$-$C_8$-alkyl, $C_2$-$C_8$-alkenyl, $C_6$-$C_{12}$-aryl, $C_3$-$C^{10}$ cycloalkyl, $C_6$-$C_{12}$-aryl-$C_1$-$C_8$-alkyl, $C_1$-$C_8$-alkanoyl, and $C_6$-$C_{12}$ aroyl,
$R_4$ is selected from:
hydrogen, $C_1$-$C_8$-alkyl, $C_2$-$C_8$-alkenyl, $C_6$-$C_{12}$-aryl, $C_3$-$C_{10}$ cycloalkyl, $C_6$-$C_{12}$-aryl-$C_1$-$C_8$-alkyl, $C_1$-$C_8$-alkanoyl, and $C_6$-$C_{12}$ aroyl;
$R_2$ or $R_3$ may be optionally joined with $R_4$ to form a piperidine, pyrrolidine or thiazolidine ring;
X is selected from:
an O or S atom,
$NR_9$ wherein $R_9$ is hydrogen, $C_1$-$C_8$-alkyl, $C_3$-$C_8$-alkenyl, $C_3$-$C_{10}$ cycloalkyl, $C_6$-$C_{12}$-aryl, $C_6$-$C_{12}$-aryl-$C_1$-$C_8$-alkyl, $C_1$-$C_8$-alkanoyl, or $C_6$-$C_{12}$ aroyl; $C_6$-$C_{12}$ aryl, $C_1$-$C_8$ alkanoyl, and $(CH_2)k$ where k is an integer from 0 to 5; and pharmaceutically acceptable salts thereof.

As used herein and unless specified otherwise: alkyl and alkenyl denote straight or branched, saturated or unsaturated hydrocarbon chains, respectively; $C_6$-$C_{12}$ aryl groups denote unsubstituted aromatic rings or fused aromatic rings such as, for example, phenyl or naphthyl; halo denotes F, Cl, Br, or I atoms; alkoxy denotes an alkyl group bonded through O to the indicated site. Examples of $C_1$-$C_8$ alkyl or $C_2$-$C_8$ alkenyl groups include methyl, ethyl, propyl, isopropyl, butyl, t-butyl, pentyl, isopentyl, hexyl, vinyl, allyl, butenyl and the like; examples of $C_3$-$C_{10}$-cycloalkyl groups include cyclopropyl, cyclopentyl, cyclohexyl, and the like; heterocyclic rings include but are not limited to pyridyl, thienyl, furyl, indolyl, benzthienyl, imidazolyl, thiazolyl, quinolinyl and isoquinolinyl. Hydrophobic amino acid residues include naturally occurring or synthetic residues having hydrophobic side chains, e.g. Phe, Leu, Ile, Val, Norleu, and the like. Hydrophilic amino acid residues include naturally occurring or synthetic residues having charged or uncharged hydrophilic side chains, e.g. ornithine, Ser, Thr, Tyr, His, Asp, Glu, Lys and Arg. Preferably a15, a17 and a19 are unchanged and bear normal, secondary or tertiary mono or di-hydroxy substituted alkyl side chains. Basic residues have guanidino or amino-substituted side chains for the most part.

The AB-B domain and/or loop EF-containing, FCEL-specific polypeptides of this invention optionally are associated with other substances or are fused to additional polypeptide sequences. The polypeptides generally contain only IgE-homologous sequences, although they also or alternatively are labelled for diagnostic use (employing enzymes, radioisotopes, biotin or avidin, stable free radicals, and chemiluminescent or fluorescent moeities in conventional fashion). Also the polypeptides are fused to non-IgE polypeptides such as cytotoxic or immunosuppressive polypeptides, to other IgE polypeptides (e.g. Fv regions), or to polypeptides capable of binding to a predetermined ligand or antigen.

Cytotoxic polypeptides include IgG Fc effector sequences and polypeptide toxins such as diphtheria toxin or ricin A chain (U.S. Pat. Nos. 4,714,749 and 4,861,579). A preferred fusion is one in which the FCEL-specific sequence (such as that of the Fcε3-Fcε4 sequence of mutant 6) is fused at its N-terminus (i.e., at approximately D360) to the C-terminus of an immunoglobulin, or an immunoglobulin fragment terminating at the C-terminus of IgG Fcγ2 or IgG Fcγ3. Alternatively the FCEL specific polypeptide is fused to an effector IgG sequence in place of one or both of the IgG Fv domains in analogous fashion to known immunoadhesins.

The polypeptides herein optionally are fused to polypeptides which are capable of binding a predetermined antigen or ligand. Generally, these additional polypeptides will be IgE or other immunoglobulin Fv domains, although they optionally are heterologous polypeptides such as receptor extracellular domains (produced in the known fashion of immunoadhesions, e.g. as has been accomplished with CD4). Immunoglobulin sequences fused to the FCEL-specific polypeptides herein include Fc or variable sequences of the heavy chains of IgG1, IgG2, IgG3, IgG4, IgE, IgM, IgD or IgA. Any FCEL-specific heavy chain fusion optionally is disulfide bonded in the ordinary fashion to heavy chains having the same specificity (thereby forming homopolymers) or to different heavy chains (thereby forming heteropolymers), including different heavy chains having specificity for a different antigen. Such heteropolymeric heavy chains include heavy chains which are not FCEL-specific, e.g., these comprise native IgE sequences which bind to FCEL and FCEH in the ordinary fashion, or the heavy chains optionally include at least one heavy chain that is FCEL specific and at least one that is FCEH specific. Heteropolymeric heavy chains also may include the heavy chains of non-IgE immunoglobulins, e.g., IgG, IgD, IgM and the like. In addition, the heavy chain hetero- or homopolymers optionally are disulfide bonded to light chains in the fashion of native immunoglobulins so as to cooperatively bind to predetermined antigen in the usual way. Unless the heteropolymeric heavy chains comprise IgM heavy chains they generally will be heterodimeric.

In some embodiments, immunoglobulins comprising an FCEL-specific polypeptide will also comprise an immunoglobulin variable region, preferably (if at all) an IgE Fv domain. The antigenic specificity of the variable region may vary widely, including those which bind haptens, or which bind polypeptides or proteins from human, animal, plant, fungal, bacterial or insect sources. The specificity may be unknown or the variable region may have the ability to bind to a predetermined antigen. If the immunoglobulin is to have a functional variable domain (as opposed to a deleted Fv in the case of Fcε3 or Fcε4 fragments) it is preferred that it have a known antigenic specificity. Antigenic specificity may include the ability to bind antigens associated with a cytotoxic or immune response particularly lymphoid cell antigens such as CD3 or CD8, integrins, B-cell surface antigens, helper or suppressor cell surface antigens, or epitopes located in the variable region of effector subtypes of IgG. FCEL-specific Fc domains also are usefully employed in combination with $F_v$ domains capable of binding a particular allergen to which a patient is allergic. These generally are human IgEs directed against allergens and which contain an FCEL-specific Fc domain. Alternatively, the immunoglobulin specificity is directed against the Fc region of effector subtypes of IgG, in this case however it being preferable that the FCEL-specific polypeptide not suppress complement binding or ADCC functions of the IgG.

The polypeptides of this invention that contain antigen or ligand binding capability contain one or more sites capable of binding to the antigen or ligand. For example, the polypeptides herein comprise one or more IgE or other immunoglobulin Fv domain to produce monovalent or polyvalent immunoglobulins. For the most part such polypeptides will be monovalent for antigen or ligand, as in the case when the immunoglobulin comprises a heavy-light chain pair that has a deleted or inactivated Fv or CDR so as to not be able to bind to antigen. Alternatively, they will be bivalent in the predominant instance, and will be monospecific or bispecific.

In another embodiment, FCEL-specific polypeptides are covalently bound to a cytotoxic agent. For example, the polypeptide ricin D toxin isolated from the *Ricinus communis* plant is bound to the carboxy terminus of the Fc domain, either by chemical means or, most preferably, by production of a fusion protein using standard recombinant DNA methods. This provides a means to selectively deliver the toxin only to cells expressing FCEL on their surfaces.

The FCEL-specific polypeptides need only contain so much of the IgE Fcϵ sequence as is required to substantially maintain FCEL binding. This is readily determinable by synthesizing or expressing the product and determining its activity. In general, the entire IgE sequence extending from Fcϵ2-Fcϵ4 can be used, although fragments containing only FcE3 and FcE4 are generally satisfactory.

In general the immunoglobulin sequences and the FCEL-specific sequence will be derived from the same species which is to be treated with the IgE analogue. Preferably, the immunoglobulin sequences are human.

The FCEL-specific polypeptides of this invention (when employed as such without fusion to non-IgE sequences) exclude the linear polypeptide sequences disclosed by Nio et al. (supra), as well as other prior art polypeptides which include the native IgE AB-B domain or loop EF (Burt et al., supra).

FCEH-Specific Polypeptides

These polypeptides are amino acid sequence variants of IgE or its fragments in which a residue within the AB-B or loop EF domains have been deleted, substituted or another residue inserted so that the AB-B or loop EF domains are no longer capable of binding to FCEL, and which contain sufficient beta strand D sequence and (optionally) loop EF sequence to bind to the high affinity receptor. As disclosed above, the AB-B and loop EF domains have been implicated in binding to FCEL since mutations in these domains have a serious impact on the binding of the IgE variants to the low affinity receptor. In particular, mutations in loop EF or the C-terminal half of the AB loop and in the N-terminal half of beta strand B produce a divergence in IgE FCEL/FCEH specificity wherein the variant continues to bind to the high affinity receptor but largely fails to bind to the low affinity receptor. In addition, we have found that the IgE loop EF and the heavy chain beta strand D domains participate in binding to the high affinity receptor. Therefore, FCEH-specific differential binding polypeptides will comprise at least the FCEH-binding sequence of beta strand D and preferably also will contain a variant AB-B or loop EF domain sequence that binds substantially only to FCEH.

In preferred embodiments amino acid sequence variation is introduced into the low affinity receptor binding functionality of the AB-B or loop EF domains. Preferably, one or more of residues I382, R383, K384, S385, T387, I388, T389, C390, R446, D447, W448, I449, E150, G151, E152 or T153 are varied, although modifications optionally are introduced into loop AB N-terminal to the designated loop AB residues. Only one of R383, K384, S385, T387, T-389, or R446-T453 need be mutated, although it is preferable to vary 1, 2 or 3 residues from each domain.

When substituted at all, I382 and/or I388 generally are independently substituted with Asn, Gln, Leu, Val, His, Lys, Arg, Met, Phe, Tyr, Trp, Pro, Gly, Ala, Ser, Thr, Asp or Glu, preferably Trp, Pro, Gly, Ser, Thr, Asp or Glu. Ordinarily these two residues are not modified.

R383 typically is substituted with Cys, Met, Phe, Tyr, Trp, Pro, Gly, Ala, Val, Leu, Ile, Ser, Thr, Asp, Glu, Asn, Gln, His, or Lys, preferably Met, Phe, Tyr, Trp, Pro, Gly, Ala, Val, Leu, Ile, Ser, Thr, Asp, Glu, Asn or Gln and most preferably Ala, Glu, Asp or Ser.

K384 typically is substituted with Arg, His, Cys, Met, Phe, Tyr, Trp, Pro, Gly, Ala, Val, Ile, Leu, Ser, Thr, Asp, Glu, Gln and Asn, preferably Ala, Gly, Pro, Glu, Gln or Asp and most preferably Ala, Glu or Asp.

S385 is substituted with Asp, Asn, Gln, His, Lys, Arg, Cys, Met, Phe, Tyr, Trp, Pro, Gly, Ala, Val, Leu, Ile, Glu and Thr, preferably Ala, Tyr, Val, Ile, Leu, Phe, Arg, Lys and His and most preferably Ala, Val, Ile, Leu, Phe and Tyr. When substituted, P386 usually is substituted by Gly, Ala, Cys, Val, Leu, Ile, Ser, Thr, Asp, Glu, Asn, Gln, His, Lys, Arg, Phe, Tyr, or Trp, and preferably Gly, Ala, Ser, Thr, Asp, Glu, Asn, Gln, His, Lys, Arg or Trp. Ordinarily, P386 is not modified.

T387 and/or T389 generally are independently substituted by Gly, Ala, Val, Leu, Ile, Ser, Asp, Pro, Glu, Asn, Gln, His, Lys, Arg, Cys, Phe, Tyr and Trp, preferably Gly, Ala, Val, Leu, Ile, Asp, Glu, Asn, Gln, His, Lys, Arg, Phe, Tyr and Trp, and most preferably Ala.

C390 ordinarily is not substituted except when employed as a component of a cyclizing group as shown in Formula I.

The differential FCEH-binding polypeptides of this invention will comprise the sequence of functional FCEH-binding beta strand D and loop EF domains, as defined above. In general, it is expected that the functional domains need not contain all of the beta strand D or loop EF domain residues. However, any modifications of the beta strand D domain residues will need to be conservative, if made at all, in order to preserve FCEH binding. Since loop EF is involved in both FCEL and FCEH binding, it likely will be necessary to screen these variants in order to determine their activity as shown in Example 5. However, a number of loop EF mutants already have been identified that substantially abolish FCEL binding without apparently interfering with FCEH binding, e.g. mutants 50 and 52. Thus, loop EF variants may belong in either the FCEL or FCEH specific category, or may equally affect binding to each receptor.

A particularly preferred embodiment of a FCEH-specific polypeptide is one which contains a beta strand D domain together with additional C-terminal sequence. The sequence of this embodiment extends from about T421 to about T440. Generally, the N-terminus of this embodiment is S420 or T421, while the C-terminus is T440, L441 or P442. In addition, one or more residues extraneous to this sequence are fused to its N- or C-termini. These extraneous residues are particularly useful in forming covalent or noncovalent bonds between the N- and C-termini of this polypeptide. The N- and/or C-termini preferably are covalently bonded through a side chain of a residue or through the polypeptide backbone. For example, cysteine residues are fused to the N- and C-termini and, upon oxidation, a polypeptide having a terminal disulfide bond is formed which joins the terminal ends of the polypeptide, thereby conformationally restraining the polypeptide. Alternatively, the alpha amino group of the polypeptide (or that of an extraneous N-terminally located residue) is covalently bonded to the sulfur atom of an extraneous C-terminally located cysteine residue to form thioether cyclic compounds analogous to those depicted in Formula I. Other cyclic compounds are prepared in the same fashion as described elsewhere herein. Also within the scope of this embodiment are amino acid sequence variants of native IgE sequences corresponding to the sequence of this embodiment. Beta strand D variants are selected to enhance binding to FCEH, while the sequence outside of the beta strand D domain need only retain sufficient conformational structure to properly juxtapose the N- and C-termini in substantially the same position as is the case with the native IgE sequence.

The FCEH-specific polypeptides herein optionally comprise non-IgE polypeptides exactly as described above for the FCEL-specific polypeptides, except that it is not prefered that the FCEH-specific polypeptides comprise cytotoxic functionalities. In addition, conformationally restrained (typically cyclic) polypeptides comprising the FCEH-binding sequence of the beta strand D domain are included within the scope hereof. Such polypeptides are identical to those shown in Formula I above except that the FCEH-binding beta strand D domain replaces the (a3)-(a19) moiety. Exemplary replacement moieties include S420-R428, T421-N430, S420-G433 and R422-R428 (note that sequences such as T421-N430 from U266 that omit a residue from the Kabat sequence can contain a residue at that site or may have a deletion at the same location, in the latter case here the Asn residue would occupy site 429).

Any one or more of the AB-B domain residues also may be deleted in order to substantially reduce or eliminate FCEL binding. Residue deletion may be preferred for the same reason noted above with respect to the beta strand D domain.

Examples of candidate AB-B domain substitutional or deletional variants are set forth in the following Table 3. To determine the sequence of each variant, identify the residue for each variant number under each site. For example, the sequence of compound 98 comprises A383 A384 A385, and represents the class of mutations to which mutant 7 belongs.

TABLE 3

| | HuIgE Site | | | |
|---|---|---|---|---|
| AA[1] | 350 I | 351 R | 352 K | 353 S |
| C | | 55 | 19 | 37 |
| M | | 56 | 18 | 38 |
| F | | 57, 88 | 8, 80 | 39 |
| Y | | 4, 75, 83-84, 89, 97 | 7, 73 | 40 |
| W | | 58, 85 | 6 | 41 |
| P | | 59 | 1, 74, 78-79 | 42 |
| G | | 60, 73 | 5, 76-77 | 43 |
| A | | 61, 98, 102 | 12, 98-99 | 44, 98, 101 |
| V | 72 | 62 | 13, 97 | 45 |
| L | 73 | 63 | 14, 81 | 46 |
| I | 75 | 64 | 15, 82 | 47 |
| S | | 65, 103 | 16 | 1-2, 5-36, 55-72, 74, 76-91, 93-95, 97, 99-100, 102, 105 |
| T | | 66, 104, 105 | 17 | 49 |
| D | | 67, 86 | 9 | 50 |
| E | | 68, 87 | 89, 94 | 51 |
| N | 79 | 69 | 10 | 52, 79, 84 |
| Q | 1-71, 77, 78, 80-95, 97-103, 105 | 70 | 11, 103 | 3, 54, 75, 80, 82-83, 85-89, 103-104 |
| H | | 71 | 83, 104 | 4, 53 |
| K | 104 | 72, 79 | 2-4, 20-72, 75, 85-88, 91-93, 100-102, 105 | 48 |
| R | | 1-3, 5-54, 74, 76-78, 80-82, 90-92, 94, 99-101 | 84 | 73 |
| Δ[2] | 96 | 93, 95, 96 | 90, 95, 96 | 92, 96 |

[1]Amino acid residue substituted into the analogue
[2]Signifies a deletion.

Insertion of one or more extraneous residues adjacent to a residue within the AB-B domain also falls within the scope of this invention, although substitutions or deletions are preferred. Typically, only one residue will be inserted, although from 2 to 4 or more residues can be inserted adjacent to any one site within the AB-B domain. Smaller numbers of inserted residues will be preferred in order to avoid the introduction of immunogenic sites. This, however, is merely a matter of choice. In general, insertions will be made at a single site, although insertions can be made adjacent to any two or more AB-B domain residues.

Insertions typically are made between the following residues: S385 and P386, P386 and T387, T387 and I388, and I388 and T389. The inserted residue or residues generally will exhibit charge, bulk or hydrophobicity character which is distinct from that of the flanking residues. For example, candidate insertions can be selected from the following Table 4.

TABLE 4

| Insertion | AB-B domain site[1] |
|---|---|
| Q | 1, 2, 3, 4 or 5 |
| D | 1, 2, 3, 4 or 5 |
| E | 1, 2, 3, 4 or 5 |
| F | 1, 2, 3, 4 or 5 |
| W | 1, 2, 3, 4 or 5 |
| P | 1 or 2 |
| K | 2 or 3 |
| R | 2 or 3 |
| T | 3 or 4 |
| EK | 2 or 4 |
| ER | 2 or 4 |
| DK | 2 or 4 |
| DR | 2 or 4 |
| G | 1 or 2 |
| A | 5 |
| Y | 3 or 4 |
| N | 1, 2, 3, 4 or 5 |
| H | 1, 2, 3, 4 or 5 |
| I | 1, 2, 3, 4 or 5 |

[1]I382 site 1 - R383 - site 2 - K384 - site 3 - S385 - site 4 - P386 - site 5 - T387. Absence of a site indicates no insertion site.

One or more of the AB-B domain residues are substituted or deleted, or additional residues inserted adjacent to such residues. In general, no more than 4 residues or sites are varied and optimally only one will be varied. Variations herein include combinations of insertions, deletions or substitutions. Excluded from the scope of FCEH specific polypeptides are the linear IgE polypeptide fragments disclosed by Nio et al. (or the naturally occurring sequence variants of such fragments, e.g. alleles and the like), together with any other such fragments disclosed by the prior art.

Loop EF Variants

Loop EF is defined above. Loop EF variants not described in the examples may require screening against both FCEH and FCEL assays since loop EF is involved in both FCEL and FCEH binding. However, this screening will be routine and well within the ordinary skill when following the directions and principles herein. In general, FCEH or FCEL-binding differential polypeptides will comprise substitutions or deletions of (or insertions adjacent to) one or more of residues 446, 447, 448, 449, 450, 452 and 453. It should be noted that sites such as 446 and 447, while shown in the case of Ala substitution to lead to loss of FCEL binding (Example 5), also serve as sites for selecting variants which bind FCEL to a greater degree than native IgE. For the most part, however, sites 446 and 447 are not prefered for introducing variants in which the objective is FCEL binding. For this, one should focus on the region extending from residue 448 to 453, and preferably residues 450, 452 and 453. In general, loop EF variants are employed with variants introduced into loop AB—beta strand B or beta strand D or both.

R446 typically is substituted by Gly, Ala, Val, Leu, Ile, Ser, His, Lys, Met, Thr, Asp, Pro, Glu, Asn, Gln, Cys, Phe, Tyr or Trp, preferably Ala for FCEH specificity.

D447 generally is substituted by Gly, Ala, Val, Leu, Ile, Met, Cys, Ser, Thr, Pro, Glu, Asn, Gln, His, Lys, Arg, Phe, Tyr or Tip, preferably Ala for FCEH specificity.

W448 also generally is not substituted, but if so then Gly, Ala, Val, Leu, Ile, Met, Cys, Ser, Thr, Pro, Glu, Asn, Asp, Gln, His, Lys, Arg, Phe or Tyr are employed.

I449 likewise generally is not substituted, but if so then Gly, Ala, Val, Leu, Met, Cys, Ser, Thr, Pro, Glu, Asn, Asp, Gln, His, Lys, Arg, Phe, Tyr or Trp are employed.

E450 typically is substituted with Gly, Ala, Val, Ile, Leu, Met, Cys, Ser, Thr, Pro, Gln, Asn, Asp, His, Lys, Arg, Phe, Tyr or Trp, preferably Ala for FCEH specificity.

G151 generally is not substituted, but if so then Ala, Val, Leu, Met, Cys, Ser, Thr, Pro, Glu, Asn, Ile, Asp, Gln, His, Lys, Arg, Phe, Tyr or Trp are employed.

E452 also generally is substituted with Ala, Val, Leu, Met, Cys, Ser, Thr, Pro, Gly, Asn, Ile, Asp, Gln, His, Lys, Arg, Phe, Tyr or Trp.

T453 typically is substituted with Ala, Val, Leu, Met, Cys, Ser, Pro, Gly, Asn, Glu, Ile, Asp, Gln, His, Lys, Arg, Phe, Tyr, or Trp.

Exemplary IgE variants are set forth in Table 5. It will be understood that this table may contain variants that bind to both receptors, differentially to one or the other, or to neither receptor.

TABLE 5

| | HuIgE Site | | | | |
|---|---|---|---|---|---|
| AA[1] | 446 R | 447 D | 450 E | 452 E | 453 T |
| C | 47 | 46 | 45 | 44 | 43 |
| M | 34 | | | | |
| F | 33 | 25 | | | |
| Y | 41 | | | | 30 |
| W | | 26 | 36, 38 | | 36, 38 |
| P | | | 49 | | |
| G | | | | | |
| A | 13, 17 | 16 | 12, 15 | 12, 14 | 12 |
| V | | | | | 31 |
| L | | | | | 40 |
| I | | 48 | | | |
| S | | | | | 29 |

TABLE 5-continued

| | HuIgE Site | | | | |
|---|---|---|---|---|---|
| AA[1] | 446 R | 447 D | 450 E | 452 E | 453 T |
| T | 43 | | | | 1-3, 5-7, 9, 10, 13-17, 24-26, 28, 33, 34, 37, 39, 44-48, 50, 51 |
| D | 39 | 1, 2, 4-15, 17-23, 31-45, 47, 49-52 | 5, 8, 11, 18, 23, 27, 32, 33, 35, 40, 42, 52 | 1, 29, 30, 34, 50 | 42 |
| E | 9, 20 | 24, 29, 30 | 1-5, 7, 9, 10, 13, 14, 16, 17, 24-28, 30, 31, 34, 37, 39, 43, 44, 46, 47, 48, 51 | 3, 4, 6, 7, 9, 10, 13, 15-17, 24-26, 28, 31-33, 37, 39, 43, 45-49, 52 | 8, 11, 18-23, 27, 35 |
| N | 19, 22, 40 | 3 | 50 | 51 | |
| Q | 10, 11, 23, 35, 36, 42 | | | 2 | 52 |
| H | 21, 30 | 27 | | 36 | |
| K | 18, 28, 29, 52 | 28 | | 8, 11, 18-23, 27, 35, 40, 42 | 32 |
| R | 1-8, 12, 14-16, 24-27, 31, 32, 38, 44-46, 48-51 | 7 | 6 | 5 | 4 |
| Δ[2] | 37 | | | 38 | |

[1] amino acid residue substituted into the variant
[2] signifies a deletion

Variant Anti-huIgE Antibodies

Variant anti-huIgE antibodies were produced by first obtaining a group of murine monoclonal antibodies which were capable of binding to FCEL but not to FCEH. 8 such murine monoclonal antibodies, designated MAE10, MAE11, MAE12, MAE13, MAE14, MAE15, MAE16 and MAE17, were obtained by conventional methods involving immunizing mice with human IgE or a polypeptide consisting of residues 315-547 of huIgE and screening for anti-IgE activity.

MAE11/15 and MAE13 recognize different epitopes. It appears that the MAE13 epitope is located three-dimensionally adjacent to a key component of the FCEH binding site of IgE (but does not directly occupy that site) since a slight amount of histamine release will occur at high concentrations of MAE 13 suggesting that some limited antibody mediated crosslinking of FCEH occurs with MAE 13. MAE17 was most effective in suppressing B-cell IgE synthesis despite the fact that MAE11 and MAE13 exhibited greater IgE affinity. This may be attributed to its ability to mediate complement fixation (it possessed an IgG2a isotype, thus containing an Fc capable of eliciting effector function).

MAE11 and MAE15 are believed to recognize the same IgE epitope. Each antibody shared certain unusual features in its amino acid sequence. For example, CDR1 of the light chain of each contained 3 aspartic acid residues. CDR3 of the heavy chains of MAE11 and MAE15 contained 3 histidine residues (and contained two arginine residues, respectively).

Antibodies such as the foregoing having desired IgE binding characteristics may be further modified. Such modifications fall into two general classes. In the first class the antibodies are modified so that they are monovalent for IgE. This means that only one "arm" of the antibody, i.e., one light-heavy chain fork of the antibody, shall be capable of binding IgE. The remaining Fv "arm" of the antibody (or arms in the case of IgM) is specific for a second (non-IgE) antigen, is not capable of binding any antigen, or is deleted entirely. Thus, the term IgE monovalent covers polyvalent antibodies that are monovalent for IgE. The best results may be obtained with the second alternative, since this would preserve the structure of the antibody most faithfully and would likely confer the longest circulating half-life on the antibody. IgE-monovalent antibodies specific for FCEL bound IgE optimally will comprise sufficient Fc domains of the heavy chains to be capable of complement binding and Ig effector functions.

The second antigen recognized by one embodiment of IgE monovalent antibody is one which, when indirectly cross-linked to FCEL by the antibody herein, will not produce any toxic or deleterious response, i.e. the second antigen is not FCEH, and generally is, one which is not found in the animal to be treated (in order to avoid undesired absorption of the antibody onto tissues or proteins within the body). Thus, the second antigen ordinarily will not (but may be) FCEL. However, in some circumstances the second antigen will be a protein present in the patient to be treated, e.g. where such proteins are to serve as carriers or depot releases for the therapeutic antibodies herein.

Such IgE-monovalent antibodies are made by methods known per se. For example, DNA encoding the anti-IgE Fv heavy and light chains is ligated to DNA encoding the Fc of a human recipient antibody. In addition, DNA is provided that encodes heavy and light chains for an antibody capable of binding second antigen or an unidentified antigen, or that encodes heavy and light chain having sufficient residues deleted from the CDRs that non-IgE antigen binding no longer can occur. A conventional recombinant host is transformed with all four DNAs and the products recovered. Assuming random chain assortment, a subpopulation of antibody products will contain one arm with anti-IgE heavy and light chain and at least another arm having specificity for second antigen or no antigen. The desired subpopulation then is purified by conventional methods, e.g., immunoaffinity absorption or by molecular sieving. These antibodies also can be made by reduction of the starting antibodies followed by oxidative chain recombination, as has heretofore been employed in the preparation of monovalent antibodies (see for example Glennie et al., *Nature* 295:712 [1982]).

In addition to IgE-monovalency, in other embodiments the antibodies are modified so that they contain a maximum proportion of human sequence (commensurate with retention of required or desired activity), i.e., they are converted to chimeras or are humanized. In both instances the functional effect is to place the anti-IgE binding capability of the murine or other donor antibody into a human background to make it as non-immunogenic as possible.

General methods are known for making chimeras and for humanizing antibodies (as noted above). A minimal amount of non-human antibody sequence is substituted into the recipient human antibody. Typically, the non-human residues are substituted into the $V_H$, $V_L$, $V_H$-$V_L$ interface or framework of the recipient human antibody. Generally, the Kabat CDR's of the humanized antibodies are about 80% and more typically about 90% homologous with the non-human donor CDR's. The $V_H$-$V_L$ interface and framework residues of the humanized antibody, on the other hand, are about 80%, ordinarily 90% and preferably about 95% homologous with the recipient human antibody. Homology is determined by maximal alignment of identical residues. The resulting antibody is (a) less immunogenic in humans than a murine antibody and (b) capable of binding to FCEL-bound huIgE but substantially incapable of binding to FCEH-bound huIgE. Such antibodies typically comprise a human antibody which is substituted by an amino acid residue from a complementarity determining region (CDR), VL-VH interface or a framework region of a non-human anti-IgE antibody which is capable of binding. One or more, and preferably all, of the nonhuman CDR's L1, L2, L3, H1, H2 or H3 are substituted into the human antibody recipient.

The characteristics possessed by the MAE11 antibody were preferred for therapeutic use. Since MAE11 bound to soluble IgE, bound to MIge bearing B cells, blocked IgE binding to the low and high affinity IgE receptor, inhibited in vitro IgE production and failed to bond to IgE coated basophils, it was chosen as the donor antibody for humanization. The recipient antibody was Kabat human kappa (light) subgroup I and human subgroup III heavy chain, although it will be understood that any other human antibody can be suitably employed. Surprisingly, optimal results were not obtained by simply substituting the murine CDRs in place of the CDRs in a recipient human antibody (FIG. 3; Table 8 infra). Instead, it was necessary to restore donor framework hydrophobic residues such as $V_H$ 78, 48, 49, 63, 67, 69; 82 or 82c, or $V_L$ 13, 19, 58, 78 or 104, in order to achieve a degree of inhibition of IgE binding similar to that of the donor antibody. While these residues function to establish the conformation of CDRs, they generally are not exposed to the exterior of the antibody so use of the murine residues should not exert a significant impact on immunogenicity. Other non-CDR residues exerting an effect on binding included $V_H$60, 61, 37, 24, and $V_H$50, 52, 58 and 95 (non-CDR by Chothia), and $V_L$4, $V_L$33 (non-CDR by Chothia) and $V_L$53 (non-CDR by Chothia). The human framework hydrophobic residues generally are substituted with other hydrophobic residues (especially those from the donor antibody) such as valine, isoleucine, leucine, phenylalanine or methionine. The remaining non-CDR residues are substituted with any other amino acid residue, but again preferably the murine residue found at the analogous site.

In general, the character of the anti-IgE antibody is improved by substituting, deleting or inserting a residue at or adjacent to $V_L$ sites 30, 30b, 30d, 33, 55, 57, 58, 78, 93, 94, or 104 and/or $V_H$ residues 24, 37, 48, 49, 54, 57, 60, 61, 63, 65, 67, 69, 78, 82, 82c, 97, 100a or 100c.

Position $V_H$-78 is most preferably substituted with phenylalanine. However, it also is substituted with leucine, valine, isoleucine, methionine, alanine or any other residue which results in an improvement in the characteristics of the antibody (see infra).

Position $V_H$-60 is most preferably substituted with asparagine, although substitution with glutamine, histidine, lysine, arginine or any other residue which improves the characteristics of the antibody shall fall within the scope of this invention.

Position $V_H$-61 is most preferably substituted with proline, although glycine, alanine, valine, leucine, isoleucine or any other residue which results in an improvement in the characteristics of the antibody also is suitable.

CDR residues were imported from the donor MaE11. These included four inserts in $V_{L1}$, 30a-30d, as well as 91-94 ($V_{L3}$), $V_{H1}$ 27-29, 29a, 31, 33 and 34, $V_{H2}$53-55, and $V_{H3}$97-101. $V_L$ 30, 30b or 30d, as well as $V_H$97, 100a or 100c, are important in conferring on the CDR ability to bind IgE.

$V_H$ positions 97, 100a and 100c in humae11 (humanized Mae11) are all histidine, and 2 are arginine in MaE15. These residues are important in IgE binding. One, two or three of these are modified by substitution with basic residues, particularly lysine or arginine, but also with alanine, glycine, valine, isoleucine, serine, threonine, aspartic acid, glutamic acid, asparagine, glutamine, methionine, phenylalanine, tyrosine, tryptophan or proline.

$V_L$ positions 30, 30b and 30d of humae11 also are important for IgE binding. In humae11 each of these positions are occupied by the acidic residue, aspartic acid. They are substituted in other embodiments by glutamic acid, but also may be substituted with alanine, glycine, valine, isoleucine, serine, threonine, asparagine, glutamine, methionine, phenylalanine, tyrosine, tryptophan or proline. It is within the scope of this invention to reverse the charges on positions $V_L$ 30, 30b and 30d with those on $V_H$ 97, 100a and 100c, e.g. by employing aspartic acid residues in the three $V_H$ sites (2 in the case of humanized MaE15) and histidine in the three $V_L$ sites.

Residues also may be inserted adjacent to $V_H$ positions 97, 100a, 100c, 61 or 61, or $V_L$ residues at positions 30, 30b, 30d or 78. Inserted residues generally will be of like kind, e.g. an acid residue would be inserted adjacent to $V_L$-30, 30b or 30d, while a basic residue is inserted adjacent to $V_H$-97, 100 or 100c. The residues at these sites also may be deleted.

Humanized IgE-monovalent antibodies also are included within the scope of this invention. In this instance humanization extends to the anti-IgE arm as well, if necessary, to the remaining arm(s). Non-IgE binding arms of course can originate from human antibodies and in such case will not require humanization.

The foregoing variations are made by introducing mutations into the DNA encoding the precursor form of the antibody and expressing the DNA in recombinant cell culture or the like. This is accomplished by conventional methods of site directed mutagenesis. The variants then are screened for the desired character in assays conventional per se. In the case of anti-huIgE, desired character includes increasing the antibody affinity for huIgE, increasing its capacity and specificity for FCEL bound IgE, increasing the concentration of antibody required to stimulate histamine release from mast cells or basophils, reducing immunogenicity in humans, and other improvements apparent to the ordinary artisan. Optimizing these characteristics frequently will require balancing one improvement against another and therefore is a matter of judgment and is dependent upon the performance parameters dictated by the use intended for the antibody.

It is preferable to use a human IgG1 (or other complement fixing antibody) as the recipient immunoglobulin for humanization, although hu IgG2, IgG3, IgG4, IgE, IgM, IgD or IgA also can be used as recipient. Preferably the recipient is a complement fixing IgG antibody or an IgG antibody capable of participating in ADCC.

Therapeutic, Diagnostic and Preparatory Uses

The anti-IgE antibodies herein are useful in identifying IgE amino acid sequence variants in which the FCEL or FCEH-binding domains have been modified. Candidate FCEL or FCEH-specific polypeptides are incubated with these antibodies, and analogues to which these antibodies fail to bind are selected for further evaluation, e.g., determination, respectively of their FCEH and FCEL receptor binding characteristics. Any antibody, whether of murine, human, or another animal species in origin, or a variant thereof such as the humanized immunoglobulins described above, which has the epitopic specificity of any of antibodies MAE10-MAE17 (especially MAE11/15, MAE13 or MAE17) will be equally acceptable. Such antibodies are easily identified by immunizing a suitable animal or using an in vitro Fv selection system, e.g. phagemid, with IgE of the appropriate animal origin and screening the animals or products for antibodies having the ability to compete for IgE with MAE11/15, 13, 17 or other antibodies which map to substantially the same epitopic site(s) as those described herein. As noted, the antibodies desirably are monovalent for FCEL-bound IgE when employed therapeutically. They may be bivalent and/or bispecific when used to purify IgE from plasma, serum or recombinant cell culture.

The FCEH and FCEL-specific, differential binding polypeptides are useful for diagnostics and therapeutics. In in vitro diagnostic assays they are employed as specific binding reagents in assays for FCεRI or FCεRII, respectively. The polypeptides of this invention are labelled with a detectable substance such as an enzyme, fluorescent or chemiluminescent group, radioisotope or a specific binding moiety that binds to a detectable substance (such as an enzyme). A typical specific binding moiety is an immunoglobulin variable domain which is capable of binding to the detectable substance. FCEL and FCEH specific polypeptides comprising immunoglobulin variable domains are described in more detail above.

Assay systems that employ the FCEL or FCEH specific polypeptides of this invention are analogous to the sandwich-type systems heretofore generally used in the immunoassay field. Here, the specific polypeptide is employed in the same fashion as labelled antibodies directed against antigen (the FCEL or FCEH receptor) or as an absorption agent insolubilized on a matrix for the isolation of receptor from test sample. Redox, proteolytic, esterolytic or other conventional enzyme labels are conjugated to the polypeptides of this invention for use in conventional assay systems.

The differential binding polypeptides of this invention also are useful for the isolation of FCEL or FCEH from cell culture in preparing FCEL or FCEH for therapeutic or research purposes. The polypeptide is covalently bonded or noncovalently adsorbed to a matrix such as an ion exchange resin, an immunoaffinity column (containing an antibody capable of binding a polypeptide fused to the FCEH or FCEL-specific polypeptide), an immobilized antigen (where the FCEH or FCEL-specific polypeptide comprises an immunoglobulin variable region capable of binding to the antigen) or a cyanogen bromide activated polysaccharide. The immobilized FCEH or FCEL-specific polypeptide then is contacted with the receptor preparation under conditions such that the receptor is bound to the FCEH or FCEL-specific polypeptide. The receptor then is eluted by changing the pH or ionic conditions and separating the polypeptide preparation from the receptor.

The differential binding polypeptides herein are useful in preparing antibodies specific to the FCEH or FCEL-binding domain of IgE. For example, antibodies capable of binding specifically to the FCEH or FCEL-binding domains of IgE are selected by first immunizing a subject with IgE. Monoclonal antibodies then are selected in the ordinary way for native IgE binding, and the monoclonal antibodies then screened to identify those that bind to a FCEH or FCEL-specific polypeptide of this invention. Preferably the FCEH or FCEL-specific polypeptide will be identical in sequence to the corresponding sequence of the IgE used as immunogen except, of course, for the minimal mutations need to confer FCEH or FCEL differential binding specificity. For example, the IgE monoclonal antibodies can be selected for their inability to bind to mutation 6. If they are unable to bind to mutation 6 one can conclude that they bind to the FCEH-binding site and are therefore promising for use in diagnostic or therapeutic procedures that depend upon an antibody that fails to bind to FCEH-bound IgE but which binds to FCEL-bound IgE. Confirmation is obtained by determining that the antibody selected in fact binds to IgE bound to FCEL. Since the selected antibody is highly specific for the key site(s) involved in receptor binding it is then possible to reduce the size of the antibody; the bulk of the antibody is not needed for steric hinderance of the IgE-receptor interaction. Thus, it becomes feasible in allergy therapy to use anti-IgE monovalent antibodies or other anti-IgE fragments such as Fab, Fab' and the like.

Similarly, the FCEL or FCEH-specific polypeptides are useful as immunogens for raising antibodies capable of cross-reacting with native IgE only at epitopic sites outside of the domains varied in creating the FCEH or FCEL-specific polypeptides. For example, mutations 6 and 7 are useful for raising antibodies specific for IgE epitopes except for the mutated AB-B or beta strand B domains as the case may be.

The FCEH and FCEL-specific polypeptides and anti-IgE antibodies (especially those with reduced immunogenicity) are useful in therapies for the treatment or prophylaxis of allergies, although the FCEH specific polypeptide subgroup which bears cytotoxic functionalities is not considered suitable for therapy since it could lead to degranulation of mast cells and basophils. Otherwise, the polypeptides typically are administered to a patient who is known to be sensitized to an allergen, preferably prior to an acute allergic response.

The dosages and administration route will depend upon the accessory functionalities accompanying the polypeptides (e.g. cytotoxic agents, immunoglobulin effector functions, etc.), the condition of the patient (including the population of B cells or mast cells and basophils), the half-life of the polypeptide, the affinity of the polypeptide for its receptor and other parameters known to the clinician. As a general guide in the case of FCEH-specific polypeptide, one will determine from blood tests the amount of target cells circulating in the patient and determine the amount of polypeptide to displace or effectively compete with endogenous IgE taking into account the population of FCEH receptors as well as the half life and affinity of the polypeptide for FCEH. An excess of polypeptide calculated to be necessary to substantially displace native FCEH-bound IgE over a reasonable therapeutic interval will then be administered. Similar analysis used to determine the dosage of anti-IgE antibody or FCEL polypeptide.

Therapeutic polypeptides are administered by intravenous intrapulmonary, intraperitoneal subcutaneous or other suitable routes. Preferably the polypeptides are administered s.c. or i.v. over a period of about from 1 to 14 days as required. In the case of FCEL-specific polypeptide or anti-FCEL-bound IgE one would determine the amount needed to inhibit, suppress or kill a substantial portion of the IgE-secreting B cell population. Inhibition or suppression of the B cell population includes either or both of reductions in IgE secretion and attenuation of the total number of IgE secreting B cells. Candidate doses are readily determined by the use of in vitro cell cultures or animal models.

Therapy of allergic disorders with anti-FCEL bound IgE and FCEL or FCEH polypeptides optionally is accomplished with other known therapies for allergies. These include administration of gamma interferon, allergen desensitization, reduction in exposure to allergen, treatment with antihistamines and the like.

Preparation of FCEH- and FCEL-Specific Polypeptides

The FCEH- or FCEL-specific polypeptides of this invention are made in conventional fashion, i.e., modifications of amino acid sequence are accomplished by commonly available DNA mutagenesis methods such as PCR amplification using primers bearing the mutants, or by M13 mutagenesis, followed by expression of the mutated DNA in recombinant host cells. The polypeptides also can be made by Merrifield or other in vitro methods of synthesis if they are sufficiently small (generally, under about 100 residues). However, the polypeptides preferably are made by recombinant methods. Selection of recombinant host cells, vectors, culture conditions and other parameters are not believed to be critical. In general, hosts, vectors and methods heretofore used in the recombinant expression of immunoglobulins (generally, IgGs) are also useful for the preparation of the polypeptide sequences of this invention. Preferably, mammalian cells such as myelomas, CHO, Cos, 293s and the like are employed as hosts, and the vectors are constructed for secretory expression of the polypeptide. Recombinant expression systems facilitate the preparation of functional immunoglobulin variants containing FCEL- or FCEH-specific sequences since the host cells can be transformed with DNA encoding one heavy chain containing the FCEL- or FCEH-specific sequences and one light chain, each of which contains a variable domain for binding a first antigen, and an immunoglobulin that binds antigen and FCEL or FCEH recovered.

Similarly, the same process is used with DNA encoding in addition another heavy chain containing the FCEL- or FCEH-specific domain and another light chain, each of which contain a variable domain for binding a second antigen, and a bivalent immunoglobulin recovered. Properly assembled immunoglobulin analogues are recovered by affinity chromatography on a matrix containing the two antigen(s).

The polypeptides of this invention are recovered from lysed recombinant cell culture or (when secreted) the culture supernatant. Substantial purification is achieved by passing cell free extracts which contain the polypeptides over an immobilized FCEL or FCEH receptor affinity matrix. Other methods heretofore used to purify IgE or other appropriate immunoglobulins are equally acceptable here, including immunoaffinity and (when appropriate) absorption on immobilized antigen.

Polypeptides of this invention which contain short sequences preferably are prepared using solid-phase synthesis, e.g. the method of Merrifield, *J. Am. Chem. Soc.*, 85:2149 (1963). However, other equivalent chemical syntheses known in the art are acceptable. The recombinant or in vitro synthesized polypeptides then are cross-linked to matrices (for use in diagnostic or preparatory procedures) or are placed into conformationally restrained structures. Known cyclizing procedures such as those described in PCT 90/01331 or Lys/Asp cyclization using Nα-Boc-amino acids on solid-phase support with Fmoc/9-fluorenylmethyl (Ofm) side-chain protection for Lys/Asp, followed by piperidine treatment and cyclization, are useful. Methods which depend upon cross-linking or cyclization through residue side chains may require that an extraneous residue be inserted at the C and/or N terminus of the AB-B or beta stand D domains, as the case may be, to provide a suitable cyclizing or cross-linking site.

Glu and Lys side chains also have been crosslinked in preparing cyclic or bicyclic peptides: the peptide is synthesized by solid phase chemistry on a p-methylbenzhydrylamine resin, the peptide is cleaved from the resin and deprotected. The cyclic peptide is formed using diphenylyphosphorylazide in diluted methylformamide. For an alternative procedure, see Schiller et al., *Peptide Protein Res.* 25:171-77 (1985). See also U.S. Pat. No. 4,547,489.

Disulfide crosslinked or cyclized peptides are generated by conventional methods. The method of Pelton et al., *J. Med Chem.*, 29:2370-2375 (1986) is suitable. Also useful are thiomethylene bridges (*Tetrahedron Letters* 25:2067-2068 (1984). See also Cody et al., *J. Med Chem.* 28:583 (1985). The C390 residue found in the C-terminal sequence of the AB-B domain is useful in cross-linking or cyclizing this domain.

Typically, extraneous residues which are to participate in cyclization or cross-linking are inserted at the N- and C-termini of the chosen AB-B or beta strand D sequence as part of the synthesis of the polypeptide precursor to be employed in the procedure. The desired cyclic or cross-linked peptides are purified by gel filtration followed by reversed-phase high pressure liquid chromatography or other conventional procedures. The peptides are sterilized by 0.2 μm filtration and formulated into conventional pharmacologically acceptable vehicles.

The compounds described in this invention may be the free acid or base or converted to salts of various inorganic and organic acids and bases. Such salts are within the scope of this invention. Examples of such salts include ammonium, metal salts like sodium, potassium, calcium and magnesium; salts with organic bases like dicyclohexylamine-N-methyl-D-glucamine and the like; and salts with amino acids such as arginine or lysine. Salts with inorganic and organic acids may be like prepared, for example, using hydrochloric, hydrobromic, sulfuric, phosphoric, trifluoroacetic, methanesulfonic, maleic, fumaric and the like. Non-toxic and physiologically compatible salts are particularly useful although other less desirable salts may have use in the processes of isolation and purification.

A number of methods are useful for the preparation of the salts described above and are known to those skilled in the art. For example, reaction of the free acid or free base form of a compound of Formula I with one or more molar equivalents of the desired acid or base in a solvent or solvent mixture in which the salt is insoluble; or in a solvent like water after which the solvent is removed by evaporation, distillation or freeze drying. Alternatively, the free acid or base form of the product may be passed over an ion exchange resin to form the desired salt, or one salt form of the product may be converted to another using the same general process.

Additional pharmaceutical methods may be employed to control the duration of action of the polypeptides of this invention. Controlled release preparations are achieved through the use of polymers which complex with or absorb the subject polypeptides. Controlled delivery is achieved by formulating the polypeptides into appropriate macromolecular articles (for example, those prepared from polyesters, polyamino acids, polyvinyl, polypyrrolidone, ethylenevinylacetate, methylcellulose, carboxymethylcellulose, or polyamine sulfate).

Alternatively, instead of entrapping the polypeptides in polymeric matrices, it is possible to entrap these materials in microcapsules prepared, for example, by coacervation techniques or by interfacial polymerization. Hydroxymethylcellulose or gelatin microcapsules and poly-(methylmethacrylate) microcapsules, respectively, are useful, as are in colloidal drug delivery systems (for example, liposomes, albumin microspheres, microemulsions, nano-particles and nanocapsules). See *Remington's Pharmaceutical Sciences* (1980).

EXAMPLE 1

Preparation of Monoclonal Antibodies to IgE

Eight monoclonal antibodies with the ability to block the binding of IgE to the FCEH were used. These monoclonal antibodies, referred to as MAE10-MAE17, were made in the following manner. Purified human IgE was prepared from supernatants of U266B1 cells (ATCC® TIB 196) using affinity chromatography on a previously isolated anti-IgE antibody (Genentech MAE1, although other anti-hulge antibodies are equally useful). For MAE12, five BALB/c female mice, age six weeks, were immunized in their foot pads with 10 µg of the purified IgE in Ribi's adjuvant. Subsequent injections were done in the same manner one and three weeks after the initial immunizations. Three days after the final injection, the inguinal and popliteal lymph nodes were removed and pooled, and a single cell suspension was made by passing the tissue through steel gauze. For MAE14, MAE15, and MAE13 the immunizations were done in a similar manner except that for MAE13 30 µg of IgE per injection were used and IgE 315-547 was used as a prefusion boost; for MAE14 and MAE15 five injections of 50 µg each were used; and the IgE immunogen for MAE17 was IgE 315-547. For MAE10 and MAE11, injections were given subcutaneously in two doses of 100 µg and a final booster of 50 µg, and spleen cells were used for the fusions. The cells were fused at a 4:1 ratio with mouse myeloma P3X63-Ag8.653 (ATCC® CRL 1580) in high glucose (DMEM) containing 50% w/v polyethylene glycol 4000.

Fused cells were plated at a density of $2\times10^5$ per well in 96 well tissue culture plates. After 24 hours HAT selective medium (hypoxanthine/aminopterin/thymidine, Sigma Chemical Company, #H0262) was added. Of 1440 wells plated, 365 contained growing cells after HAT selection.

Fifteen days after the fusion, supernatants were tested for the presence of antibodies specific for human IgE using an enzyme-linked immunosorbent assay (ELISA). The ELISA was performed as follows, with all incubations done at room temperature. Test plates (Nunc Immunoplate) were coated for 2 hours with rat anti-mouse IgG (Boehringer Mannheim, # 605-500) at 1 µg/ml in 50 Mm sodium carbonate buffer, Ph 9.6, then blocked with 0.5% bovine serum albumin in phosphate buffered saline (PBS) for 30 minutes, then washed four times with PBS containing 0.05% Tween® 20 (PBST). Test supernatants were added and incubated two hours with shaking, then washed four times with PBST. Human IgE (purified from U266 cells as described above) was added at 0.5 µg/ml and incubated for one hour with shaking, then washed four times in PBST. Horseradish peroxidase conjugated goat anti-human IgE (Kirkegaard & Perry Labs, # 14-10-04, 0.5 mg/ml) was added at a 1:2500 dilution and incubated for one hour, then washed four times with PBST. The plates were developed by adding 100 µl/well of a solution containing 10 mg. of o-phenylenediamine dihydrochloride (Sigma Chemical Company # P8287) and 10 µl of a 30% hydrogen peroxide solution in 25 ml of phosphate citrate buffer Ph 5.0, and incubating for 15 minutes. The reaction was stopped by adding 100 µl/well of 2.5 M sulfuric acid. Data was obtained by reading the plates in an automated ELISA plate reader at an absorbance of 490 nm. For MAE12, 365 supernatants were tested and 100 were specific for human IgE. Similar frequencies of IgE specificity were obtained when screening for the other antibodies. All of the monoclonal antibodies described herein were of the IgG1 isotype except for MAE17, which was IgG2b, and MAE14, which was IgG2a.

Each of the IgE specific antibodies was further tested in cell-based and plate assays to select for antibodies which bound to IgE in such a way as to inhibit IgE binding to FCEH and which are not capable of binding to FCEH-bound IgE. The results of these assays are set forth in Table 6 and Table 6a below.

TABLE 6

SUMMARY OF MURINE Anti-Hu IgE mAb CHARACTERISTICS

| mAb | Immunogen | Schedule/ Dose (µg) | B-cell source | Isotype | % Binding FCEH-bound IgE[1] | PBL Histamine Release[2] (EC50) | Amount blocking FCEH[3] (EC50) |
|---|---|---|---|---|---|---|---|
| MaE 1 | PS IgE | 3 × 50 | Lymph Node | IgG1 | .05 µg/ml | 1 µg/ml | 0.3 µg |
| MaE 10 | U266 IgE | 2 × 100, 1 × 50 | Spleen | IgG1 | No binding at 10 µg/ml | >100 µg/ml | 2.5 µg |
| MaE 11 | U266 IgE | 2 × 100, 1 × 50 | Spleen | IgG1 | No binding at 10 µg/ml | >100 µg/ml | 0.6 µg |

TABLE 6-continued

SUMMARY OF MURINE Anti-Hu IgE mAb CHARACTERISTICS

| mAb | Immunogen | Schedule/ Dose (μg) | B-cell source | Isotype | % Binding FCEH-bound IgE[1] | PBL Histamine Release[2] (EC50) | Amount blocking FCEH[3] (EC50) |
|---|---|---|---|---|---|---|---|
| MaE 12 | U266 IgE | 3 × 30 | Lymph Node | IgG1 | No binding at 10 μg/ml | >100 μg/ml | 0.8 μg |
| MaE 13 | U266 IgE | 3 × 30 | Lymph Node | IgG1 | No binding at 10 μg/ml | >10 μg/ml | 0.6 μg |
| MaE 14 | U266 IgE | 5 × 50 | Lymph Node | IgG2a | No binding at 10 μg/ml | >100 μg/ml | 2.5 μg |
| MaE 15 | U266 IgE | 5 × 50 | Lymph Node | IgG1 | No binding at 10 μg/ml | >100 μg/ml | 0.6 μg |
| MaE 16 | rHIgE aa 315-547 | 5 × 1 | Lymph Node | IgG1 | No binding at 10 μg/ml | >100 μg/ml | 0.7 μg |
| MaE 17 | rHIge aa 315-547 | 5 × 1 | Lymph Node | IgG2b | No binding at 10 μg/ml | >100 μg/ml | >5.0 μg |

TABLE 6a

Summary of murine Anti-Hu IgE mAb (continued)

| mAb | % Binding to Membrane IgE on U266BL (EC50)[4] | % Binding of IgE on FcErII(CD23) IM9 (EC50)[5] | Blocks 1 μg IgE binding to FcER II (EC 50)[6] | Inhibition of in-vitro IgE synthesis[7] | Affinity constant for IgE[8] (Kd) |
|---|---|---|---|---|---|
| MaE 1 | 0.4 μg/ml | .05 μg/ml | >100 μg | (−) | $5.4 \times 10^{-8}$ |
| MaE 10 | 0.5 μg/ml | No binding at 10 μg/ml | 2.5 μg | (−) | $7 \times 10^{-9}$ |
| MaE 11 | 0.15 μg/ml | No binding at 10 μg/ml | 0.6 μg | (+) | $3 \times 10^{-8}$ |
| MaE 12 | >10 μg/ml | 1 μg/ml | 5.0 μg | (−) | $4 \times 10^{-7}$ |
| MaE 13 | 1 μg/ml | No binding at 10 μg/ml | 0.7 μg | (++) | $5 \times 10^{-8}$ |
| MaE 14 | 6 μg/ml | No binding at 10 μg/ml | 2.5 μg | (±) | $1.4 \times 10^{-8}$ |
| MaE 15 | 6 μg/ml | No binding at 10 μg/ml | 0.6 μg | (±) | $7 \times 10^{-8}$ |
| MaE 16 | 10 μg/ml | <.05 μg/ml | 5 μg | (+) | ND |
| MaE 17 | 10 μg/ml | No binding at 10 μg/ml | 5 μg | (++) | ND |

1. FACS Based Assays for Analysis of Murine Anti-Human IgE Monoclonals. Screen of Murine Anti-Human IgE Monoclonal Binding to IgE on CHO 3D10 (FcERI Alpha+)

a. CHO 3D10 cells (FcERI alpha chain stable transfectant; Hakimi et al., J. Biol. Chem. 265:22079) at 5×10⁵ cells per sample are incubated with U266 IgE standard (lot no. 13068-46) at 10 μg/ml in 100 μl FACS buffer (0.1% BSA 10 mN sodium azide in PBS pH 7.4) for 30 minutes at 4° C. followed by one wash with FACS buffer. The amount of IgE binding is determined by incubating an aliquot of IgE loaded cells with a polyclonal FITC conjugated rabbit anti-human IgG (Accurate Chem. Co. AXL-475F, lot no 16) at 50 μg/ml for 30 minutes at 4° C. followed by three washes with FACS buffer.

b. IgE loaded cells are incubated with 100 μl of murine anti-human IgE hybridoma supernatant (murine IgG concentration ranging from 1 to 20 μg/ml) for 30 min. at 4° C. followed by one wash with FACS buffer. A Genentech monoclonal anti-human IgE (MAE1) at 10 μg/ml is used as a positive control for binding. Genentech monoclonal (MAD 6P) which does not recognize IgE is used at 10 μg/ml as a negative control.

c. Monoclonal binding to human IgE on CHO cells is detected by incubating cells with 20 μg/ml FITC-conjugated, affinity purified F(ab) 2 Goat anti-mouse IgG (Organon Teknica cat. no. 10711-0081) for 30 minutes at 4° C. followed by three washes with FACS buffer. Cells are added to 400 μl buffer contain 2 μg/ml propidium iodide (Sigma cat no. P4170) to stain dead cells.

d. Cells are analyzed on a Becton Dickinson FACSCAN flow cytometer. Forward light scatter and 90 degree side scatter gates are set to analyze a homogeneous population of cells. Dead cells which stain with propidium iodide are excluded from analysis. Hybridoma supernatants which do not bind IgE on CHO 3D10 cells were considered candidates for further screening.

2. Histamine Release from Peripheral Blood Basophils:

Heparinized blood was obtained from normal donors and diluted 1:4 in a modified Tyrodes buffer (25 mM tris, 150 mM NaCl, 10 mM $CaCl_2,MgCl_2$, 0.3 mg/ml HSA, pH 7.35) then incubated with 1 nM human IgE (ND) at 4° C. for 60 minutes. Cells were then added to Tyrodes buffer containing either the murine monoclonal anti-IgE Abs (10 mg/ml) or a polyclonal anti-human antiserum as the positive control, and incubated at 37 C for 30 minutes. Cells were pelleted, histamine in supernatants was acetylated and histamine content was determined using an RIA kit (AMAC, Inc. Wesbrook, Main). Total histamine was determined from cells subjected to several rounds of freezed thawing. Percent histamine release was calculated as nM histamine content in supernatant—nM histamine spontaneously released divided by nM total histamine in the sample.

3. Blocking of Fitc Conjugated IgE Binding to FcERI Alpha Chain.

The effect of the antibodies on IgE binding was studied by preincubating Fitc labelled IgE with the various Mae antibodies at 37° C. for 30 minutes in PBS containing 0.1% BSA and 10 mM Sodium Azide pH 7.4, then incubating the complex with $5 \times 10^5$ 3D10 cells at 4° C. for 30 minutes. The cells were then washed three times and mean channel fluorescence at 475 nM was measured. A murine anti-human IgE mAb (Mae1) which does not block IgE binding to the FcERI alpha chain was used as a control.

4. Analysis of Murine Anti-Human IgE Binding to Membrane IgE Positive B Cell U266 a. U266 B1 cells (membrane IgE+) are cultured in base medium supplemented with 15% head inactivated fetal calf serum (Hyclone cat No. A-1111-L), penicillin, streptomycin (100 units/ml) and L-glutamine (2 mM).

b. Cells ($5 \times 10^5$/aliquot) are incubated in 100 µl FACS buffer containing murine anti-Human IgE monoclonals at 10, 5, 1, 0.5, and 0.1 µg/ml for 30 minutes on ice in 96 well round bottom microtiter plates followed by two washes with FACS buffer. The Genentech monoclonal MAE1 is used as a positive control.

c. Cells are incubated in 100 µl FACS buffer containing 50 µg/ml (1:20 stock) FITC conjugated F(ab') 2 affinity purified goat anti-mouse IgG (Organon Teknika Cat. No. 1711-0084) for 30 minutes on ice followed by three washes with FACS buffer. Cells are added to 400 µl FACS buffer containing propidium iodide at 2 µg/ml to stain dead cells.

5. FACS Based Binding Assays to FcERII(CD23+) B Cell IM9 a. FACS analysis of IgE binding to FcERII(CD23) (+) B cell line IM9. The IM9 human B cell myeloma ATCC CCL 159. (*Ann. N.Y. Acad. Sci.*, 190:221-234 [1972]) was maintained in GIF base medium with 10% heat inactivated fetal bovine serum, penicillin, streptomycin (100 units/ml) and L-glutamine (2 mM).

b. Cells ($5 \times 10^5$ aliquot) were incubated in 100 µl of FACS buffer containing U266 IgE standard at 2 µg/ml for 30 minutes at 4° C. in 96 well microtiter plates followed by 2 washes with FACS buffer. As a control, cells were incubated in buffer alone or buffer containing 2 µg/ml human IgG1 (Behring Diagnostics Cat. no. 400112, lot no. 801024).

c. Cells were then incubated with murine anti-human IgE monoclonals at 0.1 to 10 µg/ml for 30 minutes on ice. Genentech monoclonal MAE1 was used as a positive control.

d. Cells were incubated in 100 µl FACS buffer containing FITC conjugated F(ab')$_2$ goat anti-mouse IgG at 50 µg/ml (Organon Teknika Ca #1711-0084) for 30 minutes at 4° C. followed by 3 washes with FACS buffer.

e. Cells were added to 400 µl buffer containing propidium iodide at 2 µg/ml to stain dead cells.

f. Cells were analyzed on a Becton Dickinson FACSCAN flow cytometer. Forward light scatter and 90 degree side scatter gates were set to analyze a homogeneous population of cells and dead cells which stained with propidium iodide were excluded from analysis. FITC positive cells (IgE binding) were analyzed relative to cells stained with FITC rabbit anti-Human IgE alone.

g. As a positive control to determine the level of CD 23 on the surface of IM9 cells in each experiment, an aliquot of cells was stained with Becton Dickinson murine monoclonal Leu 20 (anti-CD23) at 10 µg/ml for 30 minutes at 4° C. followed by 2 washes. The cells were then incubated with FITC conjugated F(ab)$_2$ affinity purified goat anti-murine IgG at 50 µg/ml.

6. Antibody Blocking of Fitc Conjugated IgE Binding to the Low Affinity IRE Receptor.

The binding of 40 nM FITC labelled IgE to the low affinity IgE receptor (CD23) expressed on the B lymphoblast cell IM-9 was analyzed by flow cytometry on a FACSCAN flow cytometer. The effect of the antibodies on Fitc IgE binding was studied by preincubating Fitc IgE with the murine anti-human antibodies at 0.1 to 10 µg/ml. chimera at 37° C. for 30 minutes in PBS containing 0.1% BSA and 10 mM Sodium Azide pH 7.4, then incubating the complex with $5 \times 10^5$ cells at 4° C. for 30 minutes. The cells were then washed three times and mean channel fluorescence at 475 nM was measured.

7. IgE In Vitro Assay Protocol a. Peripheral blood mononuclear cells were separated from normal donors.

b. Cells were washed extensively with phosphate buffered saline to remove as many platelets as possible.

c. Mononuclear cells were counted and resuspend in media at $1 \times 10^6$ cells/ml. (Media=DMEM+pen/strep+15% horse serum+IL-2 (25 U/ml)+IL-4 (20 ng/ml)).

d. Antibodies were added at appropriate concentrations on day 0, 5, and 8.

e. Cultures were incubated in 24 well Falcon tissue culture plates for 14 days.

f. On day 14 supernatants were removed and assayed for IgE concentrations by an IgE specific ELISA protocol.

8. Affinity Constant (kd) of Murine mAb for Human IgE was Determined by Equilibrium Binding (Scatchard Analysis as Follows:

a. IgE (ND and PS allotypes were iodinated by the chloramine T method and separated from free $^{125}$I Na with a PD10 sephadex G25 column (Pharmacia cat. no. 17-0851-01) in RIA buffer:PBS, 0.5% bovine-serum albumin (Sigma cat. no. A-7888), 0.05% Tween 20 (Sigma cat. no. P-1379), 0.01% thimerosal (Sigma cat. no. T-5125), pH 7.4. Approximately 78-95% of the post column counts were precipitated with 50% trichloroacetic acid and specific activity of iodinated IgE preparations ranged from 1.6 to 13 µCi/µg assuming 70% counting efficiency.

b. A fixed concentration of $^{125}$I IgE (approximately $5 \times 10^4$ cpm) was added to varying concentrations of unlabelled IgE (1 to 200 nM) in a final volume of 0.1 ml RIA buffer in 12×75 mm polypropylene test tubes. Murine anti-human IgE mABs (20 nM final concentration) in 0.1 ml RIA buffer were then added for a final assay volume of 0.2 ml.

c. Samples were incubated 16-18 hours at 25° C. with continuous agitation.

d. Bound and free $^{125}$I IgE was separated by the addition of a 0.3 ml mixture of affinity purified goat anti-mouse IgG (Boehringer Mannheim cat. no. 605 208) coupled to CN Br activated Sepharose 4B (cat No. 17-0430-01) and carrier protein A sepharose (Repligen cat. No. IPA 300) in RIA buffer and incubated 1 to 2 hours at 25° C. with continuous agitation. RIA buffer (1 ml) was then added, and tubes were centrifuged 5 min. 400×g. Samples were counted to determine total counts. Supernatants were aspirated with a finely drawn pasteur pipet, samples were recounted and bound versus free counts were calculated.

e. Scatchard analysis was performed utilizing a Fortran program (scanplot) based on the Ligand program written by P. Munson at NIH. Scatplot uses a mass action equation fitting bound as a function of total using the Rodbard type regression analysis.

EXAMPLE 2

Preparation of Variant IgE

Based on the model of IgE Fc by Padlan & Davies (Mol. Immunol. 23:1063 (1986), which is based on the crystal structure of human IgG1 Fc (Deisenhofer, *Biochem.* 20:2361-2370 [1981]), a series of mutants were designed which could be used to test the binding of human IgE to its receptors. These mutants are designated Emut 1-13, and are listed in Table 7 below. The Fcε3 domain is comprised of seven β-strands which form a β-sheet structure representative of all immunoglobulin domains; there are six loops which connect these seven β-strands. We refer to these loops by the 2 β-strands they connect, e.g. loop AB connects β-stands A and B. We have constructed mutants of human IgE in which we have substituted five of the Fcε3 domain loops with their counterparts from human IgG1 (Table 7, 1-5). The sixth loop contains the glycosylation site in both IgE and IgG and hence was not altered. One mutant, (Table 7, 6), was made by exchanging human Fcε3 β-strand D with its human IgG1 Fcgamma2 counterpart. Seven additional mutants, (Table 7, 7-13), consisted of the substitution of Ala residues into Fcε3 β-strands and a loop in Fcε2.

A human IgE gene was cloned from U266, a publicly available cell line. The gene was cloned into a previously described phagemid vector containing the human cytomegalovirus enhancer and promoter, a 5' intron and sv40 polyadenylation signal (Gorman et al., *DNA and Prot. Eng. Techn.*, 2:3-10 [1990]). Mutagenesis was performed by the Kunkel method (T. A. Kunkel, *Proc. Natl. Acad. Sci. USA*, 82:488-492 (1985) using buffers and enzymes supplied with the BioRad Muta-gene phagemid in vitro mutagenesis kit, together with oligonucleotides encoding the human IgG1 sequences shown in Table 7 below. Sequences of the mutant IgE DNAs were checked only at the site of mutation using $^{35}$S dideoxy sequencing.

TABLE 7

| Mutant | Kabat Residue No. (Structure)[1] | Human IgeE Fcε3 Seq. | Human IgG1 Fcγ2 Seq. |
|---|---|---|---|
| 1 | 377-385 (1AB) | FDLFIRKS (SEQ ID NO: 10) | KDTLMISRT (SEQ ID NO: 11) |
| 2 | 396-401 (1BC) | APSKGT (SEQ ID NO: 12) | SHEDPQ (SEQ ID NO: 13) |
| 3 | 407-420 (1CD) | SRASGKPVNHS (SEQ ID NO: 14) | YVDGVQVHNAK (SEQ ID NO: 15) |
| 4 | 444-453 (1EF) | GTRDWIEGET (SEQ ID NO: 16) | LHQDWLDGKE (SEQ ID NO: 17) |
| 5 | 465-469 (1FG) | RALM (SEQ ID NO: 18) | APIE (SEQ ID NO: 19) |
| 6 | 423-428 (βD) | KEEKQR (SEQ ID NO: 20) | PREQQY (SEQ ID NO: 21) |
| 7 | 383-385 (1AB) | RKS | [AAA][2] |
| 8 | 387, 389 (βB) | T(I)T | [A(I)A][2] |
| 9 | 403, 405 (βC) | N(L)T | [A(L)A][2] |
| 10 | 438-440 (βE) | T(S)T | [A(S)A][2] |
| 11 | 455, 457, 459 (βF) | Q(C)R(V)T (SEQ ID NO: 22) | [A(C)A(V)A][2] (SEQ ID NO: 23) |
| 12 | 471, 473 (βG) | S(T)T | [A(T)A][2] |
| 13 | 329-331, 334-336 | QKH(WL)SDR (SEQ ID NO: 24) | [AAA(WL)AAA][2] (SEQ ID NO: 25) |

[1] loop = 1 B-strand = β
[2] Sequences in brackets are from mutants in which alanine residues rather than IgG sequences were used to replace the IgE target sequence. Residues in parentheses were not altered in these mutants.

The mutant IgEs were transiently expressed in human embryonic kidney 293 cells (Gorman et al., supra), purified on a mouse anti-human IgE antibody affinity column and samples run using SDS-PAGE to ascertain that the mutant proteins were of the proper molecular weight.

EXAMPLE 3

Soluble FCEH Binding Assay

This assay is a sequential inhibition ELISA which measures binding to the FCEH only. In this assay, a monoclonal antibody against the FCEH is coated onto ELISA plates at a concentration of 1 μg/ml in 50 mM sodium carbonate pH 9.6 for two hours at room temperature, and blocked for two hours with PBS containing 0.5% bovine serum albumin (PBSA), then washed three times with ELISA wash buffer (0.05% Tween 20 in PBS). Recombinantly produced soluble FCEH is added at a concentration of 50 units/ml and incubated for one hour, then washed five times in ELISA wash buffer. Mutant IgE samples are then added to the wells and incubated for one to two hours. The excess mutant IgE is removed by aspiration, and biotinylated IgE is then added at 50 ng/ml for 15 minutes followed by five washes with ELISA wash buffer. Streptavidin conjugated to horseradish peroxidase (Sigma Chemical Company #S5512) was added at a 1:5000 dilution for 15 minutes, then washed three times with ELISA wash buffer. Color was developed with a tetramethyl benzidine peroxidase substrate system (Kirkegaard &. Perry Labs # 50-76-00, Lot. no. NA 18) for seven minutes at 25° C. The reaction was stopped by the addition of 1 M HCl. The ability of the mutant IgE to bind the FCEH is assessed by the degree to which the biotinylated IgE is prevented from binding. This assay is designed to test for any FCEH binding by the mutant IgE and is not meant to determine the affinity of the mutant for the FCEH relative to native IgE.

FACS Based Binding Assays for U266 IgE Mutants

Tissue culture supernatants from 293s cells transfected with U266 IgE cDNA were harvested at either 48 or 96 hours post transfection. Tissue culture supernatants were concentrated 5-X with Amicon Centriprep 30® centrifugal concentrators (30,000 MW cutoff). Concentrated supernatants were passed through a mouse monoclonal anti-U266 IgE affinity column (Genentech MAE1 coupled to CnBr- Sepharose). U266 IgE was eluted from the column with 3.0 M potassium cyanate in 50 mM tris buffer Ph 7.8. Eluate fractions containing protein as determined by O.D. 280 nm were pooled and placed in Amicon Centricon 30® concentrators. Eluate buffer was exchanged for PBS by passing multiple volumes of PBS through the concentrator. The final volume of affinity purified supernatant ranged from 0.5-1 ml. Structural integrity of recombinant IgE mutants was analyzed on 1-12% SDS PAGE gels and compared with U266 IgE standard obtained from the U266 cell line. Mutants were also analyzed for the ability to bind to a series of monoclonal and IgE antibodies to further ascertain proper folding and structural identity with native IgE. The concentration of immunoreactive IgE for each IgE mutant was determined by a human IgE capture ELISA as follows. Nunc Immunoplate Maxisorp® plates (Nunc # 4-39451) were coated overnight at 4° C. with a Genentech murine IgG1 anti-U266 IgE (MAE1) at 1 µg/ml in coat buffer (50 mM sodium carbonate buffer pH 9.6). Coat antibody was removed by three washes with ELISA wash buffer (0.05% Tween 20 (US Biochemical Corporation # 20605) in PBS). Non-specific sites were blocked with ELISA diluent buffer (50 mM tris buffered saline containing 0.5% BSA (Sigma Chemical Company # A-7888), 0.05% Tween 20 and 2 mM EDTA) for two hours at 25° C. on an orbital shaker. Diluent buffer was removed with 3 washes of ELISA wash buffer. Serial two-fold dilutions of IgE mutants in ELISA diluent buffer were added to the plate. U266 IgE standard (lot 1306846) was added at 1000, 500, 250, 125, 62.5, 31.3, and 15.6 ng/ml in duplicate as standards. Samples and standard were incubated two hours at 25° C. followed by three washes with ELISA wash buffer. IgE was detected with HRP conjugated Sheep anti-human IgE (ICN # N060-050-1) at 1:8000 in ELISA diluent buffer for 90 min. at 25C followed by 3 washes with ELISA wash buffer. HRP conjugate was developed with a tetramethyl benzidine peroxidase substrate system (Kirkegaard & Perry Labs. # 50-76-00, Lot. no. NA 18) for 7 minutes at 25° C. The reaction was stopped by the addition of 1 M HCl. The reaction product was analyzed with a dual wavelength spectrophotometer at 450 nm minus absorption at 570 nm. The U266 IgE standards were used to generate a standard curve and IgE concentrations of the sample were extrapolated by non-parametric linear regression analysis.

FcERI alpha (+) CHO 3D10 (FCEH expressing) and FcERII(CD23) (+) IM9 (FCEL expressing) B cell lines were used for the binding assays. The stably transfected CHO (duk –) cell clone 3D10 (JBC 265, 22079-22081, 1990) was maintained in Iscove's modified Dulbecco's media supplemented with 10% heat inactivated fetal calf serum, 80 Itg/ml gentamicin sulfate and $5 \times 10^{-7}$ M methotrexate. The IM9 human B cell myeloma ATCC® CCL 159. (Ann. N.Y. Acad. Sci. 190:221-234, 1972) was maintained in GIF base medium with 10% heat inactivated fetal bovine serum, penicillin, streptomycin (100 units/ml) and L-glutamine (2 mM). As a positive control to determine the level of CD23 on the surface of IM9 cells in each experiment, an aliquot of cells was stained with Becton Dickinson murine monoclonal Leu 20 (anti-CD23) at 10 µg/ml for 30 minutes at 4° C. followed by two washes in FACS buffer. The cells were then incubated with FITC conjugated F(ab')$_2$ affinity purified goat anti-murine IgG at 5 µg/ml. Adherent CHO3D10 cells were removed from tissue culture dishes by incubation with 10 mM EDTA in PBS for 2 minutes at 37° C. Cells were counted, then resuspended in FACS buffer (0.1% BSA, 10 mM Na azide in PBS pH 7.4) at a concentration of $5 \times 10^6$/ml]. CHO3D10 and Im9 cells ($5 \times 10^5$/aliquot) were incubated in 100 µl of FACS buffer containing U266 IgE standard or IgE mutants at 2 µg/ml for 30 minutes at 4° C. in 96 well microtiter plates followed by two washes with FACS buffer. As a control, cells were incubated in buffer alone or buffer containing 2 µg/ml human IgG1 (Behring Diagnostics # 400112, lot no. 801024). Cells were then incubated in 100 µl FACS buffer containing FITC conjugated rabbit anti-human IgE at 20 µg/ml (Accurate Chem. Co. # AXL 475F, lot. no. 040A) for 30 minutes at 4° C. followed by 3 washes with FACS buffer. 400 µl of buffer containing propidium iodide at 2 µg/ml was added to the cell suspension to stain dead cells. Cells were analyzed on a Becton Dickinson FACS-CAN flow cytometer. Forward light scatter and 90 degree side scatter gates were set to analyze a homogeneous population of cells and dead cells which stained with propidium iodide were excluded from analysis. FITC positive cells (IgE binding) were analyzed relative to cells stained with FITC rabbit anti-H IgE alone.

The foregoing assays were used to determine the ability of the example 2 IgE analogues to bind to FCEH and FCEL. The results are set forth in Table 8.

TABLE 8

BINDING OF IGE AND IGE ANALOGUES TO FCEH AND FCEL

| Sample/Mutant | Conc. (ug/ml) | FCEH alpha % CHO 3D10 (+) | FCEL (CD23) % IM9 (+) |
|---|---|---|---|
| U266 IgE | 10 | 90.3 | 92.5 |
| U266 IgE | 5 | 89.9 | 82.6 |
| U266 IgE | 0.5 | 59.6 | 4.6 |
| U266 IgE | 0.1 | 15.8 | 1.7 |
| 1 | 1.65[1] | 1.7 | 4.3 |
| 2 | 1.65 | 34.3 | 48.9 |
| 3 | 1.65 | 32.3 | 1.2 |
| 4 | 1.65 | 4.9 | 9.2 |
| 5 | 1.65 | 60.5 | 73.9 |
| 6 | 1.65 | 1.4 | 71.6 |
| 7 | 1.65 | 76.4 | 4.6 |
| 8 | 1.65 | 70.3 | 16.3 |
| 9 | 1.65 | 84.2 | 94.3 |
| 10 | 1.65 | 67.5 | 84.8 |
| 11 | 1.65 | 70.8 | 61.5 |
| 12 | 1.65 | 84.7 | 90.3 |
| 13 | 1.65 | 85.7 | 96.1 |
| dh 184 (+) | 1.65 | 83.8 | 21.1 |
| PA13[2] (control) | 10 | 1.3 | |

[1] Values based on quantitative Elisa. U266 was used as the standard and murine anti-F$_{C\epsilon}$ monoclonal antibody to capture.
[2] A CDR grafted human IgG.

Three mutant IgEs exhibited complete loss of binding to the FCEH receptor: mutants 1, 4 and 6. Mutant 6 altered β-strand D at the end of Fcε3 close to the Fcε2 domain. Mutants 1 and 4 involved alteration of two Fcε3 loops which are adjacent and near the Fcε4 domain. Note that mutant 7 is subset of mutant 1 in which the three C-terminal residues of loop AB have been changed to alanines (Table 7, 1 vs. 7). However, mutant 7 does not affect binding to FCEH. We interpret this to mean that either 1) FcεRI binds at least one of IgE residues 377-381 or 2) the extra residue in IgG1 loop AB (9 residues) substituted for IgE loop AB (8 residues) effected deformation of some adjacent binding determinant, possibly loop EF. That mutants 8 and 10 had no affect on FcεRI binding most likely means that the FCEH receptor does not protrude into the cavity bounded by loop AB and β-strand D.

Although mutant 4 had a Leu replacing Gly444 (Table 7), this should not affect the conformation of loop EF. Residue 444 is prior to the N-terminus of this α-helix. In addition, murine IgE has a Val at position 444 and rat IgE has an Asp. The two buried hydrophobic residues in the middle of the α-helix, W448 and I449, are retained in the substituted IgG1 loop (W448, L449) as is G451 which terminated the α-helix. Hence the conformation of loop EF should be similar in IgE and IgG1.

Mutants 2 and 3 exhibited decreased binding to FCEH. Since loop BC lies near β-strand D and loop CD is in the vicinity of loop EF, it is conceivable that one or two residues in loops BC and CD contact FCEH.

Five mutant IgEs exhibited loss of binding to the FCEL receptor: mutants 1, 3 4, 7 and 8. Mutants 1 and 4 were discussed above. Mutant 3 involved alteration of loop CD; in contrast to FCEH, loop CD evidently plays a major role in FCEL binding. Mutant 7, a subset of mutant 1 as discussed above, comprises the C-terminal portion of loop AB and is proximal to loop EF. Additionally, mutant 8 consists of replacement of two Thr residues (387,389) with Ala; these two residues are part of β-strand B which is at the bottom of the aforementioned cavity bounded by loop AB and β-strand D. Mutant 10 comprised two different residues in this cavity (438,440) on β-strand E, which is adjacent to β-strand B. Since mutant 10 did not affect FCEL binding, we conclude that the FCEL receptor should have only a minimal incursion into cavity while the high affinity receptor does not intrude into the cavity.

In addition to a glycosylation site at Asn430 which corresponds to the glycosylation site in IgG Fc, human IgE contains another glycosylation site at Asn403. Mutant 9 converted Asn403 and Thr405 to alanines (Table 6). Loss of carbohydrate did not affect binding to either receptor.

Based on the information from mutants 1-13, we propose that FCEH and FCEL have binding sites on IgE Fc which are distinct but overlap. The low affinity receptor seems to interact with a relatively smaller portion of the IgE Fcε3 domain involving three adjacent loops: AB, CD and EF. In contrast, the high affinity receptor interacts with a larger portion of IgE Fcε3, which spans loop EF, β-strand D and, possibly, the N-terminal portion of loop AB. Portions of loops BC and CD in the vicinity of loop EF and β-strand D may also interact with FCEH. In addition, FCEL may protrude into the cavity bounded by loop AB and β-strand D whereas FCEH does not do so. Since we have not evaluated any mutants in FCε4 and only one in Fcε2 (mutant 13), it is possible that portions of these two domains play a role in IgE-receptor binding.

EXAMPLE 4

Preparation of Humanized MaE11

Residues were selected from MaE11 and inserted or substituted into a human Fab antibody background ($V_H$ region Kabat subgroup III and $V_L$ region kappa subgroup I). A first version, humae11v1 or version 1, is described in Table 9.

TABLE 9

Changes in $V_H$ human subgroup III and $V_L$ κ subgroup I (Kabat) consensus sequences for humanized MaE11 Version 1

| Domain | Hu Residue | Residue No. | V.1 | CDR by Kabat | CDR by Chothia |
|---|---|---|---|---|---|
| $V_L$ | M | 4 | L | | |
| | Insert | 30abcd | YDGD (SEQ ID NO: 26) | L1 | L1 |
| | L* | 33 | M | L1 | |
| | S | 53 | Y | L2 | |
| | Y | 91 | S | L3 | L3 |
| | N | 92 | H | L3 | L3 |
| | S | 93 | E | L3 | L3 |
| | L | 94 | D | L3 | L3 |
| $V_H$ | A | 24 | V | | |
| | F* | 27 | Y | H1 | H1 |
| | T | 28 | S | H1 | H1 |
| | F* | 29 | I | H1 | H1 |
| | Insert | 29a | T | H1 | H1 |
| | D | 31 | G | H1 | H1 |
| | A | 33 | S | H1 | H1 |
| | M* | 34 | W | H1 | H1 |
| | V | 37 | I | | |
| | V | 50 | S | H2 | |
| | S | 52 | T | H2 | |
| | N | 53 | Y | H2 | H2 |
| | G | 54 | D | H2 | H2 |
| | S | 55 | G | H2 | H2 |
| | Y | 58 | N | H2 | |
| | L | 78 | F | | |
| | D | 95 | G | H3 | |
| | | 97-101 | All Changed to MaE11 Sequence | H3 | H3 |

*These residues typically do not vary despite their position within CDRs. The remaining residues found in the KI and III CDR sequences (particularly the CDRs by Chothia structural analysis), will vary widely among recipient human antibodies.

Figure 4B:
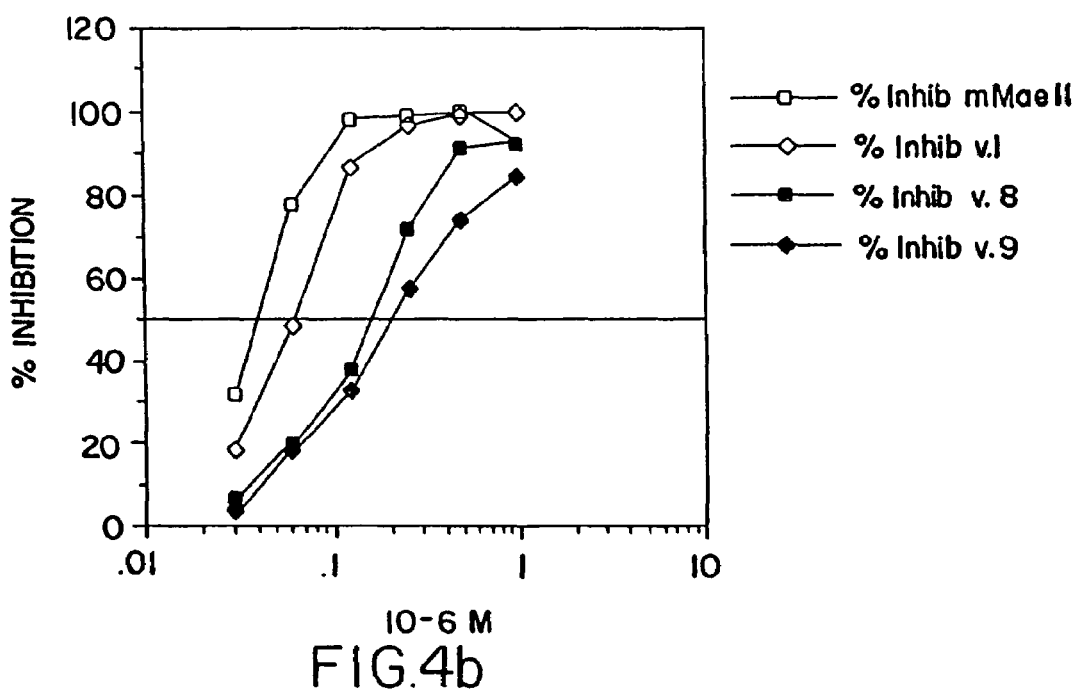
Figure 5B:
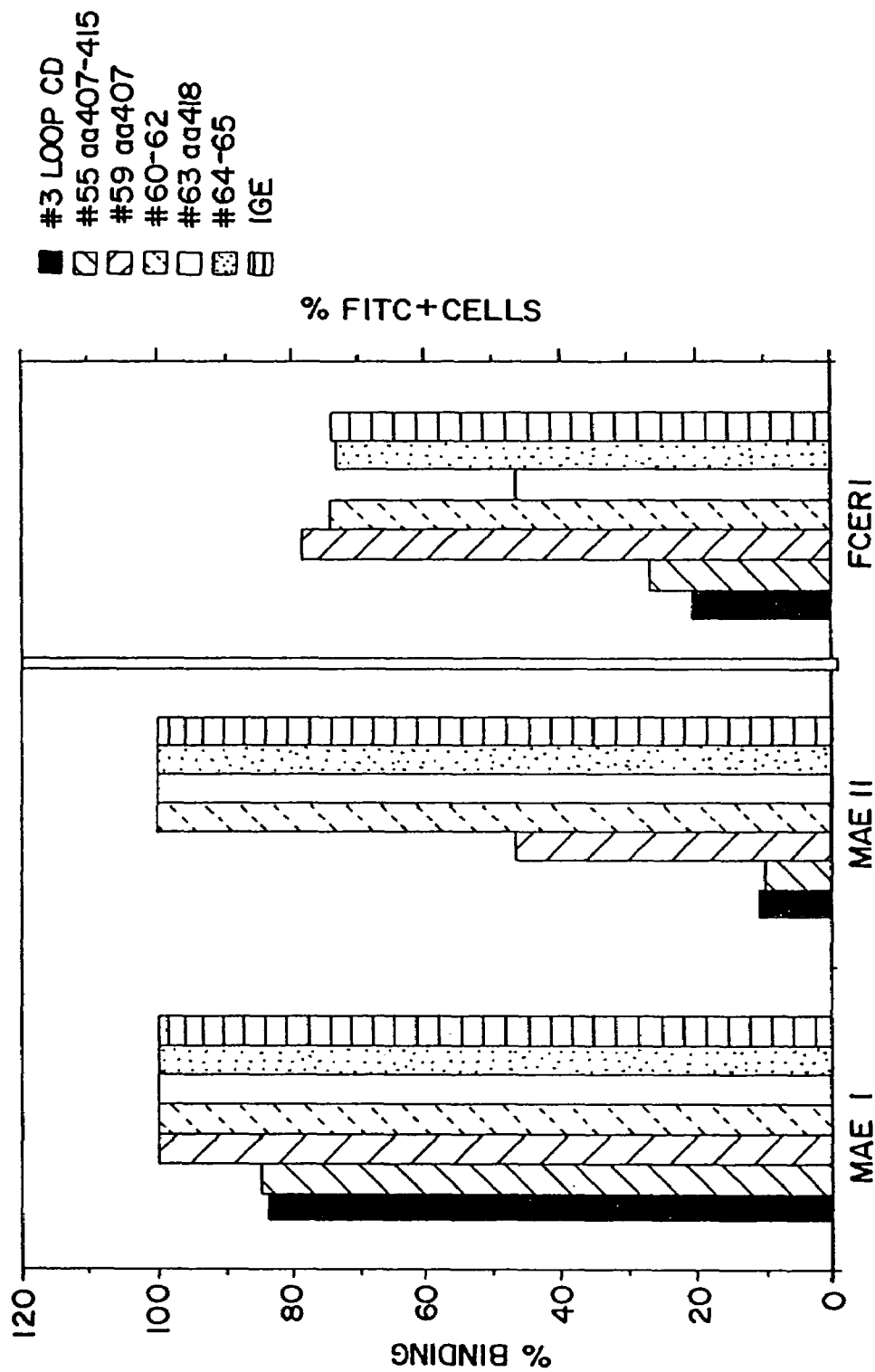
Figure 5C:
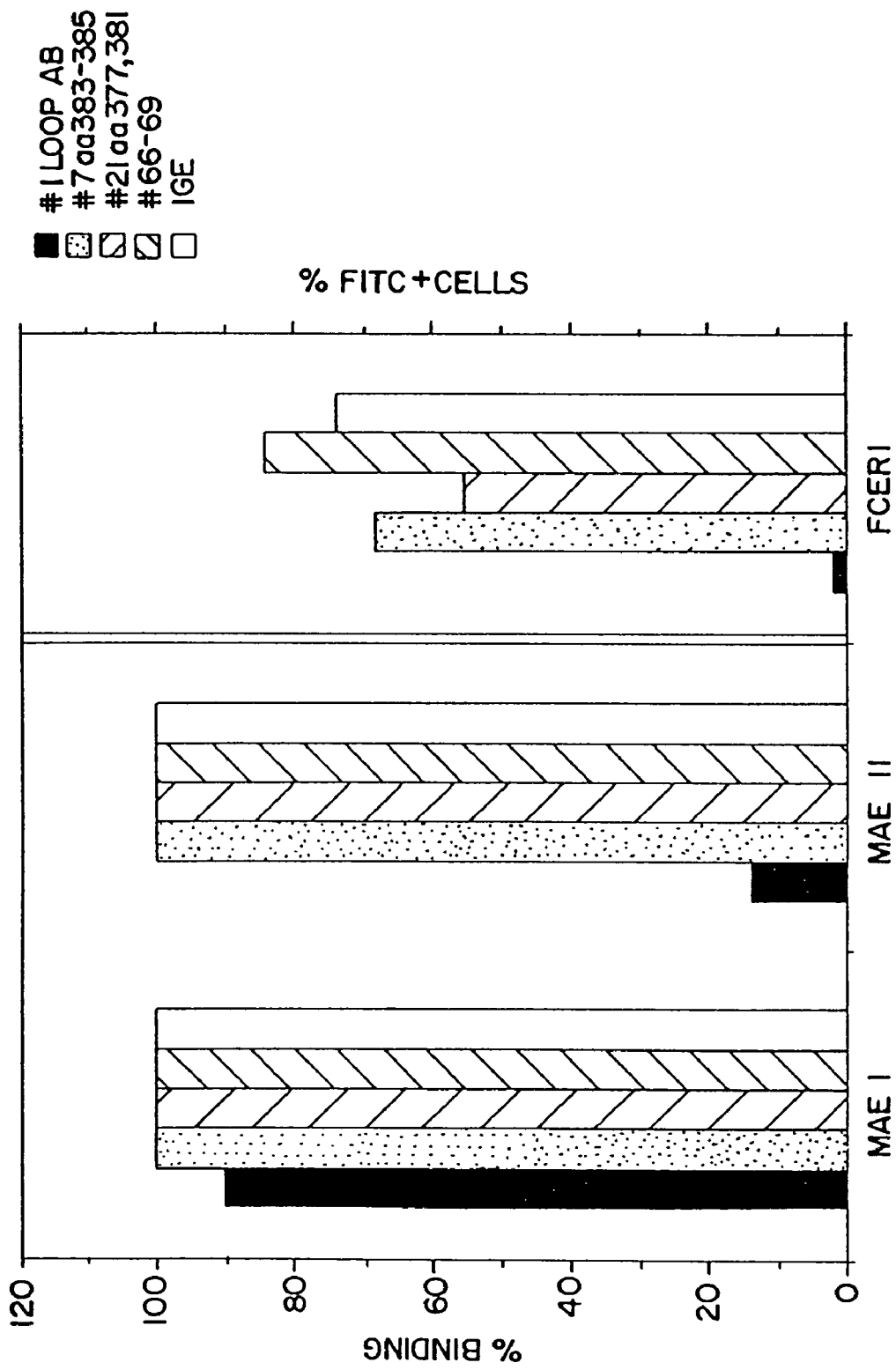

The affinity of version 1 was assayed and found to be about 100 times lower than that of the donor antibody Mae11 (see FIGS. 4a and 4b). Therefore, further modifications in the sequence of version 1 were made as shown in Table 10. Determination was made of the ability of these further modifications to inhibit the binding of labelled huIgE to FCEH.

The 50% inhibition assays whose results are shown in Table 10 were conducted as follows:

A 96-well assay plate (Manufn Nunc.) was coated with 0.05 ml of the FcεRI alpha chain IgG1 chimeric receptor in 1 μg/ml coating buffer (50 nmol carbonate/bicarbonate, pH 9.6). Assay was done for 12 hours at 4-8° C. The wells were aspirated and 250 μl blocking buffer (PBS—1% BSA pH 7.2) was added and incubated for one hour at 4° C. In a separate assay plate the samples and reference murine MaE11 antibody were titered from 200 μg/ml by 1 to 10-fold dilution with assay buffer (0.5% BSA, 0.05% Tween 20, PBS, pH 7.2) and an equal volume of 10 ng/ml biotinylated IgE at 10 ng/ml was added and the plate incubated for 2-3 hours at 25° C. The FcεRI-coated wells were washed three times with PBS-0.05% Tween20, and then 50 μl from the sample wells were transferred and incubated with agitation for 30 minutes at 25° C. 50 μl/well of streptavidin-HRP diluted 1:5000 in assay buffer was incubated for 15 minutes with agitation and then the plate was washed as before. 50 μl/well of Microwell peroxidase substrate (Kirkgaard & Parry Laboratories) was added and color was developed for 30 minutes. The reaction was stopped by adding an equal volume of 1 normal HCl and the adsorbance measured at 450 nm. The concentration for 50% inhibition was calculated by plotting percent inhibition versus concentration of blocking antibody with a nonlinear 4-parameter curve-fit for each antibody using INPLOT.

TABLE 10

Humanized MaE11 Variants

| Version [F(ab)-X] | Domain | Changes from F(ab)-Version 1 | Purpose | Conc. At 50% inh. (ng/ml)* Mean | S.D. for prev. col. | F(ab)-X/F(ab)-1 |
|---|---|---|---|---|---|---|
| 1 | — | — | — | 6083 | 1279 | 1.0 |
| 2 | $V_L$ | L4M M33L | Packing; CDR-L1 | 9439 | 508 | 1.6 |
| 3 | $V_L$ | E55G G57E | Sequence usually E55-X-G57 | 5799 | 523 | 1.0 |
| 4 | $V_H$ | I37V | VL-VH interface | 8622 | 107 | 1.4 |
| 5 | $V_H$ | V24A | Packing; CDR-H1 | 9387 | 733 | 1.6 |
| 6 | $V_H$ | F78L | Packing; CDR-H1, H2 | 17537 | 4372 | 2.9 |
| 7 | $V_L$ $V_H$ | L4M R24K E55G G57E V24A I37V T57S A60N D61P V63L G65N F78L | remake version 1 to accomplish a direct exchange of CDR residues | >100000 | | >16.0# |
| 7a | $V_H$ | As V.7 except $V_H$ L78 is F | | 98000 | | 16.0 |
| 8 | $V_H$ | A60N D61P | Extended Kabat CDR-H2 & A60N is at $V_L$-$V_H$ interface | 1224 | 102 | 0.20 |
| 8a | $V_H$ | As V.8 except $V_H$ V63 is L and F67 is I | CDR-H2; packing of L63 and I67 | 416 | 66 | 0.07 |
| 8b | $V_H$ | As V.8 except F67 is I | CDR-H2; packing of V63 and I67 | 501 | 84 | 0.08 |
| 9 | $V_L$ $V_H$ | A13V V19A V58I L78V V104L V48M A49G A60N V63L F67I I69V M82L L82cA | Repack Version 1 interior as in murine MaE11 | 842 | 130 | 0.14 |
| 23 | $V_L$ | L4M | Packing; CDR-L1 | 6770 | 349 | 1.1 |
| 1 | — | — | — | 6083 | 1279 | 1.0 |
| 10 | $V_L$ | D30A D30bA D30dA | CDR-L1 modification | >100000 | | >16.0 |
| 11 | $V_L$ | E93A D94A | CDR-L3 modification | 17456 | 7115 | 2.9 |
| 12 | $V_H$ | D54A | CDR-H2 modification | 2066 | 174 | 0.34 |
| 13 | $V_H$ | H97A H100aA H100cA | CDR-H3 modification | >100000 | | >16.0 |
| 14 | $V_L$ | D30A | CDR-L1 modification | 3452 | 183 | 0.57 |
| 15 | $V_L$ | D30bA | CDR-L1 modification | 6384 | 367 | 1.0 |
| 16 | $V_L$ | D30dA | CDR-L1 modification | >100000 | | >16.0 |
| 17 | $V_H$ | H97A | CDR-H3 modification | 19427 | 8360 | 3.2 |

TABLE 10-continued

Humanized MaE11 Variants

| Version [F(ab)-X] | Domain | Changes from F(ab)-Version 1 | Purpose | Conc. At 50% inh. (ng/ml)* Mean | S.D. for prev. col. | F(ab)-X/ F(ab)-1 |
|---|---|---|---|---|---|---|
| 18 | $V_H$ | H100aA | CDR-H3 modification | 2713 | 174 | 0.45 |
| 19 | $V_H$ | H100cA | CDR-H3 modification | 15846 | 8128 | 2.6 |

*Inhibition of fitc-IgE binding to FCEH (FcERI). Full-length antibody and humanized fragment versions: mean and standard deviation of three assays.
A F(ab)-X/F(ab)-1 ratio of >16 means that this variant exhibited no binding even at the highest F(ab) concentrations used.

As can be seen from Table 10 and FIGS. 4a and 4b, version 8 (in which human residues of version 1 at sites 60 and 61 in the light chain were replaced by their Mae11 counterparts) demonstrated substantially increased affinity. Further increases in affinity are seen in versions 8a and 8b, where one or two murine residues replaced human residues. Other increases, at least virtually to the level of Mae11, were accomplished by replacing hydrophobic human residues found in the interior of $V_H$ and $V_{H1}$ with their MaE11 counterparts, resulting in the variant designated version 9 (see Table 10 and FIGS. 4a and 4b). Accordingly, the humanized antibodies of this invention will possess affinities ranging about from 0.1 to 100 times that of MAE11.

Table 11 explores the effects on FCEH affinity of various combinations of humanized maE11 IgG1 variants.

TABLE 11

Humanized MaE11 IgG1 Variants

| Variant | Conc. at 50% inh. (ng/ml) Mean* | S.D. from previous column* | Var. X/ IgL1H1 | Var. X/ MaE11 |
|---|---|---|---|---|
| IgL1H1 | 7569 | 1042 | 1.0 | 16.9 |
| IgL1H8 | 3493 | 1264 | 0.46 | 7.8 |
| IgL9H9 | 1118 | 172 | 0.15 | 2.5 |
| IgL1H9 | 608 | 364 | 0.08 | 1.4 |
| IgL9H1 | 5273 | 2326 | 0.70 | 11.7 |
| IgL1H8b | 1449 | 226 | 0.19 | 3.2 |
| MaE11 | 449 | 53 | 0.06 | 1.0 |

*L1 = $V_L$ as in F(ab)-1 (human buried residues--not exposed to solvent);
L9 = $V_L$ as in F(ab)-9 (murine buried residues);
H1 = $V_H$ as in F(ab)-1 (human buried residues);
H8 = $V_H$ as in F(ab)-8 (F(ab)-1 with AlaH60Asn, AspH61Pro);
H9 = $V_H$ as in F(ab)-9 (murine buried residues);
H8b = $V_H$ as in F(ab)-8b (F(ab)-8 with PheH67Ile).

EXAMPLE 5

Creation of IgE Mutants

IgE mutants (Table 12) were prepared to evalute their effect on binding to anti-IgE, especially MaE11, and to FcεRI and FcεRII. Some of the mutants were designed to substitute for a specific amino acid residue another residue with either similar or very different charge or size. The impact of these changes on receptor binding is reflected in the table below.

The receptor assays are performed substantially as follows:

A 96-well assay plate (Manufn Nunc.) was coated with 0.05 ml of FcεRI or RII IgG1 chimeric receptor in 1 μg/ml coating buffer (50 nmol carbonate/bicarbonate, pH 9.6). Assay was done for 12 hours at 4-8° C. The wells were aspirated and 250 μl blocking buffer (PBS—1% BSA pH 7.2) was added and incubated for one hour at 4° C. In a separate assay plate the samples and reference murine MaE11 antibody were titered from 200 μg/ml by 1 to 10-fold dilution with assay buffer (0.5% BSA, 0.05% Tween 20, PBS, pH 7.2) and an equal volume of 10 ng/ml biotinylated IgE at 10 ng/ml was added and the plate incubated for 2-3 hours at 25° C. The FcεRI-coated wells were washed three times with PBS-0.05% Tween 20, and then 50 μl from the sample wells were transferred and incubated with agitation for 30 minutes at 25° C. 50 μl/well of streptavidin-HRP diluted 1:5000 in assay buffer was incubated for 15 minutes with agitation and then the plate was washed as before. 50 μl/well of Microwell peroxidase substrate (Kirkgaard & Parry Laboratories) was added and color was developed for 30 minutes. The reaction was stopped by adding an equal volume of 1 normal HCl and the absorbance measured at 450 nm. The absorbance was plotted versus concentration of blocking antibody MaE11 and an inhibition standard curve was generated using INPLOT.

TABLE 12

| Amino acid sequences of IgE mutants | | | | | |
|---|---|---|---|---|---|
| Mutant | Kabat Residue # | Human IgE Fce3 seq. | Mutant seq. | Fcε-RI* | FcεRII* |
| Loop AB | | | | | |
| 1 | 377-385 | FDLFIRKS (SEQ ID NO: 27) | KDTLMISRT (SEQ ID NO: 28) | - | - |
| 7 | 383-385 | RKS | AAA | +/-, - | +, - |

TABLE 12-continued

Amino acid sequences of IgE mutants

| Mutant | Kabat Residue # | Human IgE Fce3 seq. | Mutant seq. | Fcϵ-RI* | FcϵRII* |
|---|---|---|---|---|---|
| 21 | 377, 381 | F(DL)F (SEQ ID NO: 29) | Q(DL)H (SEQ ID NO: 30) | + | + |
| 66 | 382 | I | A | + | + |
| 67 | 383 | R | A | + | +/− |
| 68 | 384 | K | A | + | + |
| 69 | 385 | S | A | | |
| 102 | 383, 384 | RK | DD | | |
| β-strand B | | | | | |
| 8 | 387, 389 | T(I)T | A(I)A | +/−, + | − |
| 70 | 387 | T | A | + | +/−, + |
| 71 | 389 | T | A | + | + |
| Loop BC | | | | | |
| 2 | 396-401 | APSKGT (SEQ ID NO: 31) | SHEDPQ (SEQ ID NO: 32) | | |
| β-strand C | | | | | |
| 9 | 403, 405 | N(L)T | A(L)A | + | + |
| Loop CD | | | | | |
| 3 | 407-420 | SRASGKPVNHS (SEQ ID NO: 33) | YVDGVQVHNAK (SEQ ID NO: 34) | +/− | − |
| 55 | 407-415 | SR(A)S(G)K (SEQ ID NO: 35) | AA(A)A(G)A (SEQ ID NO: 36) | +/− | + |
| 59 | 407 | S | A | + | + |
| 60 | 408 | R | A | + | − |
| 61 | 411 | S | A | + | + |
| 62 | 415 | K | A | + | − |
| 63 | 418 | N | A | +/− | + |
| 64 | 419 | H | A | + | + |
| 65 | 420 | S | A | +/− | + |
| 100 | 408 | R | E | | |
| 101 | 415 | K | D | | |
| β-strand D | | | | | |
| 6 | 423-428 | KEEKQR (SEQ ID NO: 37) | PREQQY (SEQ ID NO: 38) | + | + |
| 35 | 422 | R | A | + | + |
| 36 | 4423 | K | A | + | + |
| 37 | 424 | E | A | + | + |
| 38 | 425 | E | A | + | + |
| 39 | 426 | K | A | + | |
| 40 | 427 | Q | A | −, +/− | + |
| 41 | 428 | R | A | + | + |
| 75 | 423-425 | KEE | AAA | −, +/−, + | + |
| 76 | 426-428 | KQR | AAA | | |

TABLE 12-continued

Amino acid sequences of IgE mutants

| Mutant | Kabat Residue # | Human IgE Fcε3 seq. | Mutant seq. | Fcε-RI* | FcεRII* |
|---|---|---|---|---|---|
| 79 | 423, 425, 427 | KEEKQR (SEQ ID NO: 39) | AEAKAR (SEQ ID NO: 40) | | |
| 80 | 424, 426, 428 | KEEKQR (SEQ ID NO: 41) | KAEAQA (SEQ ID NO: 42) | | |
| 81 | 423, | K | P | | |
| 82 | 423-427 | KEEKQR (SEQ ID NO: 43) | AAEAQA (SEQ ID NO: 44) | | |
| β-strand E | | | | | |
| 10 | 438, 440 | T(S)T | A(S)A | + | + |
| Loop EF | | | | | |
| 4 | 444-453 | GTRDWIEGET (SEQ ID NO: 45) | LHQDWLDGKE (SEQ ID NO: 46) | − | − |
| 49 | 445 | T | A | + | + |
| 50 | 336 | R | A | + | − |
| 51 | 337 | D | A | + | +, − |
| | | | | +/− | |
| 52 | 450 | E | A | + | − |
| 53 | 452 | E | A | + | + |
| | | | | + | +/− |
| 77 | 445, 446 | TR | AA | − | − |
| 78 | 450, 452, 453 | E(G)ET (SEQ ID NO: 47) | A(G)AA (SEQ ID NO: 48) | + + | + |
| 83 | 444 | G | L | + | + |
| 84 | 444 | G | A | | |
| 85 | 445-453 | TRDWIEGET (SEQ ID NO: 49) | HQDWLDGKE (SEQ ID NO: 50) | − + | + |
| 86 | 445 | T | H | + | |
| 87 | 445, 446 | TR | HQ | +/−, + | |
| 88 | 446 | R | E | − | |
| 89 | 450, 452, 453 | E(G)ET (SEQ ID NO: 51) | D(G)KE (SEQ ID NO: 52) | +/−, − + | +/− |
| 93 | 447 | D | R | +/−, − | |
| 94 | 450 | E | R | | |
| 95 | 452 | E | R | | |
| 96 | 453 | T | R | | |
| 97 | 447 | D | N | | |
| 98 | 452 | E | Q | | |
| 99 | 452 | E | D | | |
| β-strand F | | | | | |
| 11 | 445, 457, 459 | Q(C)R(V)T (SEQ ID NO: 53) | A(C)A(V)A (SEQ ID NO: 54) | | |
| Loop FG | | | | | |
| 5 | 465-469 | RALM (SEQ ID NO: 55) | APIE (SEQ ID NO: 56) | | |

TABLE 12-continued

Amino acid sequences of IgE mutants

| Mutant | Kabat Residue # | Human IgE Fcε3 seq. | Mutant seq. | Fcε-RI* | FcεRII* |
|---|---|---|---|---|---|
| β-strand G | | | | | |
| 12 | 471, 473 | S(T)T | A(T)A | +, + | |
| Fcε2 | | | | | |
| 13 | 329-331, 334-336 | QKH(WL)SDR (SEQ ID NO: 57) | AAA(WL)AAA (SEQ ID NO: 58) | +, + | |
| Fcε4 | | | | | |
| 72 | 498-501 | PRAA (SEQ ID NO: 59) | QPRE (SEQ ID NO: 60) | | |
| 73 | 594-599 | ASPSQT (SEQ ID NO: 61) | LHNHY (SEQ ID NO: 62) | | |
| 74 | 595-599 | S(P)SQT (SEQ ID NO: 63) | A(P)AAA (SEQ ID NO: 64) | | |

*Positive receptor binding indicated by "+", no binding by "−", and positive binding but less than unaltered is shown by "+/-". Where more than one assay was performed, results are separated by commas.

We claim:

1. An isolated nucleic acid molecule encoding a humanized antibody that specifically binds IgE comprising:
   (a) a VH domain and a VL domain, wherein:
      (i) the VH domain comprises the VH domain of SEQ ID NO:8 in which the alanine residue at position 61 of SEQ ID NO:8 is replaced by an asparagine residue, the aspartic acid residue at position 62 of SEQ ID NO:8 is replaced by a proline residue, the valine residue at position 64 of SEQ ID NO:8 is replaced by a leucine residue, and the phenylalanine residue at position 68 of SEQ ID NO:8 is replaced by an isoleucine residue, in which said positions correspond to Kabat numbering 60, 61, 63 and 67, respectively, and
      (ii) the VL domain comprises the VL domain of SEQ ID NO:9; or
   (b) a VH domain and a VL domain, wherein:
      (i) the VH domain comprises the VH domain of SEQ ID NO:8 in which the alanine residue at position 61 of SEQ ID NO:8 is replaced by an asparagine residue, the aspartic acid residue at position 62 of SEQ ID NO:8 is replaced by a proline residue, and the phenylalanine residue at position 68 of SEQ ID NO:8 is replaced by an isoleucine residue, in which said positions correspond to Kabat numbering 60, 61 and 67, respectively, and
      (ii) the VL domain comprises the VL domain of SEQ ID NO:9; or
   (c) a VH domain and a VL domain, wherein:
      (i) the VH domain comprises the VH domain of SEQ ID NO:8 in which the valine residue at position 49 of SEQ ID NO:8 is replaced by a methionine residue, the alanine residue at position 50 of SEQ ID NO:8 is replaced by a isoleucine residue, the alanine residue at position 61 of SEQ ID NO:8 is replaced by an asparagine residue, the valine residue at position 64 of SEQ ID NO:8 is replaced by an leucine residue, the phenylalanine residue at position 68 of SEQ ID NO:8 is replaced by an isoleucine residue, the isoleucine residue at position 70 of SEQ ID NO:8 is replaced by a valine residue, the methionine residue at position 83 of SEQ ID NO:8 is replaced by a leucine residue, and the leucine residue at position 86 of SEQ ID NO:8 is replaced by an alanine residue, in which said positions correspond to Kabat numbering 48, 49, 60, 63, 67, 69, 82 and 82c, respectively, and
      (ii) the VL domain comprises the VL domain of SEQ ID NO:9 in which the alanine residue at position 13 of SEQ ID NO:9 is replaced by a valine residue, the valine residue at position 19 of SEQ ID NO:9 is replaced by an alanine residue, the valine residue at position 62 of SEQ ID NO:9 is replaced by an isoleucine residue, the leucine residue at position 82 of SEQ ID NO:9 is replaced by a valine residue, and the valine residue at position 108 of SEQ ID NO:9 is replaced by a leucine residue, in which said positions correspond to Kabat numbering 13, 19, 58, 78 and 104, respectively.

2. The nucleic acid of claim 1, wherein the encoded antibody is an IgG1 antibody.

3. The nucleic acid of claim 1, wherein the encoded antibody is an IgG2 antibody.

4. The nucleic acid of claim 1, wherein the encoded antibody is an IgG3 antibody.

5. The nucleic acid of claim 1, wherein the encoded antibody is an IgG4 antibody.

6. A vector comprising the nucleic acid of claim 1.

7. A mammalian host cell comprising the vector of claim 6.

8. A method of producing the humanized antibody of claim 1 comprising culturing a mammalian host cell that comprises a vector comprisinp the nucleic acid of claim 1 and recovering said antibody.

9. An isolated nucleic acid molecule encoding a humanized antibody that specifically binds to IgE comprising a VH domain and a VL domain, wherein:
   (a) the VH domain comprises the VH domain of SEQ ID NO:8 in which the alanine residue at position 61 of SEQ ID NO:8 is replaced by an asparagine residue, the aspartic acid residue at position 62 of SEQ ID NO:8 is replaced by a proline residue, the valine residue at position 64 of SEQ ID NO:8 is replaced by a leucine residue, and the phenylalanine residue at position 68 of SEQ ID NO:8 is replaced by an isoleucine residue, in which said positions correspond to Kabat numbering 60, 61, 63 and 67, respectively and
   (b) the VL domain comprises the VL domain of SEQ ID NO:9.

10. An isolated nucleic acid molecule encoding a polypeptide comprising a VH domain and a VL domain, wherein:
    (a) the VH domain comprises the VH domain of SEQ ID NO:8 in which the alanine residue at position 61 of SEQ ID NO:8 is replaced by an asparagine residue, the aspartic acid residue at position 62 of SEQ ID NO:8 is replaced by a proline residue, the valine residue at position 64 of SEQ ID NO:8 is replaced by a leucine residue, and the phenylalanine residue at position 68 of SEQ ID NO:8 is replaced by an isoleucine residue, in which said positions correspond to Kabat numbering 60, 61, 63 and 67, respectively and (b) the VL domain comprises the VL domain of SEQ ID NO:9.

11. The nucleic acid of claim 9, wherein the encoded antibody is an IgG1 antibody.

12. The nucleic acid of claim 9, wherein the encoded antibody is an IgG2 antibody.

13. The nucleic acid of claim 9, wherein the encoded antibody is an IgG3 antibody.

14. The nucleic acid of claim 9, wherein the encoded antibody is an IgG4 antibody.

15. The nucleic acid of claim 10, wherein the encoded polypeptide further comprises an IgG1 constant domain.

16. The nucleic acid of claim 10, wherein the encoded polypeptide further comprises an IgG2 constant domain.

17. The nucleic acid of claim 10, wherein the encoded polypeptide further comprises an IgG3 constant domain.

18. The nucleic acid of claim 10, wherein the encoded polypeptide further comprises an IgG4 constant domain.

19. A vector comprising the nucleic acid of claim 9.

20. A vector comprising the nucleic acid of claim 10.

21. A mammalian host cell comprising the vector of claim 19.

22. A method of producing the humanized antibody of claim 9 comprising culturing a mammalian host cell that comprises a vector comprising the nucleic acid of claim 9 and recovering said antibody.

23. A mammalian host cell comprising the vector of claim 20.

24. An isolated nucleic acid molecule encoding a humanized antibody that specifically binds to IgE comprising a VH domain and a VL domain, wherein:

(a) the VH domain comprises the VH domain of SEQ ID NO:8 in which the alanine residue at position 61 of SEQ ID NO:8 is replaced by an asparagine residue, the aspartic acid residue at position 62 of SEQ ID NO:8 is replaced by a proline residue, and the phenylalanine residue at position 68 of SEQ ID NO:8 is replaced by an isoleucine residue, in which said positions correspond to Kabat numbering 60, 61 and 67, respectively, and (b) the VL domain comprising the VL domain of SEQ ID NO:9.

25. An isolated nucleic acid molecule encoding a polypeptide comprising a VH domain and a VL domain, wherein:

(a) the VH domain comprises the VH domain of SEQ ID NO:8 in which the alanine residue at position 61 of SEQ ID NO:8 is replaced by an asparagine residue, the aspartic acid residue at position 62 of SEQ ID NO:8 is replaced by a proline residue, and the phenylalanine residue at position 68 of SEQ ID NO:8 is replaced by an isoleucine residue, in which said positions correspond to Kabat numbering 60, 61 and 67, respectively, and (b) the VL domain comprising the VL domain of SEQ ID NO:9.

26. The nucleic acid of claim 24, wherein the encoded antibody is an IgG1 antibody.

27. The nucleic acid of claim 24, wherein the encoded antibody is an IgG2 antibody.

28. The nucleic acid of claim 24, wherein the encoded antibody is an IgG3 antibody.

29. The nucleic acid of claim 24, wherein the encoded antibody is an IgG4 antibody.

30. The nucleic acid of claim 25, wherein the encoded polypeptide further comprises an IgG1 constant domain.

31. The nucleic acid of claim 25, wherein the encoded polypeptide sequenoe further comprises an IgG2 constant domain.

32. The nucleic acid of claim 25, wherein the encoded polypeptide further comprises an IgG3 constant domain.

33. The nucleic acid of claim 25, wherein the encoded polypeptide further comprises an IgG4 constant domain.

34. A vector comprising the nucleic acid of claim 24.

35. A vector comprising the nucleic acid of claim 25.

36. A mammalian host cell comprising the vector of claim 34.

37. A method of producing the humanized antibody of claim 24 comprising culturing a mammalian host cell that comprises a vector comprising the nucleic acid of claim 24 and recovering said antibody.

38. A mammalian host cell comprising the vector of claim 35.

39. An isolated nucleic acid molecule encoding a humanized antibody that specifically binds to IgE comprising a VH domain and a VL domain, wherein:

(a) the VH domain comprises the VH domain of SEQ ID NO:8 in which the valine residue at position 49 of SEQ ID NO:8 is replaced by a methionine residue, the alanine residue at position 50 of SEQ ID NO:8 is replaced by a glycine residue, the alanine residue at position 61 of SEQ ID NO:8 is replaced by an asparagine residue, the valine residue at position 64 of SEQ ID NO:8 is replaced by a leucine residue, the phenylalanine residue at position 68 of SEQ ID NO:8 is replaced by an isoleucine residue, the isoleucine residue at position 70 of SEQ ID NO:8 is replaced by a valine residue, the methionine residue at position 83 of SEQ ID NO:8 is replaced by a leucine residue, and the leucine residue, at position 86 of SEQ ID NO:8 is replaced by an alanine residue, in which said positions correspond to Kabat numbering 48, 49, 60, 63, 67, 69, 82 and 82c, respectively, and (b) the VL domain comprises the VL domain of SEQ ID NO:9 in which the alanine residue at position 13 of SEQ ID NO:9 is replaced by a valine residue, the valine residue at position 19 of SEQ ID NO:9 is replaced by an alanine residue, the valine residue at position 62 of SEQ ID NO:9 is replaced by an isoleucine residue, the leucine residue at position 82 of SEQ ID NO:9 is replaced by a valine residue, and the valine residue at position 108 of SEQ ID NO:9 is replaced by a leucine residue, in which said positions correspond to Kabat numbering 10, 19, 58, 78 and 104, respectively.

40. An isolated nucleic acid molecule encoding a polypeptide comprising a VH domain and a VL domain, wherein:

(a) the VH domain comprises the VH domain of SEQ ID NO:8 in which the valine residue at position 49 of SEQ ID NO:8 is replaced by a methionine residue, the alanine residue at position 50 of SEQ ID NO:8 is replaced by a glycine residue, the alanine residue at position 61 of SEQ ID NO:8 is replaced by an asparagine residue, the valine residue at position 64 of SEQ ID NO:8 is replaced by a leucine residue, the phenylalanine residue at position 68 of SEQ ID NO:8 is replaced by an isoleucine residue, the isoleucine residue at position 70 of SEQ ID NO:8 is replaced by a valine residue, the methionine residue at position 83 of SEQ ID NO:8 is replaced by a leucine residue, and the leucine residue at position 86 of SEQ ID NO:8 is replaced by an alanine residue, in which said positions correspond to Kabat numbering 48, 49, 60, 63, 67, 69, 82 and 82c, respectively, and (b) the VL domain comprises the VL domain of SEQ ID NO:9 in which the alanine residue at position 13 of SEQ ID NO:9 is replaced by a valine residue, the valine residue at position 19 of SEQ ID NO:9 is replaced by an alanine residue, the valine residue at position 62 of SEQ ID NO:9 is replaced by an isoleucine residue, the leucine residue at position 82 of SEQ ID NO:9 is replaced by a valine residue, and the valine residue at position 108 of SEQ ID NQ:9 is replaced by a leucine residue, in which said positions correspond to Kabat numbering 13, 19, 58, 78 and 104, respectively.

41. The nucleic acid of claim 39, wherein the encoded antibody is an IgG1 antibody.

42. The nucleic acid of claim 39, wherein the encoded antibody is an IgG2 antibody.

43. The nucleic acid of claim 39, wherein the encoded antibody is an IgG3 antibody.

44. The nucleic acid of claim 39, wherein the encoded antibody is an IgG4 antibody.

45. The nucleic acid of claim 40, wherein the polypeptide further comprises an IgG1 constant domain.

46. The nucleic acid of claim 40, wherein the encoded polypeptide further comprises an IgG2 constant domain.

47. The nucleic acid of claim 40, wherein the encoded polypeptide further comprises an IgG3 constant domain.

48. The nucleic acid of claim 40, wherein the encoded polypeptide further comprises an IgG4 constant domain.

49. A vector comprising the nucleic acid of claim 39.

50. A vector comprising the nucleic acid of claim 40.

51. A mammalian host cell comprising the vector of claim 49.

52. A method of producing the humanized antibody of claim 39 comprising culturing a mammalian host cell that comprises a vector comprising the nucleic acid of claim 39 and recovering said antibody.

53. A mammalian host cell comprising the vector of claim 50.

* * * * *